US011007161B1

(12) United States Patent
Morrison

(10) Patent No.: US 11,007,161 B1
(45) Date of Patent: *May 18, 2021

(54) IBUPROFEN NANOPARTICLE CARRIERS ENCAPSULATED WITH HERMATIC SURFACTANT FILMS

(71) Applicant: Eric Morrison, West Saint Paul, MN (US)

(72) Inventor: Eric Morrison, West Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/165,904

(22) Filed: Oct. 19, 2018

Related U.S. Application Data

(63) Continuation-in-part of application No. 15/635,359, filed on Jun. 28, 2017, now Pat. No. 10,561,627, which is a continuation-in-part of application No. 14/985,570, filed on Dec. 31, 2015, now abandoned.

(60) Provisional application No. 62/098,382, filed on Dec. 31, 2014.

(51) Int. Cl.
| | |
|---|---|
| *A61K 31/192* | (2006.01) |
| *A61K 9/51* | (2006.01) |
| *A61K 9/107* | (2006.01) |
| *A61K 9/00* | (2006.01) |
| *B82Y 5/00* | (2011.01) |
| *A61K 9/127* | (2006.01) |

(52) U.S. Cl.
CPC .......... *A61K 31/192* (2013.01); *A61K 9/0014* (2013.01); *A61K 9/1075* (2013.01); *A61K 9/127* (2013.01); *A61K 9/51* (2013.01); *B82Y 5/00* (2013.01); *Y10S 977/773* (2013.01)

(58) Field of Classification Search
CPC ....... A61K 9/0014; A61K 9/1075; B82Y 5/00
See application file for complete search history.

(56) References Cited

U.S. PATENT DOCUMENTS

| | | | |
|---|---|---|---|
| 1,000,113 A | 8/1911 | O'connor et al. | |
| 1,082,633 A | 12/1913 | Hedstrom et al. | |
| 4,701,470 A | 10/1987 | Heckler | |
| 4,918,103 A | 4/1990 | Park et al. | |
| 4,937,254 A | 6/1990 | Sheffield et al. | |
| 4,944,949 A | 7/1990 | Story et al. | |
| 5,093,133 A | 3/1992 | Wisniewski et al. | |
| 5,100,918 A | 3/1992 | Sunshine et al. | |
| 5,104,656 A * | 4/1992 | Seth ..................... | A61K 9/0014 424/401 |
| 5,210,099 A | 5/1993 | Mody et al. | |
| 5,654,337 A | 8/1997 | Roentsch et al. | |
| 5,976,566 A | 11/1999 | Samour et al. | |
| 6,004,566 A | 12/1999 | Friedman | |
| 6,191,285 B1 | 2/2001 | Esser et al. | |
| 6,221,370 B1 * | 4/2001 | Wadle ..................... | A61K 8/06 424/401 |
| 6,221,391 B1 | 4/2001 | Rouffer | |
| 6,287,592 B1 | 9/2001 | Dickinson | |
| 6,368,618 B1 | 4/2002 | Jun et al. | |
| 6,506,404 B1 | 1/2003 | Mayan et al. | |
| 6,525,214 B1 | 2/2003 | Armitage et al. | |
| 6,623,761 B2 | 9/2003 | Hassan | |
| 6,716,443 B1 | 4/2004 | Abribat et al. | |
| 6,927,241 B2 | 8/2005 | Ansmann et al. | |
| 7,052,715 B2 | 5/2006 | Fishman | |
| 7,132,452 B2 | 11/2006 | Lee et al. | |
| 7,473,432 B2 | 1/2009 | Cevc et al. | |
| 7,922,802 B2 | 4/2011 | Valls et al. | |
| 8,211,887 B2 | 7/2012 | Richlin et al. | |
| 8,445,545 B2 | 5/2013 | DeSica et al. | |
| 8,454,945 B2 | 6/2013 | McCook et al. | |
| 8,470,886 B2 | 6/2013 | King-Smith et al. | |
| 8,541,470 B2 | 9/2013 | Davis | |
| 8,613,961 B1 | 12/2013 | Filippova et al. | |
| 8,802,656 B2 | 8/2014 | Lichtenberger | |
| 8,865,187 B2 | 10/2014 | Lichtenberger | |
| 9,526,682 B2 | 12/2016 | Sebillotte-Arnaud et al. | |
| 9,561,174 B2 | 2/2017 | Carter et al. | |
| 10,561,627 B2 * | 2/2020 | Morrison ............. | A61K 31/192 |
| 2003/0147927 A1 | 8/2003 | Kahn et al. | |
| 2005/0032900 A1 | 2/2005 | Krauser | |
| 2007/0027217 A1 | 2/2007 | Ehrlich | |
| 2007/0044810 A1 * | 3/2007 | Ramirez ............. | A61K 9/0014 128/898 |
| 2007/0269393 A1 | 11/2007 | Wepfer | |

(Continued)

FOREIGN PATENT DOCUMENTS

| | | |
|---|---|---|
| CA | 2815477 A1 | 11/2013 |
| CN | 102579350 B | 7/2012 |

(Continued)

OTHER PUBLICATIONS

Jn Israelachvili, S Marcelja, RG Horn. "Physical principles of membrane organization." Quarterly Reviews of Biophysics, vol. 13(2), 1980, pp. 121-200. (Year: 1980).*

JB Cannon. "Lipids in Transdermal and Topical Drug Delivery." American Pharmaceutical Review. https://www.americanpharmaceuticalreview.com/Featured-Articles/170872-Lipids-in-Transdermal-and-Topical-Drug-Delivery/ accessed Nov. 20, 2019, published Dec. 1, 2014, pp. 1-9. (Year: 2014).*

GW Lu, P Gao. "Emulsions and Microemulsions for Topical and Transdermal Drug Delivery." Chapter 3 of "Handbook of Non-Invasive Drug Delivery Systems" ISBN 9780815520252, copyright 2010, pp. 59-94. (Year: 2010).*

(Continued)

*Primary Examiner* — Isaac Shomer
(74) *Attorney, Agent, or Firm* — Mitchell A. Rossman; Terra Nova Patent Law, PLLC

(57) ABSTRACT

The present invention provides nanoparticle dispersion for topical delivery to skin of a mammal. The nanoparticle dispersion includes: a sorbitan ester surfactant; one or more poly(ethoxylate) surfactants, one or more lipids; and ibuprofen. Methods of preparing various water continuous dispersion of nanoparticles are also provided.

8 Claims, 17 Drawing Sheets

(56) References Cited

U.S. PATENT DOCUMENTS

| | | |
|---|---|---|
| 2007/0270507 A1 | 11/2007 | Weiss et al. |
| 2008/0069779 A1* | 3/2008 | Tamarkin ............... A61K 8/046 424/45 |
| 2008/0075767 A1 | 3/2008 | Jin et al. |
| 2009/0258069 A1 | 10/2009 | Burnier et al. |
| 2010/0137443 A1* | 6/2010 | Carter .................. A61K 9/0014 514/570 |
| 2010/0158993 A1 | 6/2010 | Spann-Wade et al. |
| 2011/0237674 A1 | 9/2011 | Zhang et al. |
| 2012/0157536 A1* | 6/2012 | Shah ..................... A61K 9/7015 514/567 |
| 2012/0232141 A1* | 9/2012 | Hustvedt ............. A61K 9/4858 514/547 |
| 2012/0269914 A1* | 10/2012 | Susilo ..................... A61K 8/97 424/777 |
| 2012/0329875 A1 | 12/2012 | Carter et al. |
| 2013/0085171 A1 | 4/2013 | Ray, II et al. |
| 2013/0109674 A1 | 5/2013 | Leighton et al. |
| 2013/0243707 A1 | 9/2013 | Green et al. |
| 2018/0125766 A1 | 5/2018 | Rodriguez et al. |

FOREIGN PATENT DOCUMENTS

| | | |
|---|---|---|
| EP | 0225162 A2 | 6/1987 |
| EP | 0249561 A2 | 12/1987 |
| EP | 0946156 B1 | 2/2002 |
| EP | 2301525 A1 | 3/2011 |
| EP | 2301525 B1 | 9/2013 |
| GB | 2239600 A | 7/1991 |
| GB | 2287404 A | 9/1995 |
| GB | 2327041 A | 1/1999 |
| GB | 2476155 A | 6/2011 |
| GB | 2476155 A1 | 6/2011 |
| WO | WO8702891 A1 | 5/1987 |
| WO | WO8707506 A1 | 12/1987 |
| WO | WO8807853 A1 | 10/1988 |
| WO | WO9523596 A1 | 9/1995 |
| WO | WO9834597 A1 | 8/1998 |
| WO | WO2009147269 A1 | 12/2009 |
| WO | WO2014039939 A1 | 3/2014 |
| WO | WO2014106048 A2 | 7/2014 |

OTHER PUBLICATIONS

MakingCosmetics.com. "FAQ: Difference Between Surfactants and Emulsifiers." https://www.makingcosmetics.com/FAQ-Difference-Between-Surfactants-and-Emulsifiers_ep_149-1.html accessed Feb. 21, 2020, pp. 1-2. (Year: 2020).*

I James. "Surfactants and Emulsifiers." https://www.dermascope.com/ingredients/surfactants-and-emulsifiers?print=1&tmpl=component accessed Feb. 21, 2020, pp. 1-5. (Year: 2020).*

AM Evans. "Comparative Pharmacology of S(+)-Ibuprofen and (RS)-Ibuprofen." Clinical Rheumatology, 2001, Supplement 1, pp. S9-S14. (Year: 2001).*

Huabing Chen, Xueling Chang, Danrong Du, Jin Li, Huibi Xu, Xiangliang Yang. "Microemulsion-based hydrogel formulation of ibuprofen for topical delivery." International Journal of Pharmaceutics 315 (2006) 52-58. (Year: 2006).*

Lijuan Wang, Jinfeng Dong, Jing Chen, Julian Eastoe, Xuefeng Li. "Design and optimization of a new self-nanoemulsifying drug delivery system." Journal of Colloid and Interface Science 330 (2009) 443-448. (Year: 2009).*

Salim N, Basri M, Rahman M, Abdullah D, Basri H. Modification of palm kernel oil esters nanoemulsions with hydrocolloid gum for enhanced topical delivery of ibuprofen. Int J Nanomedicine. 2012;7:4739-47. doi: 10.2147/IJN.S34700.

Wasankar S, Faizi S, Deshmuk A. Formulation and development of liposomal gel for topical drug delivery system International Journal of Pharmaceutical Sciences & Research;Nov. 2012, vol. 3 Issue 11, p. 4461.

Abdullah G, Abdulkarim M, Salman I, Ameer O, Yam M, Mutee A, Chitneni M, Mandi E, Basri M, Sattar M, NoorA. In vitro permeation and in vivo anti-inflammatory and analgesic properties of nanoscaled emulsions containing ibuprofen for topical delivery. International Journal of Nanomedicine. 2011;6:387-396. doi:10.2147/IJN.S14667.

Irfan M, Verma S, Ram A. Preparation and characterization of ibuprofen loaded transferosome as a novel carrier for transdermal drug delivery system. Asian Journal of Pharmaceutical & Clinical Research;Jul. 2012, vol. 5 Issue 3, p. 162.

Stott P, Williams A, Barry B. Transdermal delivery from eutectic systems: enhanced permeation of a model drug, ibuprofen. J Control Release. Jan. 2, 1998;50(1-3):297-308.

Abdel-Mottaleb M, Neumann D, Lamprecht A. Lipid nanocapsules for dermal application: a comparative study of lipid-based versus polymer-based nanocarriers. Eur J Pharm Biopharm. Sep. 2011;79(1):36-42. doi: 10.1016/j.ejpb.2011.04.009.

Abdel-Mottaleb M, Neumann D, Lamprecht A. In vitro drug release mechanism from lipid nanocapsules (LNC). Int J Pharm. May 10, 2010;390(2):208-13. doi: 10.1016/j.ijpharm.2010.02.001.

Hu L, Hu Q, Yang J. Enhancement of transdermal delivery of ibuprofen using microemulsion vehicle. Iran J Basic Med Sci. Oct. 2014;17(10):760-6.

Chen H, Chang X, Du D, Li J, Xu H, Yang X. Microemulsion-based hydrogel formulation of ibuprofen for topical delivery. Int J Pharm. Jun. 6, 2006;315(1-2):52-8.

Generic development of topical dermatologic products: formulation development, process development, and testing of topical dermatologic products. Chang R, Raw A, Lionberger R, Yu L. AAPS J. Jan. 2013;15(1):41-52. doi: 10.1208/s12248-012-9411-0.

Lamprecht A, Saumet J, Roux J, Benoit J. Lipid nanocarriers as drug delivery system for ibuprofen in pain treatment. Int J Pharm. Jul. 8, 2004;278(2):407-14.

Heurtault B, Saulnier P, Pech B, Proust J, Benoit J. A Novel Phase Inversion-Based Process for the Preparation of Lipid Nanocarriers. Pharm Res (2002) 19: 875.

Heurtault B, Saulnier P, Pech B, Venier-Julienne M, Proust J, Phan-Tan-Luu R, Benoit J. The influence of lipid nanocapsule composition on their size distribution. Eur J Pharm Sci. Jan. 2003;18(1):55-61.

Thomas O, Lagarce F. Lipid nanocapsules: a nanocarrier suitable for scale-up process. Drug Del. Sci. Tech., 23(6) 555-559 2013.

Heurtault B, Saulnier P, Pech B, Benoit JP, Proust JE. Interfacial stability of lipid nanocapsules. Colloids Surf B Biointerfaces 2003; 30:225.

Dominkus M, Nicolakis M, Kotz R, Wilkinson F, Kaiser R, Chlud K. Comparison of tissue and plasma levels of ibuprofen after oral and topical administration. Arzneimittelforschung. Dec. 1996;46(12):1138-43.

Mondino A, Zanolo G, Giachetti C, Testaguzza F, Engels B, Wagener H. (1983) Humankinetische Untersuchungen mit Ibuprofen, medwelt 34: 1052-1054.

Berner G, Engels B, Vögtle-Junkert U. Percutaneous ibuprofen therapy with Trauma-Dolgit gel: bioequivalence studies. Drugs Exp Clin Res. 1989;15(11-12):559-64.

Gohel M, Nagori S. Fabrication and Evaluation of Hydrogel Thickened Microemulsion of Ibuprofen for Topical Delivery. Indian Journal of Pharmaceutical Education and Research, 2010; 44(2):189-196.

Patel A, Bell M, O'Connor C, Inchley A, Wibawa J, Lane M. Delivery of ibuprofen to the skin. Int J Pharm. Nov. 30, 2013;457(1):9-13. doi: 10.1016/j.ijpharm.2013.09.019.

Wang et al., "Design and Optimization of a new self-nanoemulsifying drug delivery system" J. Coloidal and Interface Science, 330 (2009) 4443-448.

D Cipolla, H Wu, I Gonda, S Eastman, T Redelmeier, H-K Chan. "Modifying the Release Properties of Liposomes Toward Personalized Medicine." Journal of Pharmaceutical Sciences, vol. 103, 2014, pp. 1851-1862. (Year: 2014).

H. Lee et al, "Cryogenic Electron Microscopy Study of Nanoemulsion Formation from Microemulsions," Langmuir. Sep. 16, 2014; 30(36):10826-33. doi: 10.1021/la502207f.

(56) References Cited

OTHER PUBLICATIONS

N. Dragicevic-Curic et al "Temoporfin-loaded invasomes: Development, characterization and in vitro skin penetration studies," J Control Release. Apr. 7, 2008;127(1):59-69. doi: 10.1016/j.jconrel. 2007.12.013.

S. Koudelka et al "Liposomal paclitaxel formulations," J Control Release. Nov. 10, 2012;163(3)322-34. doi: 10.1016/i.jconrel.2012. 09.006.

S. Mura et al "Penetration enhancer-containing vesicles (PEVs) as carriers for cutaneous delivery of minoxidil," Int J Pharm. Oct. 1, 2009;380(1-2):72-9. doi: 10.1016/j.ijpharm.009.06.040.

Y Barenholz "Doxil®—the first FDA-approved nano-drug: lessons learned," J Control Release. Jun. 10, 2012;160(2):117-34. doi: 10.1016/j.jconrel.2012.03.020.

P. Photos et al, "Polymer vesicles in vivo: correlations with PEG molecular weight," J Control Release. Jul. 31, 2003;90(3):323-34.

L. Spernath et al, "Phase transitions in O/W lauryl acrylate emulsions during phase inversion, studied by light microscopy and cryo-TEM," Colloids and Surfaces A: Physicochem. Eng. Aspects 332 (2009):19-25.

A. Dhanikula et al "Fluorescence anisotropy, FT-IR spectroscopy and 31-P NMR studies on the interaction of paclitaxel with lipid bilayers," Lipids. Jun. 2008;43(6):569-79. doi: 10.1007/s11745-008-3178-1.

S. Mayer et al "Vitamin E-enriched nanoemulsions formed by emulsion phase inversion: Factors influencing droplet size and stability," J Colloid Interface Sci. Jul. 15, 2013;402:122-30. doi: 10.1016/j.jcis.2013.04.016.

T. Cheng et al "Computation of Octanol-Water Partition Coefficients by Guiding an Additive Model with Knowledge," J Chem Inf Model. Nov.-Dec. 2007;47(6):2140-8.

L. Wolf et al "Cryo-TEM imaging of a novel microemulsion system of silicone oil with an anionic/nonionic surfactant mixture," Soft Matter, 2010,6, 5367-5374 DOI: 10.1039/C0SM00049C.

T. Tadros et al "Formation and stability of nano-emulsions," Adv Colloid Interface Sci. May 20, 2004;108-109:303-18.

S. Simoes et al "Permeabilisation and solubilisation of soybean phosphatidylcholine bilayer vesicles, as membrane models, by polysorbate, Tween 80," Eur J Pharm Sci. Nov. 2005;26(3-4):307-17.

T. Dash "Liposome as a Potential Drug Delivery System: A Review," International Research Journal of Pharmacy. 2013, 4 (1): 6-12.

A. Bangham et al "Negative staining of phospholipids and their structural modification by surface-active agents as observed in the electron microscope," J Mol Biol. May 1964; 8:660-8.

O. Ogunsola et al "Structural analysis of "flexible" liposome formulations: new insights into the skin-penetrating ability of soft nanostructures," Soft Matter, 2012, 8, 10226 DOI: 10.1039/c2sm26614h.

G. Cevc et al "Ultradeformable lipid vesicles can penetrate the skin and other semi-permeable barriers unfragmented. Evidence from double label CLSM experiments and direct size measurements," Biochimica et Biophysica Acta 1564 (2002) 21-30.

C. Caddeo et al "Inhibition of skin inflammation in mice by diclofenac in vesicular carriers: Liposomes, ethosomes and PEVs," Int J Pharm. Feb. 25, 2013;443(1-2):128-36. doi: 10.1016/j.ijpharm. 2012.12.041.

M. Badran et al "Influence of the Flexible Liposomes on the Skin Deposition of a HydrophilicModel Drug, Carboxyfluorescein: Dependency on Their Composition," The ScientificWorld Journal vol. 2012, Article ID 134876, 9 pages doi:10.1100/2012/134876.

H. Coster et al "The effect of temperature on lipid-n-alkane interactions in lipid bilayers," Biochimica et Biophysica Acta 857 (1986) 95-104.

C. Marianecci et al "Niosomes from 80s to present: The state of the art," Adv Colloid Interface Sci. Mar. 2014;205:187-206. doi: 10.1016/j.cis.2013.11.018.

S Salunkhe et al "Formulation, development and evaluation of ibuprofen loaded nanoemulsion prepared by Nanoprecipitation technique: Use of factorial design approach as a tool of optimization methodology," Journal of Pharmaceutical Investigation Apr. 2014; 44(4):273-290. DOI: 10.1007/s40005-014-0125-4.

F. Formiga et al "Influence of a lipophilic drug on the stability of emulsions: an important approach on the development of lipidic carriers," Int J Pharm. Nov. 1, 2007; 344(1-2):158-60.

L. Panigrahi, et al "The effect of pH and organic ester penetration enhancers on skin permeation kinetics of terbutaline sulfate from pseudolatex-type transdermal delivery systems through mouse and human cadaver skins," AAPS PharmSciTech. Sep. 30, 2005;6(2):E167-73.

H. Mahmngkol et al; "Permeation study of five formulations of alpha-tocopherol acetate through human cadaver skin," J Cosmet Sci 56 (2): 91-103 (2005).

S. Ali et al "Skin pH: From Basic Science to Basic Skin Care," Acta Derm Venereol 2013; 93: 261-267.

N. Price et al "Structural characterization of novel sophorolipid biosurfactantsfrom a newly identified species of *Candida* yeast," Carbohydrate Research 348 (2012) 33-41.

F. Ishii et al "Properties of various phospholipid mixtures as emulsifiers or dispersing agents in nanoparticle drug carrier preparations," Colloids and Surfaces B: Biointerfaces 41 (2005) 257-262.

S. Hong et al "Effects of triglycerides on the hydrophobic drug loading capacity of saturated phosphatidylcholine-based liposomes," International Journal of Pharmaceutics 483 (2015) 142-150.

F. Schambil et al "Interfacial and colloidal properties of cosmetic emulsions containing fatty alcohol and fatty alcohol polyglycol ethers," Progr Colloid & Polymer Sol 73:37-47 (1987).

P. Izquierdo et al "Phase Behavior and Nano-emulsion Formation by the Phase Inversion Temperature Method," Langmuir 2004, 20, 6594-6598.

W. Zheng et al "Quantum Dots Encapsulated within Phospholipid Membranes: Phase-Dependent Structure, Photostability, and Site-Selective Functionalization," J. Am. Chem. Soc., 2014, 136 (5), pp. 1992-1999 DOI: 10.1021/a411339f).

A. Wohl et al "Silicate Esters of Paclitaxel and Docetaxel: Synthesis, Hydrophobicity, Hydrolytic Stability, Cytotoxicity, and Prodrug Potential," J. Med. Chem. 2014, 57, 2368-2379.

C. Rentel et al, "Niosomes as a novel peroral vaccine delivery system," International Journal of Pharmaceutics 186 (1999) 161-167.

N. Salim et al "Phase Behaviour, Formation and Characterization of Palm-Based Esters Nanoemulsion Formulation containing Ibuprofen," J Nanomedic Nanotechnol 2:113. doi:10.4172/2157-7439. 1000113.

Kanicky et al Effect of Premicellar Aggregation on the pKa of Fatty Acid Soap Solutions, Langmuir, 2003, 19 (6), pp. 2034-2038 DOI: 10.1021/la020672y.

J. Bauer, ed. Cell Electrophoresis, p. 118. 1994, CRC Press.

W. Griffin "Calculating the HLB Values of Non-Ionic Surfactants," J. Soc. Cosmet. Chem., 5, 249-56 (1954). Downloaded from the internet at http://joumal.sccsonline.org/contents/cc1954/cc005n04. html on Dec. 30, 2015.

V. Wilkerson the Chemistry of Human Epidermis: II. The Isoelectric Points of the Stratum Corneum, Hair, and Nails as Determined by Electrophoresis, J. Biol. Chem. 1935, 112:329-335.

A. Ito et al "Medical Application of Functionalized Magnetic Nanoparticles," Journal of Bioscience and Engineering, vol. 100, No. 1, 1-11. 2005.

J. Seddon et al "Polymorphism of Lipid-Water Systems," from the Handbook of Biological Physics, vol. 1, ed. R. Lipowsky, and E Sackmann. (c) 1995, pp. 1115-116Elsevier Science B.V. ISBN 0-444-81975-4.

Wang et al, "Design and Optimization of a New Self-Nanoemulsifying Drug Delivery System," Journal of COlooid and Interface Science,, 330, 209, 443-448.

Zhang Y, Brown K, Siebenaler K, Determan A, Dohmeier D, Hansen K. Development of Lidocaine-Coated Microneedle Product for Rapid, Safe, and Prolonged Local Analgesic Action Pharm Res (2012) 29: 170. doi:10.1007/s11095-011-0524-4.

El Maghraby G, Williams A, Barry B. Can drug-bearing liposomes penetrate intact skin? J Pharm Pharmacol. Apr. 2006;58(4):415-29.

(56) References Cited

OTHER PUBLICATIONS

Sobanko J, Miller C, Alster T. Topical anesthetics for dermatologic procedures: a review. Dermatol Surg. May 2012;38(5):709-21. doi: 10.1111/j.1524-4725.2011.02271.x.

Bucalo B, Mirikitani E, Mo R. Comparison of Skin Anesthetic Effect of Liposomal Lidocaine, Nonliposomal Lidocaine, and EMLA Using 30-minute Application Time. Dermatologic Surgery. 24(5):537-541, May 1998.

Alster T. Review of lidocaine/tetracaine cream as a topical anesthetic for dermatologic laser procedures. Pain Ther. Jun. 2013;2(1):11-9. doi: 10.1007/s40122-013-0010-2.

Lee H, Morrison E, Zhang Q, McCormick A. Cryogenic transmission electron microscopy study: preparation of vesicular dispersions by quenching microemulsions. J Microsc. Sep. 2016;263(3):293-9. doi: 10.1111/jmi.12392.

de Paula E, Cereda C, Tofoli G, Franz-Montan M, Fraceto L, de Araújo D. Drug delivery systems for local anesthetics. Recent Pat Drug Deliv Formul. Jan. 2010;4(1):23-34.

N. Dragicevic-Curic et al "Temoporfin-loaded invasomes: Development, characterization and in vitro skin penetration studies," J Control Release. Apr. 7, 2008;127(1):59-69. doi: 10.1016/j.jconrel.2007.12.013.

S. Koudelka et al "Liposomal paclitaxel formulations," J Control Release. Nov. 10, 2012;163(3)322-34. doi: 10.1016/i.jconrel.2012.09.006.

S. Mura et al "Penetration enhancer-containing vesicles (PEVs) as carriers for cutaneous delivery of minoxidil," Int J Pharm. Oct. 1, 2009;380(1-2):72-9. doi: 10.1016/j.ijpharm.2009.06.040.

W. Griffin "Calculating the HLB Values of Non-Ionic Surfactants," J. Soc. Cosmet. Chem., 5, 249-56 (1954). Downloaded from the internet at http://journal.scconline.org/contents/cc1954/cc005n04.html on Dec. 30, 2015.

Rao J, McClements D. Stabilization of phase inversion temperature nanoemulsions by surfactant displacement. J Agric Food Chem. Jun. 9, 2010;58(11):7059-66. doi: 10.1021/jf100990r.

Sadtler V, Marie, Emmanuelle M. Chapter 24. Low Energy Emulsification Methods for Nanoparticles Synthesis. Delivery of Nanoparticles ed. Hashim A. (2012) doi:10.5772/35087.

Kiran S, Acosta E. HLD-NAC and the Formation and Stability of Emulsions Near the Phase Inversion Point. Ind. Eng. Chem. Res., 2015, 54 (25), pp. 6467-6479 DOI: 10.1021/acs.iecr.5b00382.

Shinoda K, Arai H. The Correlation between Phase Inversion Temperature in Emulsion and Cloud Point in Solution of Nonionic Emulsifier J. Phys. Chem., 1964, 68 (12), pp. 3485-3490 DOI: 10.1021/j100794a007.

Okuyama H, Ikeda Y, Kasai S, Imamori K, Takayama K, Nagai T. Influence of non-ionic surfactants, pH and propylene glycol on percutaneous absorption of piroxicam from cataplasm. Int J Pharm. Sep. 20, 1999;186(2):141-8.

Walters K, Bialik W, Brain K. The effects of surfactants on penetration across the skin. Int J Cosmet Sci. Dec. 1993; 15(6):260-71. doi: 10.1111/j.1467-2494.1993.tb00572.x.

Vidlářová L, Hanuš J, Veselý M, Ulbrich P, Štěpánek F, Zbytovská J. Effect of lipid nanoparticle formulations on skin delivery of a lipophilic substance. Eur J Pharm Biopharm. Nov. 2016;108:289-296. doi: 10.1016/j.ejpb.2016.07.016.

\* cited by examiner

IBUPROFEN NANOPARTICLE CARRIERS ENCAPSULATED WITH HERMATIC SURFACTANT FILMS

RELATED APPLICATIONS

This is a continuation-in-part application that claims priority to U.S. patent application Ser. No. 15/635,359, filed Jun. 28, 2017, which claims priority to U.S. patent application Ser. No. 14/985,570 fled Dec. 31, 2015, which claims priority to U.S. Provisional Patent Application Ser. No. 62/098,382 filed Dec. 31, 2014, both of which are hereby incorporated by reference in their entirety for all purposes.

BACKGROUND OF THE INVENTION

It is often the case that poorly water-soluble pharmacological compounds are difficult to administer to living organisms in an effective manner because of one or more problems including poor bioavailability, too rapid decomposition and excretion, which creates a need for frequent re-dosing, and irritation or tissue damage at the location of introduction.

The bioavailability of poorly water soluble, orally administered drug is a major challenge for the pharmaceutical industry as many newly launched drugs possess low aqueous solubility, which leads to poor dissolution and low absorption. Furthermore, poor solubility results in variability in absorption and lack of dose proportionality. Compounding the problems of poor absorption is the problem that pharmacologically useful compounds may be substantially degraded in the gastrointestinal tract before absorption can occur. Solutions have been proposed including Self-Emulsifying Drug Delivery Systems (SEDDS's), defined as isotropic mixtures of one or more hydrophilic solvents and co-solvents/surfactants that are capable to form fine oil-in-water (o/w) emulsions upon mild agitation and dilution in gastrointestinal fluids, and various types of emulsions or suspensions.

A further problem of oral drug administration is the potential for harm to the gastrointestinal tract. This problem is most commonly associated with non-steroidal anti-inflammatory drugs (NSAID's). NSAID's diminish the production of prostaglandins by inhibiting cyclooxygenase enzymes, either COX-1 or COX-2 or both. NSAID's that inhibit COX-1 enzymes interfere with prostaglandin production and blood clotting in the gastrointestinal tract and oral ingestion may lead to gastrointestinal distress and ulceration. For this reason, COX-2 inhibitors have been sought as oral medications. However, COX-2 inhibiting drugs are also associated with increased risk of heart attack and stroke and currently celecoxib is the only COX-2 NSAID available in the United States, and it is available only by prescription. Topical administration is a potential solution for COX-1 inhibiting NSAID's including aspirin (ortho-acetyl salicylic acid), ibuprofen (p-isobutyl 2-propenoic acid), and naproxen ((+)-(S)-2-(6-methoxynaphthalen-2-yl) propanoic acid), which are considered much safer than COX-2 inhibitors and have long been available as over the counter products. Unfortunately, in the United States the only products of these medications are oral forms, and topical products available elsewhere are characterized by poor bioavailability. While it is very desirable to provide COX-1 inhibiting NSAID compounds as topical medications, the only topical NSAID products available in the United States contain diclofenac as the sodium salt dissolved in solvent systems based on propylene glycol, alcohols and dimethylsulfoxide, and are known to cause irritation in significant proportions of patients.

Whether for oral, rectal, intraperitoneal or topical administration, there is a need to improve the usefulness of poorly water soluble high $K_{ow}$ pharmacologically active compounds including NSAID's by improving bioavailability of drug delivery via transmucosal and transdermal routes. For parenteral administration, there is a need to provide effective dispersed forms of poorly water soluble high $K_{ow}$ drugs.

It would be desirable to have liposomal forms of high $K_{ow}$ compounds including NSAID's that are safe, offer high bioavailability, have pharmacologically meaningful concentrations of active compounds, have acceptable organoleptic properties and cosmetically desirable feel, and which are available from simple and reliable manufacturing processes.

A problem with nanoparticle carriers for high pKow, water insoluble drugs is failure to effectively encapsulate the drug in the nanoparticle, resulting in formation of crystals of drug in the product. Crystallization of active pharmaceutical ingredients is unacceptable because a portion of the drug is in a form with lower bioavailability, resulting in diminished efficacy and lack of dose proportionality. Heretofore there are no known nanoparticles which effectively encapsulate ibuprofen as the neutral high pKow, water insoluble compound.

SUMMARY OF THE INVENTION

It has been discovered that stable nanoparticle dispersion compositions containing relatively high and useful concentrations of ibuprofen can be provided by effective encapsulation of ibuprofen within nanoparticles by interfacial films including saccharide residues. Useful ibuprofen containing nanoparticle compositions include dispersions of lipoleosomes, defined as unilamellar vesicular nanoparticles including an oil swollen lipid bilayer surrounding an aqueous core, nanocapsules which are a liquid core surrounded by an interfacial film of surfactant compounds that solids at room temperature, and nanopouches, which are a liquid core surrounded by an interfacial film of surfactant compounds that are liquid or semi-solid at room temperature. Unilamellar vesicle nanoparticles, which contain high proportions of hydrophobic compounds are termed lipoleosomes to signify liposomes which contain a significant proportion of oleophilic compounds. Lipoleosomes in which the exterior surface is nonionic and hydrophilic are also capable to be categorized as niosomes. Ibuprofen containing nanoparticle dispersions can be prepared by the decomposition of weakly lamellar microemulsion phases in a simple one step process without the need for high shear mixing. Weakly lamellar microemulsion phases including polyethoxylated surfactants that may occur at relatively higher temperatures can be decomposed by dilution with water or aqueous compositions, by cooing, or both to give a variety of nanoparticle dispersion containing product forms, for example, liquids, gels, and yield stress fluids. Physicochemical properties of ibuprofen containing nanoparticles, for example, flexibility and adaptability can be optimized to maximize bioavailability of active pharmacological compounds, and compositions free of phospholipids, cholesterol, or both can be prepared.

The present invention provides a nanoparticle dispersion for topical delivery to skin of a mammal. The nanoparticle dispersion includes: a sorbitan ester surfactant; one or more poly(ethoxylate) surfactants selected from an ether poly (ethoxylate) surfactant with a number average chain length greater than about 30 and the combination of an ether poly(ethoxylate) surfactant with a number average chain length greater than about 20 and an ester poly(ethoxylate) surfactant with a number average chain length greater than about 40; wherein a mole ratio of ether poly(ethoxylate) surfactant to ester poly(ethoxylate) surfactant is greater than about 1.8 to 1 and a combined number average ethoxylate chain length of the combination of the ether poly(ethoxylate) surfactant and the ester poly(ethoxylate) surfactant is greater than about 30; one or more lipids selected from one or more water immiscible oils and a phospholipid; and ibuprofen.

In one embodiment, the sorbitan ester surfactant includes sorbitan oleate. In one embodiment, the ether poly(ethoxylate) surfactant with a number average chain length greater than about 30 includes ceteareth-30. In one embodiment, the ether poly(ethoxylate) surfactant with a number average chain length greater than about 20 includes laureth-23. In one embodiment, the ester poly(ethoxylate) surfactant with a number average chain length greater than about 40 includes PEG100 stearate.

In one embodiment, the one or more water immiscible oils each independently include a medium chain triglyceride oil, caprylic/capric triglyceride, d-limonene, squalane, cetyl palmitate, coco-caprylate/caprate, propylene glycol dicaprylate, mineral oil, sesame oil, spermaceti, vegetable oil, hydrogenated vegetable oil, isopropyl myristate, almond oil, castor oil, hydrogenated castor oil, cocoa butter, coconut oil, safflower oil, shea butter, soybean oil, sunflower seed oil, peanut oil, olive oil, canola oil, diethyl sebacate, diisopropyl adipate, alpha-terpineol, propylene glycol monopalmitostearate, propylene glycol monostearate, butyl stearate, cetearyl ethyhexanoate, cetyl esters wax, ethylhexyl hydroxyl stearate, isopropyl isostearate, isopropyl palmitate, cyclomethicone, or combinations thereof.

In one embodiment, the one or more water immiscible oils each independently include a medium chain triglyceride oil, caprylic/capric triglyceride, d-limonene, squalane, cetyl palmitate, coco-caprylate/caprate, isopropyl myristate, propylene glycol dicaprylate, mineral oil, coconut oi, sesame seed oil, fractionated coconut oil, diisopropyl adipate, or combinations thereof.

In one embodiment, the one or more water immiscible oils each independently comprise a medium chain triglyceride oil caprylic/capric triglyceride, a terpene, a hydrocarbon, a vegetable oil, a fatty acid ester with fatty alcohol, or a diester of an organic diacid compound.

In one embodiment, the phospholipid includes dioleyl phosphatidyl choline. In one embodiment, the volume average particle size of the nanoparticle dispersion is less than about 100 nm. In one embodiment, the ibuprofen has greater than about 95% enantiomeric excess of an S-(+)-optical isomer.

The present invention provides a nanoparticle dispersion for topical delivery to skin of a mammal. The nanoparticle dispersion includes; a sorbitan ester surfactant; an ether poly(ethoxylate) surfactant with a number average chain length greater than about 30; isopropyl myristate; a medium chain triglyceride oil; and ibuprofen.

In one embodiment, the nanoparticle dispersion includes from about 3 weight percent to about 6 weight percent of a sorbitan ester surfactant. In one embodiment, the sorbitan ester surfactant includes sorbitan oleate. In one embodiment, the sorbitan ester surfactant includes from about 3 weight percent to about 6 weight percent of sorbitan oleate. In one embodiment, the sorbitan ester surfactant includes about 4.5 weight percent of sorbitan oleate. In one embodiment, the nanoparticle dispersion includes from about 8 weight percent to about 13 weight percent of an ether poly(ethoxylate) surfactant with a number average chain length greater than about 30. In one embodiment, the ether poly(ethoxylate) surfactant with a number average chain length greater than about 30 includes ceteareth-30. In one embodiment, the nanoparticle dispersion includes from about 8 weight percent to about 13 weight percent of ceteareth-30. In one embodiment, the nanoparticle dispersion includes about 10 weight percent of ceteareth-30. In one embodiment, the nanoparticle dispersion includes from about 10 weight percent to about 15 weight percent of isopropyl myristate. In one embodiment, the nanoparticle dispersion includes about 12.5 weight percent of isopropyl myristate. In one embodiment, the nanoparticle dispersion includes from about 10 weight percent to about 15 weight percent of a medium chain triglyceride oil. In one embodiment, the nanoparticle dispersion includes from about 10 weight percent to about 15 weight percent of fractionated coconut oi. In one embodiment, the nanoparticle dispersion includes about 12.5 weight percent of fractionated coconut oil. In one embodiment, the nanoparticle dispersion includes from about 4 weight percent to about 6 weight percent of ibuprofen. In one embodiment, the nanoparticle dispersion includes about 5 weight percent of ibuprofen. In one embodiment, the volume average particle size of the nanoparticle dispersion is less than about 100 nm. In one embodiment, the ibuprofen has greater than about 95% enantiomeric excess of an S-(+)-optical isomer. In one embodiment, the nanoparticle dispersion further includes a phospholipid.

In one embodiment, the phospholipid includes dioleyl phosphatidyl choline. In one embodiment, the phospholipid includes Phospholipon 90G. In one embodiment, the nanoparticle dispersion includes less than about 3.0 weight percent of Phospholipon 90G. In one embodiment, the nanoparticle dispersion includes less than about 1.0 weight percent of Phospholipon 90G. In one embodiment, the nanoparticle dispersion is does not include a phospholipid. In one embodiment, the nanoparticle dispersion further includes d-limonene. In one embodiment, the nanoparticle dispersion includes from about 1.0 weight percent to about 6.0 weight percent of d-limonene. In one embodiment, the nanoparticle dispersion includes about 3.7 weight percent of d-limonene.

The present invention provides a nanoparticle dispersion for topical delivery to skin of a mammal. The nanoparticle dispersion includes: from about 3 weight percent to about 6 weight percent of a sorbitan ester surfactant; from about 8 weight percent to about 13 weight percent of an ether poly(ethoxylate) surfactant with a number average chain length greater than about 30; from about 10 weight percent to about 15 weight percent of isopropyl myristate; from about 10 weight percent to about 15 weight percent of a medium chain triglyceride oil; and from about 4 weight percent to about 6 weight percent of ibuprofen.

In one embodiment, the sorbitan ester surfactant includes sorbitan oleate. In one embodiment, the sorbitan ester surfactant includes about 4.5 weight percent of sorbitan oleate. In one embodiment, the ether poly(ethoxylate) surfactant with a number average chain length greater than about 30 includes ceteareth-30. In one embodiment, the nanoparticle dispersion includes about 10 weight percent of ceteareth-30. In one embodiment, the nanoparticle dispersion includes about 12.5 weight percent of isopropyl myristate. In one embodiment, the nanoparticle dispersion includes about 12.5 weight percent of fractionated coconut oil. In one embodiment, the nanoparticle dispersion includes about 5 weight percent of ibuprofen. In one embodiment, the volume average particle size of the nanoparticle dispersion is less than about 100 nm. In one embodiment, the ibuprofen has greater than about 95% enantiomeric excess of an S-(+)-optical isomer. In one embodiment, the nanoparticle dispersion further includes a phospholipid.

In one embodiment, the phospholipid includes dioleyl phosphatidyl choline. In one embodiment, the phospholipid includes Phospholipon 90G. In one embodiment, the nanoparticle dispersion includes less than about 3.0 weight percent of Phospholipon 90G. In one embodiment, the nanoparticle dispersion includes less than about 1.0 weight percent of Phospholipon 90G. In one embodiment, the nanoparticle dispersion is does not include a phospholipid. In one embodiment, the nanoparticle dispersion further includes d-limonene. In one embodiment, the nanoparticle dispersion includes from about 1.0 weight percent to about 6.0 weight percent of d-limonene. In one embodiment, the nanoparticle dispersion includes about 3.7 weight percent of d-limonene.

The present invention provides a nanoparticle dispersion for topical delivery to skin of a mammal. The nanoparticle dispersion includes: sorbitan oleate; ceteareth 30; isopropyl myristate; fractionated coconut oil; and ibuprofen.

In one embodiment, the nanoparticle dispersion includes from about 3 weight percent to about 6 weight percent of sorbitan oleate. In one embodiment, the nanoparticle dispersion includes about 4.5 weight percent of sorbitan oleate. In one embodiment, the nanoparticle dispersion includes from about 8 weight percent to about 13 weight percent of ceteareth-30. In one embodiment, the nanoparticle dispersion includes about 10 weight percent of ceteareth-30. In one embodiment, the nanoparticle dispersion includes from about 10 weight percent to about 15 weight percent of isopropyl myristate. In one embodiment, the nanoparticle dispersion includes about 12.5 weight percent of isopropyl myristate. In one embodiment, the nanoparticle dispersion includes from about 10 weight percent to about 15 weight percent of fractionated coconut oi. In one embodiment, the nanoparticle dispersion includes about 12.5 weight percent of fractionated coconut oil. In one embodiment, the nanoparticle dispersion includes from about 4 weight percent to about 6 weight percent of ibuprofen. In one embodiment, the nanoparticle dispersion includes about 5 weight percent of ibuprofen. In one embodiment, the volume average particle size of the nanoparticle dispersion is less than about 100 nm. In one embodiment, the ibuprofen has greater than about 95% enantiomeric excess of an S-(+)-optical isomer. In one embodiment, the nanoparticle dispersion further includes a phospholipid.

In one embodiment, the phospholipid includes dioleyl phosphatidyl choline. In one embodiment, the phospholipid includes Phospholipon 90G. In one embodiment, the nanoparticle dispersion includes less than about 3.0 weight percent of Phospholipon 90G. In one embodiment, the nanoparticle dispersion includes less than about 1.0 weight percent of Phospholipon 90G. In one embodiment, the nanoparticle dispersion is does not include a phospholipid. In one embodiment, the nanoparticle dispersion further includes d-limonene. In one embodiment, the nanoparticle dispersion includes from about 1.0 weight percent to about 6.0 weight percent of d-limonene. In one embodiment, the nanoparticle dispersion includes about 3.7 weight percent of d-limonene.

The present invention provides a nanoparticle dispersion for topical delivery to skin of a mammal. The nanoparticle dispersion includes: from about 3 weight percent to about 6 weight percent of sorbitan oleate; from about 8 weight percent to about 13 weight percent of ceteareth-30; from about 10 weight percent to about 15 weight percent of isopropyl myristate; from about 10 weight percent to about 15 weight percent of a medium chain triglyceride oil; and from about 4 weight percent to about 6 weight percent of ibuprofen.

In one embodiment, the nanoparticle dispersion includes about 4.5 weight percent of sorbitan oleate. In one embodiment, the nanoparticle dispersion includes about 10 weight percent of ceteareth-30. In one embodiment, the nanoparticle dispersion includes about 12.5 weight percent of isopropyl myristate. In one embodiment, the nanoparticle dispersion includes from about 10 weight percent to about 15 weight percent of fractionated coconut oil. In one embodiment, the nanoparticle dispersion includes about 12.5 weight percent of fractionated coconut oi. In one embodiment, the nanoparticle dispersion includes about 5 weight percent of ibuprofen. In one embodiment, the volume average particle size of the nanoparticle dispersion is less than about 100 nm. In one embodiment, the ibuprofen has greater than about 95% enantiomeric excess of an S-(+)-optical isomer. In one embodiment, the nanoparticle dispersion further includes a phospholipid In one embodiment, the phospholipid includes dioleyl phosphatidyl choline. In one embodiment, the phospholipid includes Phospholipon 90G. In one embodiment, the nanoparticle dispersion includes less than about 3.0 weight percent of Phospholipon 90G. In one embodiment, the nanoparticle dispersion includes less than about 1.0 weight percent of Phospholipon 90G. In one embodiment, the nanoparticle dispersion is does not include a phospholipid. In one embodiment, the nanoparticle dispersion further includes d-limonene. In one embodiment, the nanoparticle dispersion includes from about 1.0 weight percent to about 6.0 weight percent of d-limonene. In one embodiment, the nanoparticle dispersion includes about 3.7 weight percent of d-limonene.

The present invention provides a nanoparticle dispersion for topical delivery to skin of a mammal. The nanoparticle dispersion includes: sorbitan ester surfactant; an ether poly(ethoxylate) surfactant with a number average chain length greater than about 20; an ester poly(ethoxylate) surfactant with a number average chain length greater than about 40; wherein a mole ratio of ether poly(ethoxylate) surfactant to ester poly(ethoxylate) surfactant is greater than about 4 to 1 and a combined number average ethoxylate chain length of the combination of the ether poly(ethoxylate) surfactant and the ester poly(ethoxylate) surfactant is greater than about 30; isopropyl myristate; a phospholipid; and ibuprofen.

In one embodiment, the nanoparticle dispersion includes from about 2 weight percent to about 4 weight percent of a sorbitan ester surfactant. In one embodiment, the sorbitan ester surfactant includes sorbitan oleate. In one embodiment, the nanoparticle dispersion includes from about 2 weight percent to about 4 weight percent of sorbitan oleate. In one embodiment, the nanoparticle dispersion includes about 3 weight percent of sorbitan oleate. In one embodiment, the nanoparticle dispersion includes from about 5 weight percent to about 7 weight percent of ether poly(ethoxylate) surfactant with a number average chain length greater than about 20. In one embodiment, the ether poly(ethoxylate) surfactant with a number average chain length greater than about 20 includes laureth-23. In one embodiment, the nanoparticle dispersion includes from about 5 weight percent to about 7 weight percent of laureth-23. In one embodiment, the nanoparticle dispersion includes about 6 weight percent of laureth-23.

In one embodiment, the nanoparticle dispersion includes from about 3 weight percent to about 6 weight percent of an ester poly(ethoxylate) surfactant with a number average chain length greater than about 40. In one embodiment, the ester poly(ethoxylate) surfactant with a number average chain length greater than about 40 includes PEG100 stearate. In one embodiment, the nanoparticle dispersion includes from about 3 weight percent to about 6 weight percent of PEG100 stearate. In one embodiment, the nanoparticle dispersion includes about 4.5 weight percent of PEG100 stearate. In one embodiment, the nanoparticle dispersion includes from about 10 weight percent to about 30 weight percent of isopropyl myristate. In one embodiment, the nanoparticle dispersion includes about 20 weight percent of isopropyl myristate. In one embodiment, the phospholipid includes dioleyl phosphatidyl choline.

In one embodiment, the phospholipid includes from about 0.3 weight percent to about 3.0 weight percent of dioleyl phosphatidyl choline. In one embodiment, the phospholipid includes about 0.5 weight percent of dioleyl phosphatidyl choline. In one embodiment, the phospholipid includes Phospholipon 90G. In one embodiment, the phospholipid includes from about 0.3 weight percent to about 3.0 weight percent of Phospholipon 90G. In one embodiment, the phospholipid includes about 0.5 weight percent of Phospholipon 90G. In one embodiment, the volume average particle size of the nanoparticle dispersion is less than about 100 nm. In one embodiment, the ibuprofen has greater than about 95% enantiomeric excess of an S-(+)-optical isomer. In one embodiment, the nanoparticle dispersion further includes d-limonene. In one embodiment, the nanoparticle dispersion includes from about 3 weight percent to about 7 weight percent of d-limonene. In one embodiment, the nanoparticle dispersion includes about 5.1 weight percent of d-limonene.

The present invention provides a nanoparticle dispersion for topical delivery to skin of a mammal. The nanoparticle dispersion includes: from about 2 weight percent to about 4 weight percent of a sorbitan ester surfactant; from about 5 weight percent to about 7 weight percent of ether poly (ethoxylate) surfactant with a number average chain length greater than about 20; from about 3 weight percent to about 6 weight percent of an ester poly(ethoxylate) surfactant with a number average chain length greater than about 40; from about 10 weight percent to about 30 weight percent of isopropyl myristate; from about 0.3 weight percent to about 5 weight percent of a phospholipid; and from about 4 weight percent to about 6 weight percent of ibuprofen. In one embodiment, the sorbitan ester surfactant includes sorbitan oleate. In one embodiment, the nanoparticle dispersion includes from about 2 weight percent to about 4 weight percent of sorbitan oleate. In one embodiment, the nanoparticle dispersion includes about 3 weight percent of sorbitan oleate. In one embodiment, the ether poly(ethoxylate) surfactant with a number average chain length greater than about 20 includes laureth-23. In one embodiment, the nanoparticle dispersion includes from about 5 weight percent to about 7 weight percent of laureth-23. In one embodiment, the nanoparticle dispersion includes about 6 weight percent of laureth-23. In one embodiment, the nanoparticle dispersion about 20 weight percent of isopropyl myristate. In one embodiment, the ester poly(ethoxylate) surfactant with a number average chain length greater than about 40 includes PEG100 stearate. In one embodiment, the nanoparticle dispersion includes from about 3 weight percent to about 6 weight percent of PEG100 stearate. In one embodiment, the nanoparticle dispersion includes about 4.5 weight percent of PEG100 stearate. In one embodiment, the phospholipid includes dioleyl phosphatidyl choline.

In one embodiment, the phospholipid includes from about 0.3 weight percent to about 3.0 weight percent of dioleyl phosphatidyl choline. In one embodiment, the phospholipid includes about 0.5 weight percent of dioleyl phosphatidyl choline. In one embodiment, the phospholipid includes Phospholipon 90G. In one embodiment, the phospholipid includes from about 0.3 weight percent to about 3.0 weight percent of Phospholipon 90G. In one embodiment, the phospholipid includes about 0.5 weight percent of Phospholipon 90G. In one embodiment, the nanoparticle dispersion further includes d-limonene. In one embodiment, the nanoparticle dispersion includes from about 3 weight percent to about 7 weight percent of d-limonene. In one embodiment, the nanoparticle dispersion includes about 5.1 weight percent of d-limonene.

In one embodiment, the volume average particle size of the nanoparticle dispersion is less than about 100 nm. In one embodiment, the ibuprofen has greater than about 95% enantiomeric excess of an S-(+)-optical isomer.

The present invention provides a nanoparticle dispersion for topical delivery to skin of a mammal. The nanoparticle dispersion includes: sorbitan oleate; laureth-23; PEG-100 stearate; wherein a mole ratio of laureth-23 to PEG-100 stearate is greater than about 4 to 1 and a combined number average ethoxylate chain length of all poly(ethoxylate) surfactants in the nanoparticle dispersion is greater than about 30; isopropyl myristate; a phospholipid; and ibuprofen.

In one embodiment, the nanoparticle dispersion includes from about 2 weight percent to about 4 weight percent of sorbitan oleate. In one embodiment, the nanoparticle dispersion includes about 3 weight percent of sorbitan oleate. In one embodiment, the nanoparticle dispersion includes from about 5 weight percent to about 7 weight percent of laureth-23. In one embodiment, the nanoparticle dispersion includes about 6 weight percent of laureth-23. In one embodiment, the nanoparticle dispersion includes from about 3 weight percent to about 6 weight percent of PEG-100 stearate. In one embodiment, the nanoparticle dispersion includes about 4.5 weight percent of PEG100 stearate. In one embodiment, the nanoparticle dispersion includes from about 10 weight percent to about 30 weight percent of isopropyl myristate. In one embodiment, the nanoparticle dispersion includes about 20 weight percent of isopropyl myristate. In one embodiment, the nanoparticle dispersion includes from about 0.3 weight percent to about 5 weight percent of a phospholipid. In one embodiment, the phospholipid includes dioleyl phosphatidyl choline. In one embodiment, the phospholipid includes from about 0.3 weight percent to about 3.0 weight percent of dioleyl phosphatidyl choline. In one embodiment, the phospholipid includes about 0.5 weight percent of dioleyl phosphatidyl choline. In one embodiment, the phospholipid includes Phospholipon 90G. In one embodiment, the phospholipid includes from about 0.3 weight percent to about 3.0 weight percent of Phospholipon 90G. In one embodiment, the phospholipid includes about 0.5 weight percent of Phospholipon 90G. In one embodiment, the nanoparticle dispersion includes from about 4 weight percent to about 6 weight percent of ibuprofen. In one embodiment, the nanoparticle dispersion includes about 5 weight percent of ibuprofen. In one embodiment, the volume average particle size of the nanoparticle dispersion is less than about 100 nm. In one embodiment, the ibuprofen has greater than about 95% enantiomeric excess of an S-(+)-optical isomer.

The present invention provides a nanoparticle dispersion for topical delivery to skin of a mammal. The nanoparticle dispersion includes: from about 2 weight percent to about 4 weight percent of sorbitan oleate; from about 5 weight percent to about 7 weight percent of laureth-23; from about 3 weight percent to about 6 weight percent of PEG-100 stearate; from about 10 weight percent to about 30 weight percent of isopropyl myristate; from about 0.3 weight percent to about 5 weight percent of a phospholipid; and from about 4 weight percent to about 6 weight percent of ibuprofen.

In one embodiment, the nanoparticle dispersion includes about 3 weight percent of sorbitan oleate. In one embodiment, the nanoparticle dispersion includes about 6 weight percent of laureth-23. In one embodiment, the nanoparticle dispersion includes about 4.5 weight percent of PEG100 stearate. In one embodiment, the nanoparticle dispersion includes about 20 weight percent of isopropyl myristate. In one embodiment, the phospholipid includes dioleyl phosphatidyl choline. In one embodiment, the phospholipid includes from about 0.3 weight percent to about 3.0 weight percent of dioleyl phosphatidyl choline. In one embodiment, the phospholipid includes about 0.5 weight percent of dioleyl phosphatidyl choline. In one embodiment, the phospholipid includes Phospholipon 90G. In one embodiment, the phospholipid includes from about 0.3 weight percent to about 3.0 weight percent of Phospholipon 90G. In one embodiment, the phospholipid includes about 0.5 weight percent of Phospholipon 90G. In one embodiment, the nanoparticle dispersion includes from about 4 weight percent to about 6 weight percent of ibuprofen. In one embodiment, the nanoparticle dispersion includes about 5 weight percent of ibuprofen. In one embodiment, the volume average particle size of the nanoparticle dispersion is less than about 100 nm. In one embodiment, the ibuprofen has greater than about 95% enantiomeric excess of an S-(+)-optical isomer. In one embodiment, the nanoparticle dispersion further includes d-limonene. In one embodiment, the nanoparticle dispersion includes from about 3 weight percent to about 7 weight percent of d-limonene. In one embodiment, the nanoparticle dispersion includes about 5.1 weight percent of d-limonene.

BRIEF DESCRIPTION OF THE DRAWINGS

Embodiments of the invention may be best understood by referring to the following description and accompanying drawings, which illustrate such embodiments. In the drawings.

Figure 1:
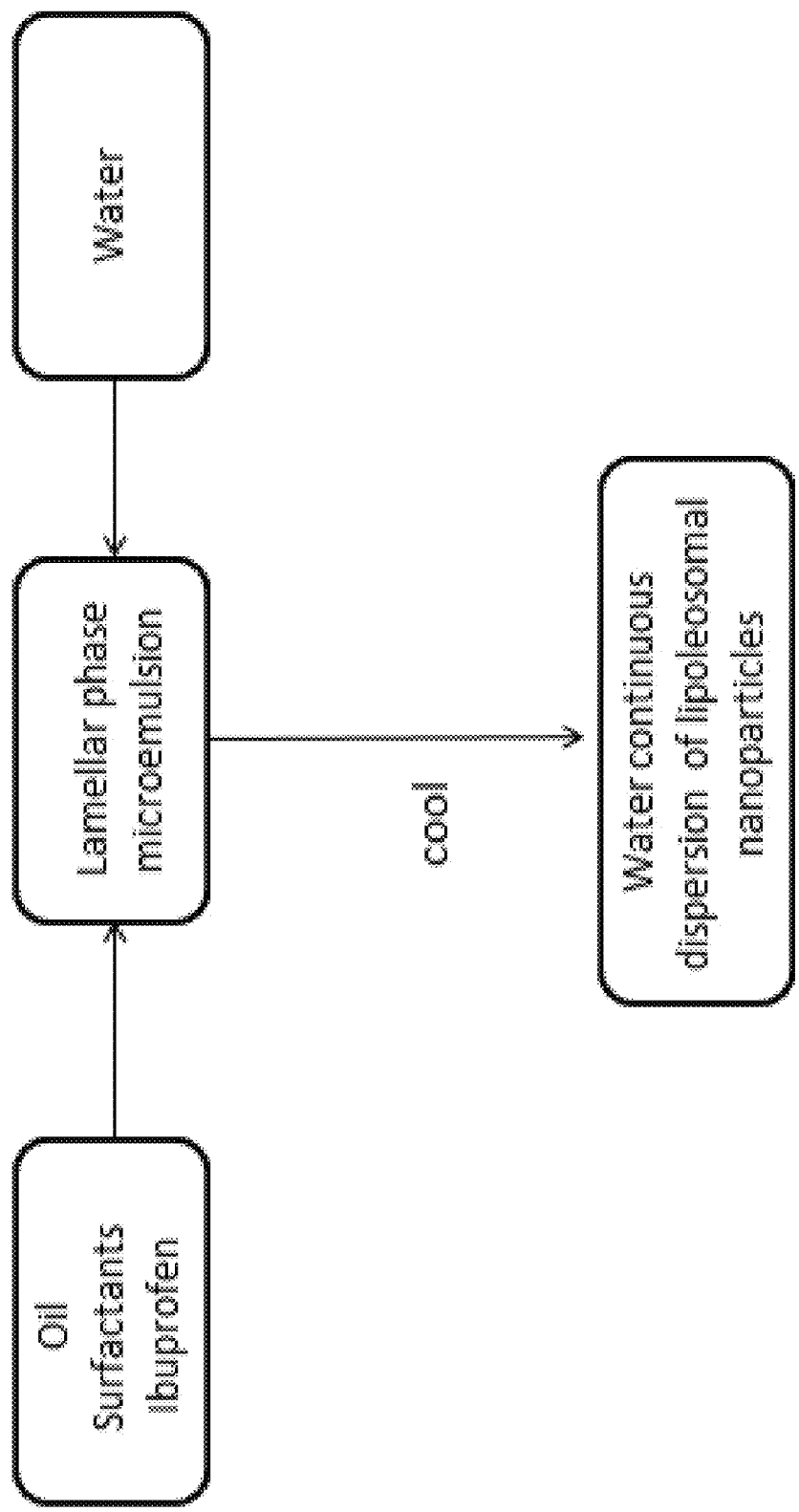
FIGS. 1-4 represent various flow charts illustrating the preparation of exemplary nanoparticle dispersion compositions.

The drawings are not necessarily to scale. Like numbers used in the figures refer to like components, steps, and the like. However, it will be understood that the use of a number to refer to a component in a given figure is not intended to limit the component in another figure labeled with the same number.

DETAILED DESCRIPTION OF THE INVENTION

The present invention provides a water continuous dispersion of nanoparticles including ibuprofen; one or more high HLB surfactants; one or more low HLB surfactants, wherein the one or more low HLB surfactants each independently include a saccharide residue; and one or more oils. Method of preparing various water continuous dispersion of nanoparticles are also provided.

The present invention provides a nanoparticle dispersion for topical delivery to skin of a mammal. The nanoparticle dispersion includes: a sorbitan ester surfactant; one or more poly(ethoxylate) surfactants selected from an ether poly(ethoxylate) surfactant with a number average chain length greater than about 30 and the combination of an ether poly(ethoxylate) surfactant with a number average chain length greater than about 20 and an ester poly(ethoxylate) surfactant with a number average chain length greater than about 40; wherein a mole ratio of ether poly(ethoxylate) surfactant to ester poly(ethoxylate) surfactant is greater than about 1.8 to 1 and a combined number average ethoxylate chain length of the combination of the ether poly(ethoxylate) surfactant and the ester poly(ethoxylate) surfactant is greater than about 30; one or more lipids selected from one or more water immiscible oils and a phospholipid; isopropyl myristate; and ibuprofen.

The present invention provides a nanoparticle composition having including: ibuprofen; one or more water immiscible oils; one or more low HLB surfactants; one or more polyethoxylated high HLB surfactants; water, and wherein the nanoparticle composition includes an external phase and a dispersed phase, the particles of the dispersed phase including a surfactant monolayer or bilayer and one or more compounds with saccharide residues. Methods of using these compositions to treat various disorders in a patient in need thereof are also provided.

The present invention provides a nanoparticle composition having including: ibuprofen; one or more water immiscible oils; one or more low HLB surfactants including saccharide residues each independently having a HLB value of less than 10; one or more polyethoxylated high HLB surfactants each independently having a HLB value of equal to or greater than 14; water, and wherein the nanoparticle composition includes an external phase and a dispersed phase, the particles of the dispersed phase including a surfactant monolayer or bilayer.

The present invention provides a nanoparticle composition having including: ibuprofen; one or more water immiscible oils; one or more low HLB surfactants including each independently having a HLB value of less than 10; one or more polyethoxylated high HLB surfactants including saccharide residues each independently having a HLB value of equal to or greater than 14; water, and wherein the nanoparticle composition includes an external phase and a dispersed phase, the particles of the dispersed phase including a surfactant monolayer or bilayer.

The present invention provides a nanoparticle composition having including: ibuprofen; one or more water immiscible oils; one or more low HLB surfactants including saccharide residues each independently having a HLB value of less than 10; one or more polyethoxylated high HLB surfactants each independently having a HLB value of equal to or greater than 14; a water soluble polysaccharide compound, water, and wherein the nanoparticle composition includes an external phase and a dispersed phase, the particles of the dispersed phase including a surfactant monolayer or bilayer.

The present invention provides a nanoparticle composition having including: ibuprofen; one or more water immiscible oils; one or more low HLB surfactants each independently having a HLB value of less than 10; one or more polyethoxylated high HLB surfactants each independently having a HLB value of equal to or greater than 14; one or more medium HLB surfactants including a saccharide residue each independently having a HLB value between 10 and 14, water, and wherein the nanoparticle composition includes an external phase and a dispersed phase, the particles of the dispersed phase including a surfactant monolayer or bilayer.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events, which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*. Merriam-Webster Inc., Springfield, Mass., 1993 and *The American Heritage Dictionary of the English Language*, Houghton Mifflin, Boston Mass., 1981.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example, about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term 'administration' refers to a method of placing a device to a desired site. The placing of a device can be by any pharmaceutically accepted means, for example, by swallowing, retaining it within the mouth until the drug has been dispensed, placing it within the buccal cavity, inserting, implanting, attaching, etc. These and other methods of administration are known in the art.

As used herein, the term "active pharmaceutical ingredient," or API, refers to a molecular entity adapted for treatment of a malcondition in a patient in need thereof.

As used herein, the term "comprising" or "comprises" is intended to mean that the compositions and methods include the recited elements, but not excluding others.

As used herein, the phrase "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the phrase "consisting of" shall mean excluding more than trace elements of other ingredients and substantial method steps.

As used herein, the terms "consisting essentially of" and "consisting of" are embodied in the term "comprising."

As used herein, the term "delivery" refers to the release of a drug from a device including that drug into an environment surrounding the device. The environment into which the drug so released mayor may not be the ultimate site of activity for that drug. In some instances, the released drug may need to be transported to its ultimate site of activity.

As used herein, the term "dermis" refers to the sensitive connective tissue layer of the skin located below the epidermis, containing nerve endings, sweat and sebaceous glands, and blood and lymph vessels. Histologically, the dermis consists of a papillary layer and a reticular layer. The papillary layer contains the vessels and nerve endings supplying the epidermis. The reticular consists predominantly of elastic fibers and collagen.

As used herein, the term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the API.

As used herein, the term "dispersing agent" refers to an agent that facilitates the formation of a dispersion of one or more internal phases in a continuous phase. Examples of such dispersions include suspensions and emulsions, wherein the continuous phase may be water, for example, and the internal phase is a solid or a water-immiscible liquid, respectively. Thus, dispersing agents may include suspending agents and emulsifying agents.

As used herein, the term "dosage form" refers to a physical and chemical composition of an active pharmaceutical ingredient (API) that is adapted for administration to a patient in need thereof. The inventive dosage form is a tablet. By a tablet is meant a relatively hard, compact object, suitable for oral ingestion, prepared by compression of a powder including an active pharmaceutical ingredient and, usually, excipients.

As used herein, the term "dosing event" refers to administration of an antiviral agent to a patient in need thereof, which event may encompass one or more releases of an antiviral agent from a drug dispensing device. Thus, the term "dosing event," as used herein, includes, but is not limited to, installation of a continuous delivery device (e.g., a pump or other controlled release injectible system); and a single subcutaneous injection followed by installation of a continuous delivery system.

As used herein, the phrase "capric/caprylic triglyceride" refers to fractionated coconut oil, which is also called capric/caprylic triglyceride (CAS No. 65381-09-1).

As used herein, the term "drug" refers to a therapeutic agent or a diagnostic agent and includes any substance, other than food, used in the prevention, diagnosis, alleviation, treatment, or cure of a disease. *Stedman's Medical Dictionary*, 25*th* Edition (1990). The drug can include any substance disclosed in at least one of: *The Merck Index*, 13*th* Edition, 1998, published by Merck & Co., Rahway, N.J.; Pei-Show Juo, *Concise Dictionary of Biomedicine and Molecular Biology*, (1996); *U.S. Pharmacopeia Dictionary*, 2000 Edition; and *Physician's Desk Reference*, 2001 Edition.

As used herein, the term "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

As used herein, the term "enantiomeric excess" refers to the degree to which a sample of a compound of a chiral substance contains one enantiomer in greater amounts than the other. Percent enantiomeric excess is defined as=100*([enantiomer 1]−[enantiomer 2])/([enantiomer 1]+[enantiomer 2]).

As used herein, the term "epidermis" refers to the outer, protective, nonvascular layer of the skin of vertebrates, covering the dermis. The epidermis consists histologically of five layers, i.e., the stratum corneum, the stratum lucidum, the stratum granulosum, the stratum spinosum, and the stratum basale.

As used herein, the term "essential oil" refers to a volatile oil derived from the leaves, stem, flower or twigs of plants or synthetically-made compounds that have the same chemical attributes. The essential oil usually carries the odor or flavor of the plant. Chemically, each plant essential oil or derivative thereof, which may be extracted from natural sources or synthetically made, generally contains, as a major constituent, an acyclic monoterpene alcohol or aldehyde, a benzenoid aromatic compound containing at least one oxygenated substituent or side chain, or a monocarbocyclic terpene generally having a six-membered ring bearing one or more oxygenated substituents.

As used herein, the term "essential oi" includes derivatives thereof, including racemic mixtures, enantiomers, diastereomers, hydrates, salts, solvates, metabolites, analogs, and homologs Essential oils, their chemistry and plant families are known in the art. See, for example, S. Price, Aromatherapy Workbook—Understanding Essential Oils from Plant to Bottle, (HarperCollins Publishers, 1993; J. Rose, The Aromatherapy Book—Applications & Inhalations (North Atlantic Books, 1992); and The Merck Index (12th Ed. 1996), each of which is incorporated herein by reference.

As used herein, the term "HLB" refers to Hydrophile-Lipophile Balance, which is an empirical expression for the relationship of the hydrophilic ("water-loving") and hydrophobic ("water-hating") groups of a surfactant.

As used herein, the phrase "low HLB surfactant" refers to a surfactant with an HLB value of less than 10.

As used herein, the phrase "high HLB surfactant" refers to a surfactant with an HLB value of equal to or greater than 14.

As used herein, the phrase "medium HLB surfactant" refers to a surfactant with an HLB value of equal between 10 and 14.

As used herein, the phrase "High $K_{ow}$ pharmacologically active compounds" refers to useful pharmacologically active compounds that have a $pK_{ow}$ value greater than about 1.5.

As used herein, the term "immersing" refers to dipping, plunging, or sinking into a liquid.

As use herein, the term "immiscible" refers to polymers that will not mix or remain mixed with each other, although at certain conditions, for example, high temperatures, they might mix, but any such mixture will typically be thermodynamically unstable and will typically separate into distinct phases at lower temperatures.

As used herein, the terms "include," "for example," "such as," and the like are used illustratively and are not intended to limit the present invention.

As used herein, the terms "individual," "host," "subject," and "patient" are used interchangeably, and refer to a mammal, including, but not limited to, primates, including simians and humans.

As used herein, the term "infection" refers to the invasion of the host by germs that reproduce and multiply, causing disease by local cell injury, release of poisons, or germ-antibody reaction in the cells. The infection can be in a mammal (e.g., human).

As used herein, the term "lipid" refers fats and fat-derived materials. See, e.g., *Concise Chemical and Technical Dictionary*, 4*th* Edition, Chemical Publishing Co., Inc., p. 704, New York, N.Y. (1986).

As used herein, the term "liquid" refers to a substance that undergoes continuous deformation under a shearing stress. See, e.g., *Concise Chemical and Technical Dictionary*, 4*th* Edition, Chemical Publishing Co., Inc., p. 707, New York, N.Y. (1988).

As used herein, the term "mammal" refers to any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, for example, horses, cattle, sheep, and goats, and research and domestic species, including dogs, cats, mice, rats, guinea pigs, and rabbits.

As used herein, the phrase "medium chain triglyceride oil" refers to the chemical with CAS Number 438544-49-1.

As used herein, the term "miscible" refers to two or more polymeric materials that will form a homogeneous mixture, that is, dissolve in each other. As used herein, the term "molecular weight" refers to a weight-average molecular weight, as is well known in the art.

As used herein, the term "molecular weight" refers to a weight-average molecular weight, as is well known in the art.

As used herein, the term "oil" refers to any of various lubricious, hydrophobic and combustible substances obtained from animal, vegetable and mineral matter. Suitable oils may include petroleum-based oil derivatives, for example, purified petrolatum and mineral oil. Petroleum-derived oils include aliphatic or wax-based oils, aromatic or asphalt-based oils and mixed base oils and may include relatively polar and non-polar oils. "Non-polar" oils are generally oils, for example, petrolatum or mineral oil or its derivatives, which are hydrocarbons and are more hydrophobic and lipophilic compared to synthetic oils, for example, esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the water phase, which is used herein.

As used herein, the terms "optional" or "optionally" mean that the subsequently described event or condition may but need not occur, and that the description includes instances where the event or condition occurs and instances in which it does not.

As used herein, the term "patient" refers to a warm-blooded animal, and preferably a mammal, for example, a cat, dog, horse, cow, pig, mouse, rat, or primate, including a human.

As used herein, the term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications, for example, *The United States Pharmacopeia* describe the analytical criteria to assess the pharmaceutical acceptability of numerous ingredients of interest.

As used herein, the term "pharmacologically active agent" refers to a chemical compound, complex or composition that exhibits a desirable effect in the biological context, i.e., when administered to a subject. The term includes pharmacologically active, pharmaceutically acceptable derivatives of those active agents specifically mentioned herein, including, but not limited to, salts, esters, amides, prodrugs, active metabolites, isomers, analogs, crystalline forms, hydrates, and the like.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

It will be understood that, although the terms first, second, etc., may be used herein to describe various elements, these elements should not be limited by these terms. These terms are only used to distinguish one element from another. For example, a first element could be termed a second element, and, similarly, a second element could be termed a first element without departing from the teachings of the disclosure.

As used herein, the terms "prevent," "preventative," "prevention," "protect," and "protection" refer to medical procedures that keep the malcondition from occurring in the first place. The terms mean that there is no or a lessened development of disease or disorder where none had previously occurred, or no further disorder or disease development if there had already been development of the disorder or disease.

As used herein, the term "%" or "percent" refers to weight percent (%).

As used herein, the term "polysaccharide" refers to biological carbohydrate molecules consisting of carbon (C), hydrogen (H) and oxygen (O) formed from linking saccharides through glycosidic bonds As used herein, the term "purified" compound refers to a compound that is present in a given quantity at a concentration of at least 50%, 60%, 70%, 80%, 90% and intermediate values thereof and all in weight percent (%). For example, an isolated compound may be present at 51%, 52%, 53%, 54% and the like. Preferably the compound is present at 90% to 95% and intermediate values thereof. More preferably the compound is present at 95% to 99%, and intermediate values thereof. Even more preferably the compound is present at 99% to 99.9% and intermediate values thereof. Most preferably the compound is present at greater than 99.9% of a given quantity.

As used herein, the term "saccharide" refers to biological carbohydrate molecules consisting of carbon (C), hydrogen (H) and oxygen (O) such as tetroses, pentoses, and hexoses that cannot be broken down to simpler carbohydrates by hydrolysis.

As used herein, the term "saccharide residue" refers to a polyhydric divalent organic group consisting of carbon (C), hydrogen (H) and oxygen (O) that is equivalent to the constituent monosaccharide unit of an oligo- or poly-saccharide, formed by loss the anomeric hydroxy group and of H from one of the remaining hydroxy groups and covalently bonded within a larger molecule, or the polyhydric dehydration product of a constituent monosaccharide unit of an oligo- or poly-saccharide covalently bonded within a larger molecule.

As used herein, the term "skin" refers to the external tissue layer in humans and animals consisting of epidermis and dermis.

As used herein, the phrase "room temperature" refers to a temperature in the range of about 20° C. to about 30° C.

As used herein, the phrase "subcutaneous tissue layer" refers to a tissue layer located below the skin. This tissue layer is typically characterized by a loose meshwork of connective tissue, for example, collagen and elastic fibers. It is rich in small vessels, e.g., arterioles and venoles, and capillaries.

As used herein, the term "therapeutic agent" refers to any agent, which serves to repair damage to a living organism to heal the organism, to cure a malcondition, to combat an infection by a microorganism or a virus, to assist the body of the living mammal to return to a healthy state.

As used herein, the term "therapeutic composition" refers to an admixture with an organic or inorganic carrier or excipient, and can be compounded, for example, with the usual non-toxic, pharmaceutically acceptable carriers for tablets, pellets, capsules, suppositories, solutions, emulsions, suspensions, or other form suitable for use.

As used herein, the term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example, by Chou and Talalay, *Adv. Enzyme Regul.,* 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, the terms "therapy," and "therapeutic" refer to either "treatment" or "prevention," thus, agents that either treat damage or prevent damage are "therapeutic."

As used herein, the phrase "therapeutic kit" refers to a collection of components that can be used in a medical treatment.

As used herein, the phrase "therapeutic dosage" refers to a dosage considered to be sufficient to produce an intended effect.

As used herein, the phrase "Therapeutically effective modality" refers to a manner in which a medical treatment is performed and is considered to be sufficient to produce an intended effect.

As used herein, the term "tissue" refers to an organized biomaterial usually composed of cells.

As used herein, the term "topically" refers to application of the compositions of the present invention to the surface of the skin and mucosal cells and tissues (e.g., alveolar, buccal, lingual, sublingual, masticatory, or nasal mucosa, and other tissues and cells, which line hollow organs or body cavities).

As used herein, the term "topically active agents" refers to compositions of the present invention that are applied to skin or mucosal surfaces. Desired pharmacological results are intended at or near the site of application (contact) to a subject.

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

As used herein, the term "treatment," covers any treatment of a disease in a mammal, particularly in a human, and includes: (a) preventing the disease from occurring in a subject, which may be predisposed to the disease but has not yet been diagnosed as having it; (b) inhibiting the disease, i.e., arresting its development; and (c) relieving the disease, i.e., causing regression of the disease.

As used herein, "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar, and "nm" denotes nanometer.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible sub ranges as well as individual numerical values within that range. For example, description of a range such as 1% to 8% should be considered to have specifically disclosed sub ranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

Development of hydrophobic drug nanomedicines is challenging. Much research has been devoted to making nanoparticles containing the hydrophobic anticancer drug paclitaxel. The FDA approved injectable form of paclitaxel is an ethanoic solution of paclitaxel plus nonionic surfactant which dilutes with water to give an aqueous injectable micellular composition that causes anaphylaxis in large numbers of patients.

It has been advised that liposomes are not useful carriers for lipophilic molecules having large oil/water partition coefficients, for example, paclitaxel based upon unsuccessful attempts to load hydrophobic free base doxorubicin into the walls of liposomes (Y. Barenholz, "Doxil®—the first FDA-approved nano-drug: lessons learned," *J Control Release,* 2012 Jun. 10; 160(2):117-34).

A review of the scientific literature suggests that the capacity of hydrophobic galleries of lipid bilayers for hydrophobic compounds is small. Although lipid bilayers in lyotropic lamellar phases may swell to extremely large spacings (as large as 5000A) upon addition of oil, oil-swelling tends to separates the bilayer into two monolayers (J. Seddon et al., "Polymorphism of Lipid-Water Systems," from the *Handbook of Biological Physics,* Vol. 1, ed. R. Lipowsky, and E. Sackmann. (c) 1995, Elsevier Science B.V. ISBN 0-444-81975-4). Alkanes are reported to partition strongly from lipid bilayers upon contact of alkane containing bilayers with water and the maximum concentration of decane in egg phosphatidyl lipid bilayers in contact with water is less than about 15 weight percent (%) (less than about 0.5 mole fraction: H. Coster et al., "The effect of temperature on lipid-n-alkane interactions in lipid bilayers," *Biochimica et Biophysica Acta,* 857 (1986) 95-104).

Including oil in the galleries of liposomes increases entrapment efficiency of hydrophobic drugs and has also been shown to provide other beneficial effects, for example, as dermal penetration. However, small additions of oil cause undesirable changes in liposome structure from small and unilamellar to larger and multilamellar. Larger amounts of oil cause lipid bilayers to decompose to monolayers in the form of filed emulsion droplets.

Incorporation of a small amount of medium chain triglyceride into dimyristoyl phosphatidyl choline liposomes (weight ratio of oil to surfactant=0.04:1) increased the capacity of the liposome for paclitaxel by a factor of nine but also caused the liposomes to become larger with increased lamellarity (S. Hong et al., "Effects of triglycerides on the hydrophobic drug loading capacity of saturated phosphatidylcholine-based liposomes," *International Journal of Pharmaceutics,* 483 (2015) 142-150). Including a small amount of cineole, citrol and d-limonene terpene oil mixture in unsaturated soybean phosphatidylcholine liposomes (ratio of oil to surfactant=1:10) improved the dermal penetration of temoporfin by nearly threefold but also caused the liposome morphology to change from small unilamellar liposomes to larger predominantly deformed non-spherical liposomes (N. Dragicevic-Curic et al., "Temoporfin-loaded invasomes: Development, characterization and in vitro skin penetration studies," *J Control Release,* 2008 Apr. 7; 127 (1):59-69). Sonicating phospholipid liposomes with medium chain triglyceride oil gives filled emulsion droplets (F. Ishi et al., "Properties of various phospholipid mixtures as emulsifiers or dispersing agents in nanoparticle drug carrier preparations," *Colloids and Surfaces B: Biointerfaces,* 41 (2005) 257-262).

Useful forms for delivery of poorly water soluble, high $K_{ow}$ pharmacologically active compounds are dispersions of solid or liquid phases including active compounds in an aqueous continuous medium particularly with dispersoid sizes in the tens to hundreds of nanometers. Such dispersoids are referred to as nanocarriers and include liposomes, nanocapsules, solid lipid nanoparticles, transfersomes, ethosomes, niosomes, dendrimers, nanoparticles, micellular nanoparticles, and nanoemulsions. Potential benefits of nanocarriers for drug delivery include prolonged duration of action, reduction in the frequency of dosing, more uniform blood plasma levels, reduction of adverse effects, and improvement in bioavailability.

A liposome is an artificially-prepared spherical vesicle composed of a hydrophobic membrane of a lamellar phase lipid bilayer that encapsulates a region of aqueous solution inside. Liposomes are distinct from micelles, reverse micelles, and oil swollen micelles (emulsion droplets), which are composed of monolayers. Liposomes are often composed of phosphatidycholine-enriched phospholipids. Structurally, niosomes are similar to liposomes, in that they include bilayers. However, in niosomes, surface active compounds in bilayers include non-ionic surfactants in place of or in addition to phospholipids. Both liposomes and niosomes may contain hydrophilic drugs within the aqueous volume enclosed by the lipid bilayer and hydrophobic, high $pK_{ow}$ drugs embedded within the hydrophobic layer made up of the tails of surfactants in the bilayer. Liposomes and niosomes may be multilamellar or unilamellar.

Physicochemical properties of nanocarrier systems determine the interaction with biological systems and permeation of nanocarriers through the stratum corneum, the barrier layer of skin. The main physicochemical properties that affect permeation are size, shape, rigidity, and electrostatic charge on the surface of nanoparticles. In the case of liposomes, it has been proposed that deformability improves cellular uptake by facilitating movement through biological barriers, for example, the stratum corneum (the upper layer of skin). Research has also provided evidence that interaction between lipids present in liposome lipid bilayer and the stratum corneum can change the structure of the upper skin in a way that favors the penetration of lipophilic drugs.

Niosomes potentially offer advantages over liposomes because the surfactants can be selected for consistency and stability. In the case of liposomes, the mixture of surfactants typically includes phosphatidylcholine-rich phospholipids and may contain small amounts of other molecules while for niosomes the surfactants typically include a large proportion of nonionic surfactants. Nonionic surfactants useful for preparation of niosomes include a wide range of compounds that are stable and available in consistent, non-varying forms, for example, sorbitan fatty acid esters, polyethoxylated sorbitan fatty acid esters, omega-alkyl-bis-(1-aza-18-crown-8) compounds (Bola-surfactants), alcohol ethoxylates formed from the addition of ethylene oxide to fatty alcohols, glyceryl and polyglyceryl fatty acid esters, and saccharide and polysaccharide fatty acid esters. On the other hand, phospholipids, which are required in large amounts for non-niosome liposomes are complex mixtures of natural products that are subject to variability depending upon source and lot. Furthermore, phospholipids, for example, lecithin are chemically unstable because of oxidation of unsaturated fatty acid residues, and in the form of topically applied medicaments, compositions with relatively large amounts of lecithin may exhibit an undesirable sticky or greasy feel.

A problem with liposomes, niosomes and other nanoparticles is the expense and complexity of synthesis. A very commonly used method of preparation of liposomes and niosomes is thin film hydration in which a mixture of surfactants is dissolved in a volatile solvent, for example, diethyl ether, methylene chloride or chloroform and evaporated to give a thin film on the walls of a flask, which is then rehydrated with an aqueous phase. In order to produce unilamellar vesicles or niosomes, it is typical to shear the rehydrated aqueous suspension by sonication, microfluidization, or repeated filtration through nanoporous filters.

Variability in the synthetic methods and difficulty in scaling from laboratory size equipment, for example, rotary evaporators to large scale production makes widespread commercial use of nanocarrier drug delivery systems, for example, as would be appropriate for over the counter product forms, problematic and unacceptably expensive. Use of nanocarriers for drug delivery has typically been restricted to high value applications.

This invention relates to aqueous compositions useful in the delivery of ibuprofen through biological membranes including skin, blood vessel walls, and mucous membranes. The aqueous compositions include unilamellar lipoleosomes having incorporated therein a pharmacologically active compound, a low HLB surfactant, a polyethoxylated nonionic high HLB surfactant, a water immiscible oil, and optionally cholesterol and/or a phospholipid, for example, lecithin. Unilamellar liposomes which include a weight ratio of water immiscible oil to surfactant greater than 0.12 to one may be termed lipoleosomes.

The HLB values of various surfactants are listed in Table 1. HLB values were calculated using a proprietary algorithm by Molecular Modeling Pro software, version 5.22, commercialized by Norgwyn Montgomery Software Inc, 2003. For compounds for which HLB values could not be calculated using MMP software (hydrophile too small), HLB was calculated using the group contribution method of Davies [J. Davies, "A quantitative kinetic theory of emulsion type, I. Physical chemistry of the emulsifying agent," Gas/Liquid and Liquid/Liquid interface (*Proceedings of the International Congress of Surface Activity* (1957)), pp. 426-38] using group contributions from Akzo Nobel Surface Chemistry LLC Technical Information bulletin "HLB & Emulsification-Description of Hydrophile, Lipophile Balance and use of HLB in Producing Emulsions," Publication SC-11-02, 2011 Akzo Nobel Surface Chemistry LLC.

TABLE 1

HLB Values of Various Surfactants

| Surfactant | HLB value |
|---|---|
| nonylphenol 20 mol ethoxylate | 16.7 |
| polysorbate-80 | 15.0 |
| Polysorbate-81 | 10.2 |
| polysorbate-20 | 16.7 |
| Polysorbate-21 | 12.2 |
| laureth-23 | 17.9 |
| laureth-30 | 18.6 |
| ceteareth-20 | 16.1 |
| ceteareth-30 | 17.6 |
| PEG-7 glyceryl cocoate | 14.3 |
| isotridecyl 9 mol ethoxylate | 13.8 |
| isotridecyl 30 mol ethoxylate | 18.4 |
| nonylphenol 4 mol ethoxylate | 8.6 |
| nonylphenol * | 3.4 |
| lecithin (American Lecithin Alcolec XTRA-A) ‡ | 2.0 |
| sorbitan stearate | 5.7 |
| laureth-3 | 9.2 |
| glyceryl monostearate | 4.7 |
| dimethyl lauryl amine * | 9.8 |
| isotridecyl 3 mol ethoxylate | 8.6 |
| IB = ibuprofen | 3.0 |
| OA = octanoic acid | 4.5 |
| SA = stearic acid | 1.5 |
| oleic acid | 0.9 |
| NAP = naproxen | 3.5 |
| myristic acid | 2.2 |
| Cholesterol | 0.0 |
| lauryl alcohol | 2.1 |
| cetyl alcohol | 1.3 |

HLB values were calculated using Molecular Modeling Pro software, version 5.22, commercialized by Norgwyn Montgomery Software Inc, 2003 except where noted
* calculated by Davies group contribution method [J. Davies, "A quantitative kinetic theory of emulsion type, I. Physical chemistry of the emulsifying agent," Gas/Liquid and Liquid/Liquid Interface (Proceedings of the International Congress of Surface Activity (1957)), pp. 426-38] using group contributions from Akzo Nobel Surface Chemistry LLC Technical Information bulletin "HLB & Emulsification-Description of Hydrophile, Lipophile Balance and use of HLB in Producing Emulsions," Publication SC-11-02, 2011 Akzo Nobel Surface Chemistry LLC
‡ value from supplier Technical Data Sheet In preferred embodiments, nanoparticles including nanopouches, nanocapsules and lipoleosomes are prepared by decomposing microemulsions occurring at a relatively higher temperature by dilution with water or aqueous compositions, cooling, or both. In preferred embodiments, ibuprofen containing nanoparticles are derived from lamellar phase microemulsions. In a lamellar phase microemulsion, there is near net zero curvature of the interface between water domains and oil domains. As is known, net zero interfacial curvature can be provided by interpenetrating networks which may also be termed sponge phases or isotropic microemulsions in which the two orthogonal Gaussian curvatures of the interface are unequal. In such a microemulsion, points on the interfacial surface may be considered saddle points. Net zero interfacial curvature can also be provided by flat interfacial surfaces. In such lamellar phase microemulsions, points on the interfacial surface are flat and the microemulsion consists of alternating sheets of oil and water domains. In lamellar phase microemulsions, macroscopic optical anisotropy in the microemulsion results when volume elements of microemulsion have different orientations of the sheets which can be observed by viewing through crossed polarizing films, especially while stirring.

It has been known that fine particle size emulsions can be prepared from compositions including polyethoxylated surfactants by processes of phase inversion, including "phase inversion temperature (PIT) emulsification" or "emulsification by PIT." According to PIT emulsification, phase inversion from a relatively higher temperature water in oil (W/O) emulsion to a relatively lower temperature oil in water (O/W) emulsion occurs for polyethoxylated surfactants because the hydrophilicity of such surfactants changes significantly with temperature. Aqueously dispersed particles having diameters less than 150 nm in which an interfacial film layer which is solid at room temperature encapsulates a core that is liquid or semiliquid at room temperature have been termed nanocapsules [Heurtault et al., U.S. Pat. No. 8,057,823]. In the context of the present invention, the term nanopouch is defined particles in which an interfacial film layer which is liquid or semi-sold at room temperature encapsulates a core that is liquid or semiliquid at room temperature.

In particular, polyethoxylated surfactants are characterized by relatively lower values of HLB (greater hydrophobicity) at higher temperatures. According to Bancroft's rule, which states that the continuous phase is the phase in which the surfactant has the greatest solubility, cooling emulsions with polyethoxylated surfactants to increase the hydrophilicity of the surfactant is capable to result in phase inversion, in which water transitions from being the internal, discontinuous phase to the continuous phase while oil becomes the dispersed phase. The increased hydrophilicity of polyethoxylated surfactants at lower temperatures is the result of hydration of the polyethoxylate ether oxygen atoms, which are otherwise relatively more hydrophobic, as for example, in dialkyl ether compounds.

Besides the hydrophilcity of the surfactant, the type of emulsion formed depends on several other factors. Typically, when the volume fraction of one phase is very small compared with the other, the phase that has the smaller fraction is the dispersed phase and the other is the continuous phase. Addition of water or aqueous compositions to mixtures of oils and surfactants gives phase inversion at constant temperature as reported, for example, by Forgiarini et al., Langmuir, 2001.17 (7), 2076-2083. DOI: 10.1021/la001362n. According to Forgiarini et al., the addition of water to a mixture of non-ionic surfactant plus oil gave fine particle size nanoemulsions through a process of inversion without temperature change and without high shear mixing.

In some cases, a system of oil, water and surfactants including polyethoxylated surfactants will not only "invert" as the temperature or composition changes, but will also exhibit intermediate phases including lamellar phases and microemulsion phases. For example, in a PIT emulsification system, a microemulsion phase may exist at temperatures in between the onset and completion of the phase inversion.

Microemulsion formation in the presence of immiscible oil and water phases can be seen as analogous to micelle formation, which occurs in a single-phase aqueous system. Surfactants in a single-phase aqueous system will dissolve at low concentrations to give dissolved monomer in equilibrium with surfactant assembled at surfaces including the air-water interface and the water-vessel interface. As more surfactant is added to the solution, the available interfacial area becomes increasingly populated with surfactant, and when the water is saturated with surfactant monomer and the interfacial area is completely populated (saturated) with surfactant, the surface tension reaches a minimum and remains constant with further surfactant addition. At the point at which the surface tension plateaus, known as the critical micelle concentration, the surfactant no longer has unpopulated interfacial area on which to assemble, and the system responds by creating additional interfacial area through the assembly of surfactant into micelles.

By comparison, in a two-phase oil and water system, as the surfactant reaches saturation, instead of creating interfacial area by assembling into micelles, the system may respond by generating interfacial area as a boundary layer between oil and water domains, in which case a microemulsion may form. Micro emulsions can occur at conditions where the surfactant is pushed to create interfacial area as a result of having limited solubility in both oi and water. Depending upon the nature of the oil and surfactants, the temperature range of phase inversion onset and completion is where such solubility conditions exist. If a microemulsion occurs by assembly of surfactant compounds into a boundary layer in the temperature region of phase inversion, it is understood to be thermodynamically stable.

It is possible that the high interfacial area created by self-assembly processes in the formation of a microemulsion can be captured to a significant degree by changing system conditions from the point of thermodynamic equilibrium to conditions where an oil in water emulsion is metastable.

Oil in water emulsions prepared by PIT emulsification and high shear processes are known to be metastable with respect to phase separated oil and aqueous phases. Spontaneous decomposition of oil in water emulsions by processes including coalescence and Ostwald ripening may occur so slowly, however, that emulsions can be quite stable, providing acceptably long shelf lives for products containing them. Such stability may be termed kinetic stability or metastability. It is known that coalescence of oil in water emulsions accelerates as system conditions approach phase inversion. It is preferable that compositions prepared by PIT emulsification have a phase inversion point at temperatures greater than about 60° C. and more preferably above about 70° C. or about 80° C.

Previously it has been shown that oil in water emulsions containing ibuprofen can be prepared by phase inversion methods. For example, PIT emulsification of compositions including ibuprofen was reported by Formiga et al., influence of a lipophilic drug on the stability of emulsions: an important approach on the development of lipidic carriers. *Int J Pharm*. 2007 Nov. 1; 344(1-2):158-60. Ibuprofen containing nanocapsules with particle sizes below 150 nm have also been prepared by temperature driven phase inversion of compositions including poly(ethylene glycol) hydroxystearate by Lamprecht et al., lipid nanocarriers as drug delivery system for ibuprofen in pain treatment *J Pharm*. 2004 Jul. 8; 278(2):407-14 and Abdel-Mottaleb et al., Lipid nanocapsules for dermal application: a comparative study of lipid-based versus polymer-based nanocarriers. *Eur J Pharm Biopharm*. 2011 September; 79(1):36-42. Doi: 10.1016/j.ejpb.2011.04.009). Nanoemulsions were prepared through addition of water to oil plus ibuprofen plus surfactant mixtures by Salim et al., Phase Behavior, Formation and Characterization of Palm-Based Esters Nanoemulsion Formulation containing Ibuprofen, *Journal of Nanomedicine and Nanotechnology*, 2:113 (2011), DOI:10.4172/2157-7439.1000113.

Recently it has been shown by Lee et al., Langmuir, 2014, Sep. 18; 30(3):1082-33. DOI: 10.1021/la502207f, that decomposition of microemulsion phases can also give oil in water dispersions in which the dispersed phase includes niosomes. Rapid dilution with water and cooling of micro emulsions consisting of nonylphenol, nonylphenol polyethoxylates, hexadecane, and water gave dispersions in which the dispersed oil phase was observed to be vesicular by cryo-TEM.

The process of emulsification described by Lee et al. is a subset of phase inversion processes, for example, PIT emulsification in that it requires a microemulsion phase and that it gives liposomal dispersoids. It was reported that by omitting nonylphenol cosurfactant from the system, an intermediate microemulsion is not obtained, and the dispersion resulting from rapid dilution and cooling is a cloudy emulsion with particle diameter>500 nm. The role of nonylphenol cosurfactant in Lee et al.'s system was to promote microemulsion formation, and it appears that microemulsion formation is in turn related to generation of lamellar structures. The addition of nonylphenol cosurfactant in Lee et al.'s system simultaneously promoted both microemulsion formation and lamellar structure development.

It was further shown by Lee et al. That the extensiveness of lamellae formation in the microemulsion precursor determines the quality of the vesicular dispersion resulting from decomposition. Although micro emulsions containing relatively lower concentrations of nonylphenol were described as most likely being bicontinuous on the basis of freeze fracture cryo-SEM, there was also evidence for lamellae on the basis of slightly depressed electrical conductivity (the percolative pathway through the system has not yet become highly torturous) and the fact that the rate of decrease in electrical conductivity per nonylphenol addition is at a maximum at the point of relatively lower nonylphenol content (the percolative pathway is rapidly becoming torturous due to the presence of non-conducting sheets). Decomposition of the relatively less extensive lamellar systems derived from adding the minimal amount of nonylphenol required for a microemulsion gave small, unilamellar vesicles whereas decomposition of micro emulsions with more nonylphenol gave much larger multilamellar vesicles.

Nanoparticles are formed from lamellar phase microemulsions when flat sheets of oil sandwiched between two surfactant films and alternately stacked with flat sheets of water change shape as a result of hydration. The sandwiched sheets of oil can also be visualized as oil swollen, flat lipid bilayers. In the process of hydration, hydrophilic groups in the surfactant films become relatively more hydrated and become enlarged, creating an imbalance in the volume of hydrophilic surfactant "head" to hydrophobic surfactant "tail." Geometrically, as the hydrophilic surfactant heads become larger than the hydrophobic tails, the boundary between oil and water domains must curve away from water and towards oil. Small imbalances in size can be accommodated by bending of the oil swollen lipid bilayers and opening up of pores in the layer, but large size imbalances result in decomposition of layers to give particles dispersed in water. As particles, the sum of al the interfacial curvatures of surfactant films in the system can be strongly in the direction of oil. Larger imbalances in the size of all hydrophilic heads to all hydrophobic tails in the system result in greater curvature of the surfactant layers and overall smaller particles. In preferred embodiments, ibuprofen containing nanoparticles have small particle sizes, less than 200 nm.

Changes of flat oil swollen lipid bilayers in lamellar phase microemulsions resulting from hydration can occur in such a way as to give differently shaped dispersed particles. Lamellae can blister and tear to give vesicular structures which may be single or multiple layers. Alternatively, pores in lamellae can assemble and expand to separate the lipid layer into individual particles which may initially remain relatively non-spherical but subsequently re-shape to give spherical particles consisting of oil surrounded by an interfacial surfactant film. Such spherical particles have alternatively been called oil swollen micelles, filled emulsion droplets, nanoemulsion droplets, nanocapsules, and in the case that the oil is sold or semi-solid, solid lipid nanoparticles (SLNs) and nanostructured lipid nanocarriers (NLCs), respectively.

Hydration of hydrophilic groups in surfactant films which drives changes in geometry is most impactful for films which include surfactants that include poly(ethylene glycol) (PEG) groups. Surfactants, surfactant films, surfactant bilayers, microemulsion lamellae, and particles which include PEG groups have been referred to as PEGylated. The degree of hydration of PEG groups in surfactants, surfactant films, surfactant bilayers, microemulsion lamellae, and particles is easily adjusted by changing the temperature. At relatively higher temperatures, hydrogen bonding between water and ether oxygens in PEG groups is disrupted, resulting in dehydration while at lower temperatures, hydrogen bonding occurs and both the hydrophilicity and size of PEG groups increase. Decomposition of microemulsion lamellae to give particles therefore can result simply from cooling. Disruption of hydrogen bonding and dehydration of PEG groups can also result from the presence chemical compounds known as kosmotropes such as glycerin, diglycerol, triglycerol, sugars, trehalose, lactic acid, maleic acid, tartaric acid, citric acid, ascorbic acid and phosphate, sulfate, and hydrogen phosphate salts. Decomposition of microemulsion lamellae can result from dilution of microemulsions that contain kosmotropes.

It may be surmised from Lee's measurements of electrical conductivity that nonylphenol increases the both the extensively and rigidity of lamellar structures in systems including water, oil, and surfactants. Although nonylphenol and nonylphenol ethoxylate compounds are useful to provide lamellar phase microemulsions capable to be hydrated to give liposomes, they are unacceptable in pharmacological and personal care products because of the hormone mimetic properties of nonylphenol. Preferable lamellar phase microemulsions and derivative liposomal dispersions are essentially nonylphenol free and contain less than 500 ppm of nonylphenol. It has been found that addition of ibuprofen, like addition of nonylphenol, increases rigidity in lamellar structures, as evidenced by decreased electrical conductivity of micro emulsions.

Summarizing the work of Lee et al., it can be concluded that properties of polyethylene glycol surfactant based lamellar phase microemulsions can be modified by cosurfactant addition so as to change the shape of nanoparticles derived from hydrative decomposition. In hydrative decomposition of lamellar phase microemulsions, the net interfacial curvature changes from zero to concave towards oil as a result of an increase in size of PEG groups in surfactants as a result of hydration. In such synthesis of nanoparticles, cosurfactant addition changes product nanoparticle geometry by altering the nanomechanical properties in precursor lamellar phase microemulsions. For example, more rigid and less tearable lamellae in microemulsions hydrate to give large multilamellar nanoparticles, soft lamellae hydrate to give filled particles, and lamellae with intermediate rigidity and tearability hydrate to give small unilamellar vesicles. By moderating the properties of lamellar phase microemulsions by changing surfactants, it is possible to control the product of hydration.

Previously it has been suggested that nanomechanical properties of surfactants in nanocapsules are important for encapsulation of chemical compounds within the particle. For example, it has been proposed by Heurtault et al. that films of surfactants that are solid at room temperature are effective to encapsulate active pharmaceutical compounds within nanoparticles (U.S. Pat. No. 8,057,823). Consequently, it might be expected that by modifying the mechanical properties, i.e. Solid vs. liquid, of the mixture of surfactants in nanoparticles, that it is possible to modify the capability of nanoparticles to effectively encapsulate compounds. Consequently, it might also be expected that nanoparticles derived from hydration of relatively stiffer lamellar phase microemulsions would have better barrier properties.

It has been found however that encapsulation efficiency of ibuprofen in nanoparticles is more strongly dependent upon chemical rather than mechanical properties of surfactant films. Some surfactant compositions in which all of the individual surfactants are liquids at room temperature provided much better encapsulation of ibuprofen than the solid surfactant films described by Lamprecht et al. and Abdel-Mottaleb et al. Surfactant compositions in which al of the individual surfactants are liquids at room temperature also may provide better encapsulation than surfactant compositions in which all of the surfactants were solids. It is also remarkable that in some cases surfactants with very similar HLB values and behavior in promoting lamellae stiffness in microemulsions provide very different capabilities to encapsulate of ibuprofen. For example, in nanocapsule dispersions with ibuprofen, isopropyl myristate, ceteareth-20 and maltodextrin, using sorbitan stearate or sorbitan oleate as cosurfactants retards crystallization of ibuprofen for by a factor of six relative to identical compositions having glyceryl stearate as the cosurfactant.

It is important that rigidity in surfactant films including surfactant monolayers and surfactant bilayer structures be controlled. Preferable product nanoparticles have flexible surfactant monolayers or bilayer membranes so as to maximize penetration into the skin. It has been previously described to decrease rigidity in pharmaceutical nanovesicles for topical administration. According to Cevc et al. (U.S. Pat. No. 7,473,432), highly adaptability (via ability to deform, measured as ability to pass through a semi-permeable barrier) in aggregates, for example, vesicles is advantageous for transport through semi-permeable mammalian skin and can result from destabilization of lipid membranes by surfactants including salts of NSAID compounds. Cevc et al. have also noted that mixed lipid vesicles with a highly flexible/fluid membrane are better skin penetrants than much smaller mixed lipid micelles (Cevc et al., *Biochimica et Biophysica Acta,* 1584 (2002) 21-30). Rigidity in microemulsion lamellar structures can be monitored and controlled using electrical conductivity measurements. Other authors have also reported that increasing the flexibility of lipid bilayers in vesicular nanoparticles increases skin permeation.

Preferably, the electrical conductivity of higher temperature microemulsion precursors to nanoparticles is not too greatly depressed relative to the conductivity of final oil in water dispersions (overall conductivities of phases being greatly variable due to the relative presence or absence of ions). In preferred embodiments, the maximum conductivity measured in the microemulsion temperature region of nanoparticle precursor compositions are between about 10% and about 100%, between about 25% and about 99%, and between about 50% and about 95% of the maximum conductivity of the undiluted system measured between about 0° C. and about 100° C.

While the requirement for a pharmacologically meaningful concentration of weakly amphipathic pharmacologically active compound, for example, ibuprofen promotes rigidity and extensiveness of lamellar phases to the point that decomposition of micro emulsions to unilamellar vesicles or the flexibility and penetration of vesicles becomes unacceptable, it has been discovered that rigidity may be offset by careful formulation.

Using minimal amounts of bilayer rigidizing compounds, for example, phospholipids including lecithin and cholesterol and using high HLB surfactants with relatively long ethoxylate chains can allow sufficiently weak and non-extensive micro emulsions as indicated by electrical conductivity measurements. Such conductive micro emulsions are useful precursors to small nanoparticles with flexible surfactant monolayers or bilayers. Furthermore, the flexibility of product lipoleosome can be moderated by the varying the amount of low HLB, lamellae rigidizing compounds.

In preferred embodiments, the concentration of lecithin per non-volatile content of the nanoparticle composition is less than about 50%, less than about 30%, and less than about 20%. In preferred embodiments, the concentration of phospholipid compounds per non-volatile content of the nanoparticle composition is less than about 50%, less than about 30%, and less than about 20%. In preferred embodiments, the concentration of elemental phosphorous is less than about 30 mg per gram of non-volatile content of the nanoparticle composition, less than about 16 mg per gram of non-volatile content of the nanoparticle composition, and less than about 12 mg per gram of non-volatile content of the nanoparticle composition. In preferred embodiments, the concentration of phospholipid compounds in nanoparticle dispersions is less than 3 weight percent. In preferred embodiments, the concentration of phospholipid compounds in nanoparticle dispersions is less than 1 weight percent. In preferred embodiments, the concentration of cholesterol per non-volatile content of the lipoleosomal composition is less than about 30%, less than about 20%, and less than about 10%. In preferred embodiments, compositions include ethoxylated surfactants or mixtures of ethoxylated compounds with number average ethoxylate chain length between about 25 and about 100 ethoxylate groups, between about 30 and about 45 ethoxylate groups, between about 30 and about 35 ethoxylate groups.

The extent of lamellar character in micro emulsions and the degree of flexibility of the surfactant monolayer and bilayer membranes in nanoparticles can also be addressed by choice of water immiscible oil. The choice of water immiscible oil determines the partitioning of the weakly amphipathic pharmacologically active compound between the bulk oil phase and the oil-water interfacial membrane. A useful strategy for controlling the rigidity of surfactant monolayer and bilayer membranes in nanoparticles as well as the phase inversion temperature and the temperature range in which micro emulsions occur is to vary the solubility of weakly amphipathic compounds in the oil phase by varying the composition of the oil phase.

In preferred embodiments, the water immiscible oil is selected also on the basis of being capable to promote permeation through skin. For example, numerous sources have reported that isopropyl myristate supports high transdermal fluxes. Panigrahi et al., *American Association of Pharmaceutical Scientists PharmSciTech,* 6(2): E167-73 (2005), reported that isopropyl myristate gives a pronounced flux enhancing effect for terbutaline sulfate compared to methyl laureate and isopropyl lanolate, which was attributed to solubility parameter of isopropyl myristate being closer to the solubility parameter of human skin. The permeability of alpha tocopherol through human cadaver skin was about 20 to about 100 times greater for an isopropyl myristate solution compared to ethanol solution, light mineral oil solution, or hydroxypropyl cellulose gel (Mahamongkol et al., *J. Cosmet. Sci.,* 56 (2): 91-103 (2005)).

The flux of niosomes across membranes is also a function of the size of the niosomes relative to intercellular pore sizes. It is estimated that the average width of pathways through the skin is about 20-40 nm, and for flexible liposomes useful fluxes have been observed for ratios of liposome diameter to pore diameter of up to about 6 (Cevc et al., *Biochimica et Biophysica Acta,* 1564 (2002) 21-30). Preferred volume average particle size of the nanoparticle dispersions of the present invention are less than about 240 nm, less than about 170 nm, and less than about 120 nm. The permeability of nanocapsules is also dependent upon particle size and ibuprofen containing nanocapsules with 51 nm particle size support higher dermal permeability than particles with 289 nm particle size (Abdel-Mottaleb et al., Lipid nanocapsules for dermal application: a comparative study of lipid-based versus polymer-based nanocarriers. Eur J Pharm Biopharm. 2011 September; 79(1):36-42). Preferable nanocapsules and nanopouches have volume average particle size of the nanoparticle dispersions below 150 nm, below 100 nm, and below 50 nm. In general, ibuprofen nanoparticles of the present invention have volume average particle size of the nanoparticle dispersion less than 240 nm. Preferred ibuprofen nanoparticles of the present invention have volume average particle size of the nanoparticle dispersion less than 240 nm, less than 170 nm, less than 150 nm, less than 120 nm, less than 100 nm, and less than 50 nm. In preferred embodiments, the particle size of nanopouch, nanocapsule and lipoleosomal compositions are measured by dynamic light scattering, for example, using a Malvern Zetasizer, a Brookhaven Instruments ZetaPALS DLS instrument, a Beckman Coulter Delsa Nano particle size analyzer, or a Microtrac NanoFlex DLS Particle Analyzer.

Nanoparticles with surfactant films that include saccharide residues have been found to be particularly effective for encapsulating ibuprofen. A particularly preferred saccharide residue is sorbitan, which is derived from dehydration of sorbitol (Equation 1). Sorbitan residues provide a barrier property for surfactant films in nanoparticles that contain ibuprofen when they are incorporated into either hydrophobic low HLB surfactants or hydrophilic high HLB surfactants. In preferred embodiments, surfactant films in ibuprofen containing nanoparticles include a low HLB sorbitan ester. In preferred embodiments, surfactant films in ibuprofen containing nanoparticles include a low HLB sorbitan ester and a high HLB ethoxylated sorbitan ester. In preferred embodiments, surfactant films in ibuprofen containing nanoparticles include a low HLB sorbitan ester and the nanoparticle dispersion further includes a hydrophilic non-amphipathic polysaccharide compound. In preferred embodiments, surfactant films in ibuprofen containing nanoparticles include a low HLB sorbitan ester and the nanoparticle dispersion further includes maltodextrin. In preferred embodiments, surfactant films in ibuprofen containing nanoparticles include one or more of a low HLB sorbitan ester and a high HLB sorbitan ester and the mole ratio of sorbitan residues to ibuprofen is greater than 0.25 to 1, greater than 0.70 to 1, and greater than 1.0 to 1.

(1)

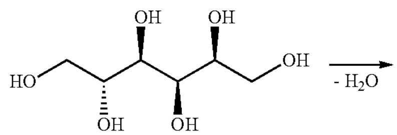

sorbitol sorbitan

In preferred embodiments, ibuprofen containing nanoparticles are nanocapsules. In preferred embodiments, ibuprofen containing nanoparticles are nanopouches. In preferred embodiments, ibuprofen containing nanoparticles are lipoleosomes.

In preferred embodiments, ibuprofen containing nanoparticles are derived from lamellar phase microemulsions. In preferred embodiments, ibuprofen containing nanoparticles are prepared by cooling lamellar phase microemulsions in a process in which the lamellar phase microemulsion is diluted with water. In preferred embodiments, ibuprofen containing nanoparticles are prepared by cooling lamellar phase microemulsions in a process in which the lamellar phase microemulsion is not diluted with water. In preferred embodiments, ibuprofen containing nanoparticles are prepared by diluting lamellar phase microemulsions in an isothermal process in which the lamellar phase microemulsion is diluted with water.

Surfactant films which include compounds with saccharide residues are much more effective at encapsulating ibuprofen in nanoparticles, even in the case that such surfactant films are mostly liquid or entirely liquid.

As a constituent of the water immiscible oil, organic compounds may be included for the purpose of increasing transdermal flux of compositions. Such compounds may in some cases be referred to as rubefacients or "rubefacient essential oils" and include compounds that increase blood flow in dermal capillaries. Compounds useful for increasing transdermal flux include salicylates, for example, methyl salicylate and terpenes, for example, geraniol, d-limonene, camphor, and menthol.

In preferred embodiments, compositions of the present invention include ionic surfactants for the purpose of increasing the flux of nanoparticles across skin. Since the upper layers of skin carry a slight negative surface charge while underlying tissue can carry a much greater negative surface charge (the isoelectric point of the stratum corneum of skin is about 3.7 [Wilkerson, *J. Biol. Chem.*, 1935, 112:329-335], while skin pH is typically in the range of about 4 to about 6 [All, *Acta Derm Venereol*, 2013; 93: 261-267]; mammalian cells have isoelectric points between about 2.1 to about 3.4 [J. Bauer, ed. *Cell Electrophoresis*, 1994, CRC Press] while the human body internal pH is in the range of about 7 to about 9), there can be a pH and surface charge gradient between the stratum corneum and the underlying epidermis, which is effective to promote transdermal flux of nanoparticles. In preferred embodiments of the present invention, nanoparticles have isoelectric points above about pH 4, above about pH 6 and above about pH 7. In preferred embodiments, nanoparticles include a small positive charge measured as zeta potential. The zeta potential is the potential difference between the dispersion medium and the stationary layer of fluid attached to the dispersed nanoparticle surface and is a measurement of the net electrical charge contained within the region bounded by the slipping plane. While relatively higher zeta potential is required for stabilization against coagulation or flocculation in the case of electrostatically stabilized dispersions including as phospholipid-based liposomes, relatively lower zeta potential is acceptable for niosomes, for which stabilization results from repulsion due to thermodynamically disallowed reduction of entropy resulting from overlap of nonionic hydrophilic groups. Low zeta potential as is possible for niosomes facilitates transdermal fluxes to the underlying dermal and subdermal layers. In preferred embodiments, the zeta potential of niosomes that include low $K_{ow}$ pharmacological compounds is between about 0 and about 30 mV, between about 1 and about 20 mV, and between about 3 and about 10 mV.

The zeta potential and net electrostatic charge on nanocarriers can be moderated by the inclusion of anionic surfactants including phospholipids, phosphate esters, sulfates, sulfonates and deprotonated weak acid amphipathic compounds, by inclusion of cationic surfactants, for example, quaternary ammonium salts, or both. In preferred embodiments, compositions include choline carboxylates, amine functional surfactants, or quaternary ammonium surfactants.

In preferred embodiments, compositions of the present invention including unilamellar lipoleosomes can take the form of sprayable low viscosity liquids, isotonic low viscosity aqueous compositions suitable for parental administration, medium viscosity pseudoplastic liquids, Bingham plastic fluids, and solids. By sprayable it is meant that the composition is capable to be sprayed through dispenser by hand, without the need for high pressure, propellants, sonication or air atomization. The rheological properties including viscosity of the products can be provided by varying the water content, by selection of the oil, surfactants and pharmacological compounds, by the addition of viscosity modifying additives, for example, water soluble or water dispersible polymers or inorganic colloids, or by a combination of these methods.

Processes

According to the present invention, oil swollen lamellae in lamellar phase microemulsions are hydrated to give lipophilic nanoparticle dispersions of in water. Useful nanoparticles include small unilamellar liposomes with oil swollen lipid bilayer membranes which may be termed lipoleosomes and oil filled droplets which may be termed nanocapsules or nanopouches. Hydration of microemulsions can be the second step that completes phase inversion processes which begin with a first step of transformation of a water in oil emulsion into a microemulsion. Hydration of the hydrophilic moieties in surfactants that make up lipid bilayers in microemulsions causes them to increase in volume, which creates an imbalance of volumes between the hydrophilic moieties and hydrophobic moieties, resulting in bending stress of the surfactant layer at the interface. In particular, volume expansion of the hydrated hydrophilic layer puts it under a compressive stress relative to the hydrophobic layer which is under tensile stress, resulting in curving of the interfacial surfactant layer away from water. Hydration of surfactant interfacial layers including those in lipid bilayers in microemulsions can occur by adding water to the system and also without adding water if hydrogen bonding interaction between water and the surfactant hydrophilic moieties increases. Hydrogen bonding of water to ether oxygen atoms in poly(ethylene oxide) increases as temperature decreases. In preferred processes to convert lamellar phase microemulsions to small unilamellar liposomes, water is not added to the microemulsion in the hydration step. In preferred embodiments, hydration of lamellae in microemulsion is accomplished by adding water to the microemulsion. Addition of water to surfactant composition results in increased chemical activity of water and dilutes salts and other compounds that disrupt hydrogen bonding, and is effective to increase hydration of both ionic and nonionic surfactant moieties.

Hydration of microemulsions by cooing is the final step in phase inversion temperature (PIT) emulsification and hydration of microemulsions by addition of water is the final step in so-called phase inversion composition (PIC) emulsification. For hydration of microemulsions to proceed so as to produce liposomes with oil swollen lipid bilayers instead of filed nanoemulsion droplets, the presence of oil swollen lipid bilayers (lamellae) in microemulsions is a necessary but not sufficient condition. Both the presence and properties of lamellae in microemulsions are critical for allowing the hydration step to occur so as to preserve lipid bilayers in the product. If the microemulsion lamellae are too flexible and components thereof have high mobility, hydration will give filed emulsion droplets or macroscopic phase separation. If microemulsion lamellae are too rigid and coherent, hydration gives unstable dispersions of large multilamellar liposomes. Features of the hydration process are also of note. For example, imbalance in the extent of hydration on opposite sides of lipid bilayers favors curling, while hydration of both sides favors fragmentation which may lead to the formation of flat disc micelles which deform to give spherical micelles. While not wishing to be bound by theory, it is believed that coordination of the curving and the fragmentation of lipid bilayers are of note for the preservation of the lipid bilayer structure and the formation of liposomes.

Imbalance in hydration of opposite sides of lipid bilayers occurs during dilution when water soluble salts or compounds that disrupt hydrogen bonding are diluted preferentially on one side of the lamella relative to the other. In the relative absence of water-soluble solutes in the aqueous domains of lamellar phase microemulsions, temperature driven imbalance of hydration across the oil swollen lipid bilayer conceptually becomes increasingly of note. Temperature imbalance and large local temperature gradients result from rapid cooling, and therefore relatively more rapid cooling rates are favorable for the formation of liposomes.

In preferred embodiments of the present invention, lamellar phase microemulsions are converted to aqueous dispersions of lipoleosomes, aqueous dispersions of nanopouches and aqueous dispersions of nanocapsules by processes characterized by rapid cooling. In preferred embodiments, microemulsions are converted to aqueous dispersions of lipoleosomes, aqueous dispersions of nanopouches and aqueous dispersions of nanocapsules by rapid isocompositional cooling. In preferred embodiments, microemulsions are converted to aqueous dispersions of lipoleosomes, aqueous dispersions of nanopouches and aqueous dispersions of nanocapsules by both cooling and diluting with water.

In preferred embodiments of the present invention, lamellar phase microemulsions contain water soluble salts or compounds that disrupt hydrogen bonding between water and oxygen atoms in polyethoxylated compounds. Water soluble salts and compounds which disrupt hydrogen bonding between water and oxygen atoms in polyethoxylated compounds may be referred to as kosmotropes. The presence of aqueous solutes that disrupt hydrogen bonding between water and polyethoxylate oxygen atoms increase the apparent hydrophobicity of polyethoxylated surfactants, an effect that is similar to dehydration of polyethoxylate oxygen atoms caused by raising the temperature. A water continuous dispersion or emulsion may be converted to a microemulsion by heating, by disrupting hydrogen bonding by including a kosmotrope, or both. Including a kosmotrope is effective to lower the temperature at which a lamellar phase microemulsion occurs, and in preferred embodiments microemulsions include a kosmotrope. In the presence of relatively large concentrations of kosmotropes, lamellar phase microemulsions exist at room temperature and may be converted to nanoparticle dispersions by isothermal dilution with water. Preferred organic compound kosmotropes include butanol, glycerol, diglycerol, triglycerol, sugars, trehalose, lactic acid, maleic acid, tartaric acid, citric acid and ascorbic acid. Preferred salt kosmotropes include sodium, aluminum, calcium, ammonium, and potassium and magnesium salts of phosphate, sulfate, and hydrogen phosphate ions.

In preferred embodiments of the present invention, lamellar phase microemulsions are converted to nanoparticle dispersions in isothermal processes, in analogy to the phase change processes that give nanoemulsions such as described by A. Forgiarini et al., "Formation of Nano-emulsions by Low-Energy Emulsification Methods at Constant Temperature," *Langmuir,* 2001, 17 (7), 2076-2083) and the method of producing finely divided oil-in-water emulsions described by J. Meyer et al. in United States Patent Application Publication No. 20080004357.

Figure 2:
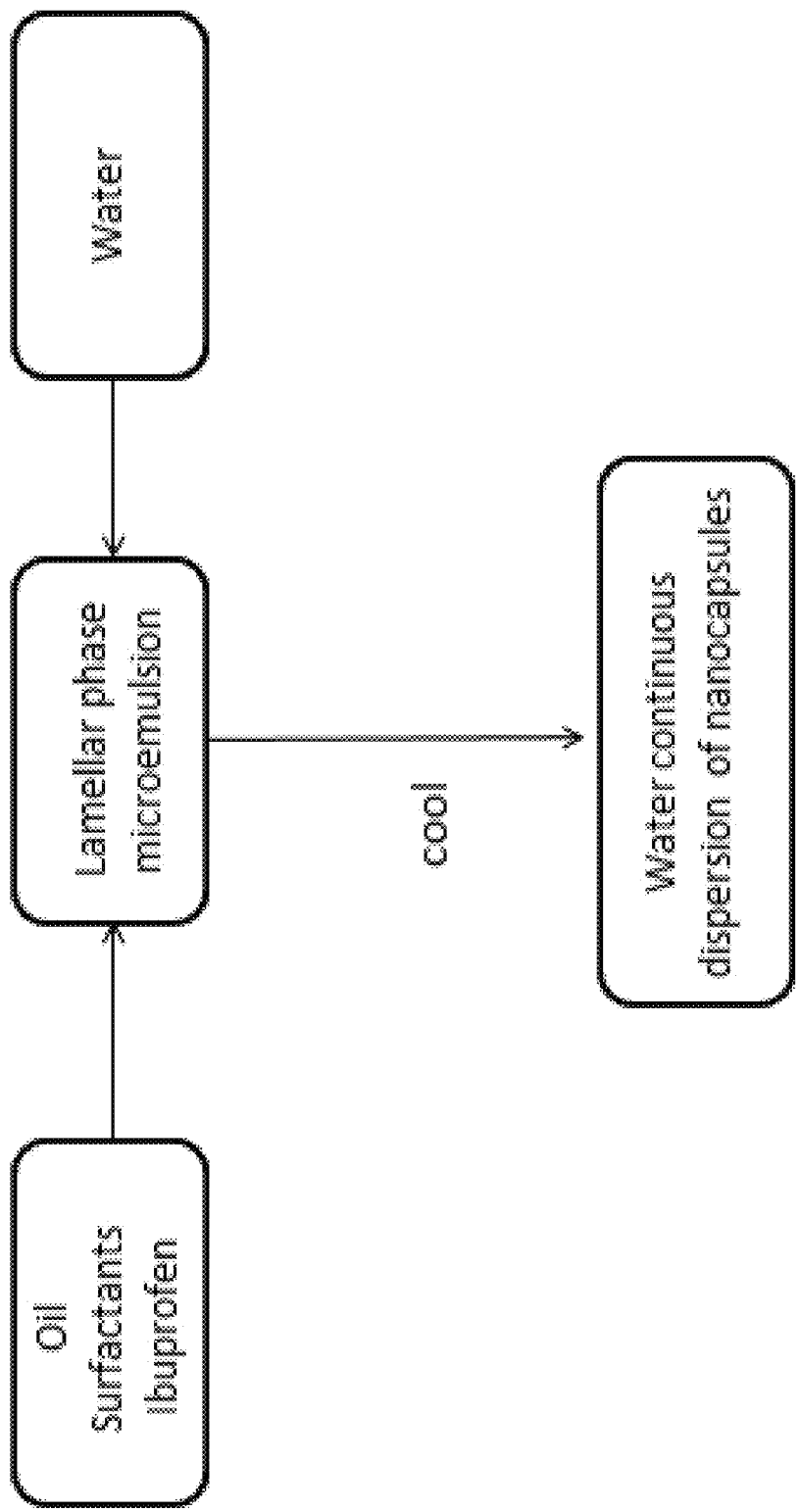
Figure 3:
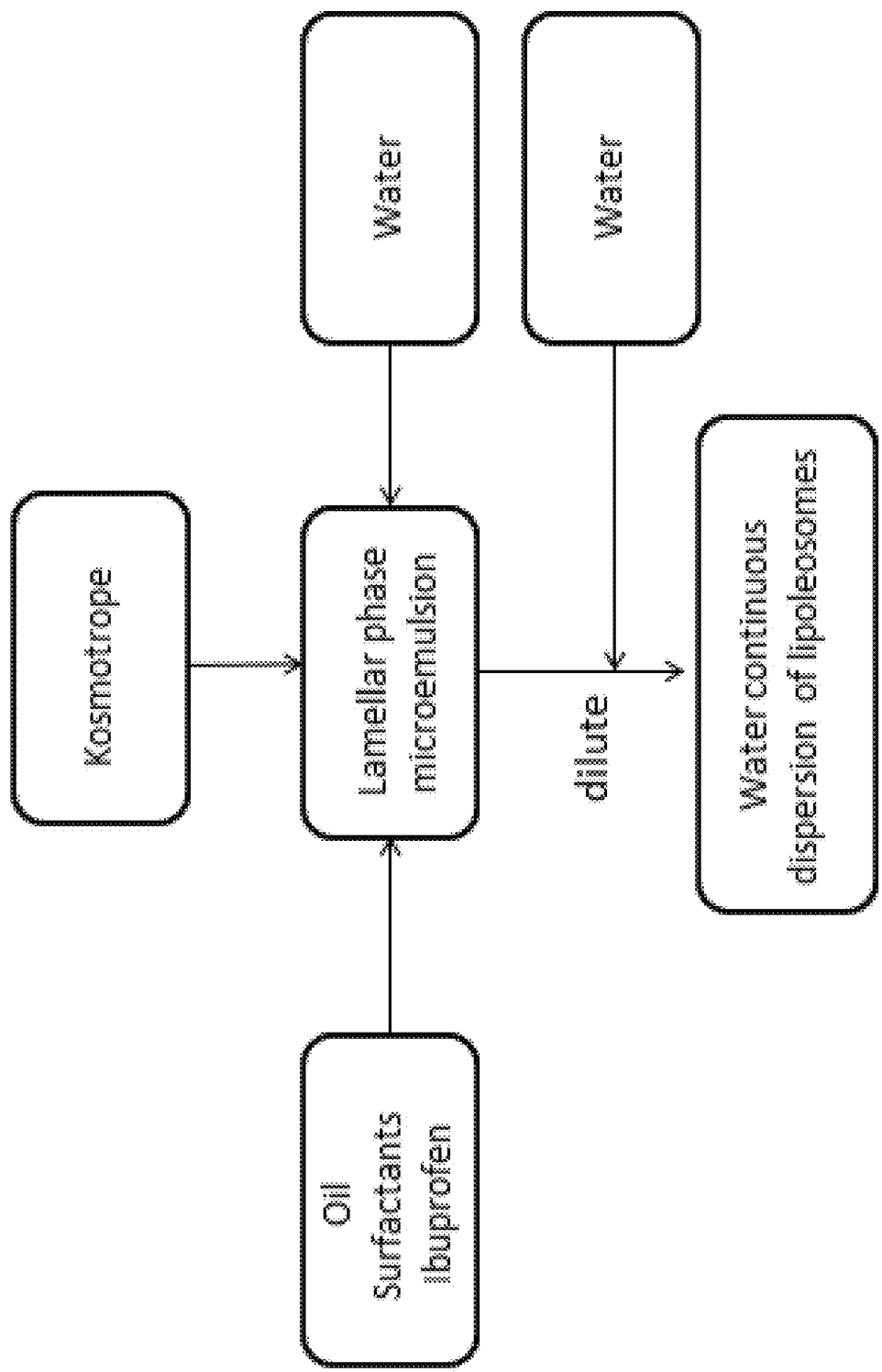
Figure 4:
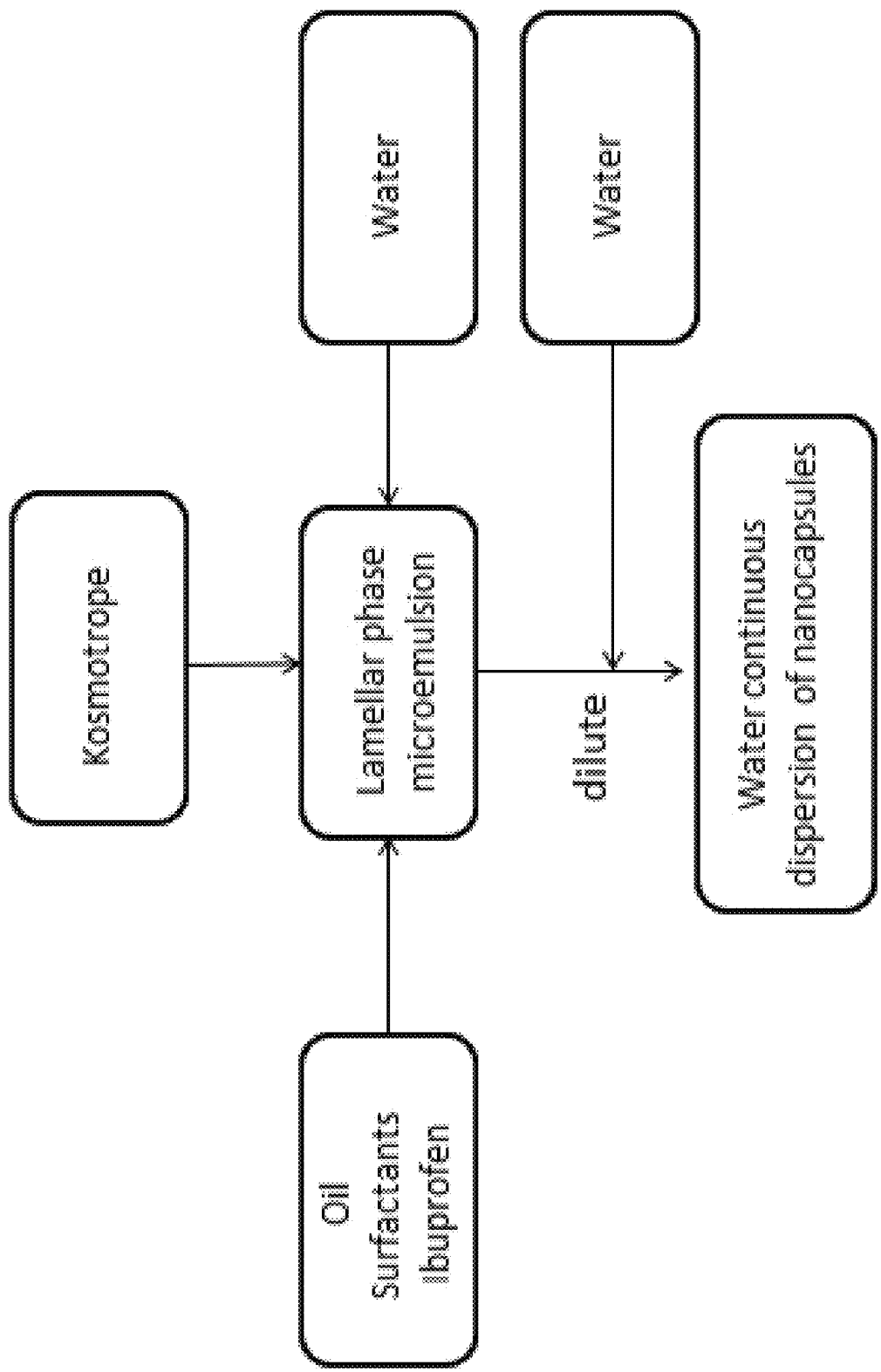

In preferred embodiments of the present invention, lipoleosome dispersions are prepared by a process as shown in FIG. 1.
  1. Preparation a lamellar microemulsion including water, oil, and surfactants
  2. Cooling of the microemulsion In preferred embodiments of the present invention, nanocapsule or nanopouch dispersions are prepared by a process as shown in FIG. 2.
  1. Preparation a lamellar microemulsion including water, oil, and surfactants
  2. Cooling of the microemulsion In preferred embodiments of the present invention, lipoleosome dispersions are prepared by a process as shown in FIG. 3.
  1. Preparation of a lamellar microemulsion including water, oil, kosmotropes and surfactants
  2. Dilution of the microemulsion In preferred embodiments of the present invention, nanocapsule or nanopouch dispersions are prepared by a process as shown in FIG. 4.
  1. Preparation of a lamellar microemulsion including water, oil, kosmotropes and surfactants
  2. Dilution of the microemulsion In preferred embodiments of the present invention, lipoleosome dispersions are prepared by a process of:
  1. Preparation of a lamellar microemulsion including water, oil, kosmotropes and surfactants
  2. Cooling of the microemulsion In preferred embodiments of the present invention, lipoleosome dispersions are prepared by a process of:
  1. Preparation a lamellar microemulsion including water, oil, kosmotropes and surfactants
  2. Dilution of the microemulsion In preferred embodiments of the present invention, nanopouch or nanocapsule dispersions are prepared by a process of:
  1. Preparation a lamellar microemulsion including water, oil, kosmotropes and surfactants
  2. Cooling of the microemulsion Compositions Compositions of the present invention generally include ibuprofen, a water immiscible oi, a low HLB surfactant, a polyethoxylated high HLB surfactant, at least one compound that includes a saccharide residue, water, and optionally may contain a non-ethoxylated high HLB surfactant and additional components.

Ibuprofen

An important feature of aqueous dispersions of nanoparticle carriers for ibuprofen is effective containment of ibuprofen within the carrier. Inability to adequately encase ibuprofen results in formation of crystals and loss of bioavailability. Avoidance of crystallization in dispersed systems becomes more difficult as the crystal lattice energy and melting point of an encapsulated compound increase and as solubility in lipids decreases. As the differential between chemical potential of ibuprofen in nanoparticles and crystals increases, the thermodynamic driving force for diffusion also increases.

Migration of ibuprofen from nanoparticles to crystals is analogous to the migration of hydrophobic compounds from smaller to larger emulsion droplets and migration of monomers in emulsion polymerization. Such migrations are examples of ripening processes where molecules move from one dispersed particle to different dispersed particle in which potential energy is lower. Ripening processes in aqueous media occur for migrating species that have water solubility of the in the range of about 10 to about 1000 mg/L. With pH dependent solubility ranging from 20 to 230 mg/L at pH values from 1.0 to 6.0, ibuprofen has water solubility ideal for ripening to produces crystals. In ripening of dispersions including ibuprofen, ripening produces crystals of ibuprofen. As ripening processes favor migration from relatively smaller particles compared to relatively larger particles, it can be readily appreciated that the problem of outward migration of ibuprofen from nanoparticles intensifies as particle size decreases. Sequestration of ibuprofen in nanoparticles is more difficult than for larger particles such as those prepared by conventional emulsification processes.

One concept for minimizing formation of crystals in ibuprofen dispersions and emulsions is to minimize solubility by lowering pH. However, within the range that is practical for commercial products this approach is not capable of significantly retard crystallization.

Another approach for minimizing the problem of crystallization of ibuprofen is to neutralize the lipophilic free acid with bases to give ibuprofen salts such as ibuprofen sodium in compositions with pH greater than 8. However, the sodium salt of ibuprofen skin permeability which is four times lower than an equivalent concentration of the neutral compound. Besides the disadvantage of lower intrinsic permeability through skin, the water-soluble sodium sat of ibuprofen is more easily cleared from the location of application by the circulatory system. In ibuprofen compositions of the present invention, the pH is preferably sufficiently low that ibuprofen is substantially present as the unneutralized free acid, in which case the pH of the composition is one pH unit or more below the apparent pKa value of ibuprofen. The apparent pKa value of ibuprofen in nanoparticle encapsulated dispersions is greater than that reported for ibuprofen (between 4.9 and 5.2) because ionization is governed by both partitioning of free acid and ionized forms between nanoparticle and water and acidity of the molecule, Preferable pH values for compositions of the present invention in which ibuprofen is substantially present as the free acid form are less than 6.5, less than 5.5, and less than 5. In the preferred embodiments, the ratio of equivalents of acid determined by titration with sodium hydroxide to moles of ibuprofen in the composition is greater than 0.8 to 1, greater than 0.9 to 1, and greater than 0.95 to 1.

The challenge of effectively encapsulating ibuprofen in dispersed lipid nanoparticles is increased in the case that ibuprofen is provided as a racemic mixture. The two ibuprofen enantiomers co-crystalize to give a solid with a higher crystal lattice energy, higher heat of fusion, higher melting point, and lower chemical potential than either enantiomer individually. The heat of fusion and meting point for the racemic mixture are 75° C. and 125 J/g, respectively compared to 52° C. and 91 J/g for S-(+)-ibuprofen. In preferred embodiments, there is an enantiomeric excess of the pharmacologically more active S-(+)-ibuprofen of greater than 80%, greater than 90% and greater than 95%.

One approach to retard crystallization in ibuprofen containing nanoparticle dispersions is to maximize solubilization of ibuprofen in the nanoparticle. For example, for an emulsion of ibuprofen dissolved in oil, the oil may be chosen on the basis of capability to dissolve ibuprofen. Unfortunately, the bulk solubility of ibuprofen in water immiscible oils is impractically low and decreases below room temperature. Ibuprofen is known to have high solubility in a number of polar and amphipathic liquids as described in U.S. Patent Application Publication No. 20080075787 (Ibuprofen-containing liquid fled hard capsules, Jin et al.), but solubility in these liquids is greatly reduced by the presence of water. For example, the solubility of ibuprofen in PEG 400 is 1.2 M (approximately 25 weight percent (%)) but drops to 0.55 M (approximately 11 weight percent (%)) when PEG ether oxygens are hydrated with 0.7 moles of water per ether oxygen (PEG400/water=75:25 by volume) and drops to 0.014 M (approximately 0.3 weight percent (%)) when PEG ether oxygens hydrated with 2.2 moles of water per ether oxygen (PEG400/water=50:50 by volume).

Another concept for minimizing crystallization of ibuprofen in aqueous nanoparticle dispersions is encapsulation. U.S. Pat. No. 8,057,823 (Heurtault et al., Lipid nanocapsules, preparation process and use as medicine) describes encapsulation of drugs in lipid nanocapsules consisting of a liquid or semiliquid lipid core coated with a lipid film that is solid at room temperature. Subsequent researchers have investigated the encapsulation of ibuprofen in nanocapsules prepared as described by Heurtault et al. [Lamprecht A, Saumet J, Roux J, Benoit J. Lipid nanocarriers as drug delivery system for ibuprofen in pain treatment. *Int J Pharm.* 2004 Jul. 8; 278(2):407-14]. However, the poly(ethylene glycol) hydroxystearate coating provides little impedance to the migration of ibuprofen, and crystallization occurs rapidly in such nanocapsule dispersions during storage below room temperature.

Water Immiscible Oils

Useful oils are low volatility water immiscible compounds or mixtures of compounds that are liquid at 20° C. Preferably, oils have sufficiently low volatility so as to provide liposomal compositions that are not flammable and that can be safely manufactured. Fire hazards are reduced if processing is done at temperatures below the flash point of microemulsions. In a preferred process, the single compound or mixture of compounds that makes up the oil has a flash point above the formation temperature of the microemulsion, and more preferably above the boiling point of water. Preferred oils, whether a single compound or mixture of compounds, have flash points above about 75° C., above about 100° C., and above about 125° C. Volatile oils which themselves have unacceptably low flash points can be included so long as they are blended with less volatile oils and the flash point of the oil blend is above about 75° C., above about 100° C., or more preferably above about 125° C.

Preferred oils support the formation of lamellae in microemulsion that are precursors to lipoleosomes, nanopouches and nanocapsules. The lamellar character of microemulsions depends upon properties of oil as well as surfactants and composition ranges. The propensity of oil-water-surfactant compositions towards lamellar character increases with decreasing oil molecular weight and increasing oil polarity. In preferred embodiments, the molecular weight of oil (taken as the weight average molecular weight in the case of mixtures of compounds) is sufficiently low that lamellae formation occurs, but is sufficiently large so as to provide low volatility and low flash points. In preferred embodiments, the molecular weight of oil is less than about 900 g/mol, less than about 700 g/mol, and less than about 550 g/mol. In preferred embodiments, the weight average molecular weight of individual water insoluble compounds in oil is less than about 900 g/mol, less than about 700 g/mol, and less than about 550 g/mol. In preferred embodiments, water miscible oils can be used interchangeably or provided as mixtures. In preferred embodiments, the water miscible oil or mixture of oils is selected so as to control partitioning of ibuprofen to the surfactant monolayer or bilayer and moderate rigidity of the surfactant monolayer or bilayer in nanoparticles.

Preferred oils include, for example, terpenoid compounds, defined as natural compounds derived from isoprene units and containing multiples of five carbon atoms, including oxygenated compounds. Exemplary terpenoid compounds are cyclic and acyclic and include limonene, menthol, carvone, pinene, camphor, cineole, linalool, citronellol, geraniol, and patchoulol. Terpenoid compounds may be added to liposomal compositions as discrete compounds or as an extracted mixture from plants called essential oils. Preferred oils include essential oils extracted from plants such as thyme essential oil and eucalyptus essential oil. Preferred liposomal compositions include fragrant hydrophobic compounds including both terpenoid and non-terpenoid compounds. In preferred embodiments, liposomal compositions include greater than about 500 ppm by weight of hydrophobic organic compounds with odor thresholds less than about 500 parts per billon by volume. In preferred embodiments, the non-water ingredients of liposomal compositions include greater than about 0.1 percent, greater than about 0.5 percent, and greater than about 1.0 percent by weight of hydrophobic organic compounds with odor thresholds less than about 500 parts per billion by volume. Useful fragrant hydrophobic organic compounds include esters, for example, ethyl butanoate, octyl acetate, and isoamyl acetate; lactones, for example, γ-nonalactone and γ-decalactone; aromatics, for example, cinnamaldehyde, eugenol, anisole, and vanillin; aldehydes, for example, benzaldehyde and hexanal; and ketones, for example, undecanone. In preferred embodiments, hydrophobic fragrance compounds in liposomal compositions exist within the liposome lipid bilayer. When lamellar phase microemulsion compositions include fragrance compounds including terpenoids, it is preferred that flash point of the oil remains above about 75° C., above about 100° C., and above about 125° C. and the ratio of oil to surfactant remains between about 0.12:1 to about 3.5:1, between about 0.24:1 to about 2.5:1, and between about 0.48:1 to about 2.0:1.

Suitable water immiscible oils include:

(1) Hydrocarbons, for example, mineral oil, isoparaffin, isohexadecane, poly(alpha olefins), squalane and squalene, hydrogenated oligomers of propene, butane, and isobutylene, cycloaliphatic compounds, and alkylated aromatic compounds, for example, alkylated naphthalenes. Particularly preferred hydrocarbons include mineral oil, light mineral oil, and squalane.

(2) Siloxane polymers and oligomers, for example, cyclomethicone, cyclopentasiloxane, poly(dimethyl siloxane), and poly(methyl phenyl siloxane). A particularly preferred siloxane oil is cyclomethicone.

(3) Monoesters including fatty acid esters with lower aliphatic alcohols methanol, ethanol and isopropanol; fatty acid esters with aromatic compounds, for example, benzoic acid; fatty acid esters with fatty alcohols. Useful fatty acid esters with lower aliphatic alcohols include propylene glycol monopalmitostearate, propylene glycol monostearate, butyl stearate, methyl decanoate, methyl myristate, methyl stearate, isopropyl myristate, isopropyl palmitate, coco-caprylate/caprate, and isopropyl isostearate. Useful fatty acid esters with fatty alcohols includes cetyl palmitate, cocoyl caprylocaprate, ethylhexyl hydroxyl stearate, cetyl esters wax and decyl oleate. Particularly preferred monoester oils are propylene glycol monopalmitostearate, propylene glycol monostearate, butyl stearate, cetearyl ethyhexanoate, cetyl esters wax, cetyl palmitate, ethylhexyl hydroxyl stearate, isopropyl isostearate, coco-caprylate/caprate, and isopropyl palmitate.

(4) Polyesters including: fatty acid esters of polyols including triglycerides, sucrose polyesters, trimethylol propane triesters, pentaerythritol and dipentaerythritol polyesters, and glycol or poly(alkylene glycol) diesters such as propylene glycol dicaprylate; and fatty alcohol esters of di and polyacid compounds, for example, phthalic, isophthalic, trimelletic, adipic, succinic, glutaric, and citric acid such as disopropyl adipate. Useful triglycerides include spermaceti and vegetable oils, for example, almond oil, castor oil, hydrogenated castor oil, cocoa butter, coconut oil, safflower oil, shea butter, soybean oil, fractionated coconut oil (also known as caprylic/capric triglyceride), sesame oil, sunflower seed oil, olive oil, peanut oil, olive oil, hydrogenated vegetable oil, and canola oil and synthetic triglycerides, for example, medium chain triglyceride (MCT) oil, tricaprin, tridecanoin, triolein, and tristearin. Useful diesters include propylene glycol esters, for example, propylene glycol dicaprylate/dicaprate and propylene glycol dimyristate and diesters of organic diacids including diisopropyl adipate and diethyl succinate. Preferred polyesters are spermaceti, vegetable oil, hydrogenated vegetable oil, almond oil, castor oil, hydrogenated castor oil, cocoa butter, coconut oil, safflower oil, shea butter, soybean oil, fractionated coconut oil (also known as caprylic/capric triglyceride), sesame oil, sunflower seed oil, olive oil, peanut oil, olive oil, canola oil, medium chain triglyceride (MCT) oil, diethyl sebacate, diisopropyl adipate, and propylene glycol dicaprylate. Particularly preferred polyesters are saturated and are liquids at about 20° C. and include fractionated coconut oil, medium chain triglyceride (MCT) oil, diethyl sebacate, diisopropyl adipate, and propylene glycol dicaprylate/dicaprate.

(5) Essential oils including thyme oil, eucalyptus oil, salicylic acid esters, terpenoids, diterpenoids and polyterpenoids and derivatives thereof including methyl salicylate, geraniol, d-limonene, camphor, and menthol. Particularly preferred essential oils include d-limonene and alpha-terpineol.

(6) Sterols and sterol esters, for example, lanolin.

(7) Ethylenically unsaturated compounds, including mono-, di- and poly-functional water immiscible compounds. Exemplary ethylenically unsaturated compounds include allyl acrylate, ethyl acrylate, pentaerythritol triacrylate, pentaerythrtol tetraacrylate, 2-t-butyl cyclohexanol acrylate, 1,6-hexanediol diacrylate, stearyl acrylate, behenyl acrylate, isobornyl acrylate, isooctyl acrylate, isotridecyl acrylate, lauryl acrylate, 1,10-decanediol diacrylate, methyl methacrylate, 2-t-butyl cyclohexanol methacrylate, 1,12-dodecanediol dimethacrylate, and lauryl methacrylate.

In preferred embodiments of the present invention, oils are selected from those listed in the United States Food and Drug Administration list of Inactive Ingredients. Preferred oils are those that have been approved for topical administration. Preferred oils include soybean oil, safflower oil, tricaprylin, tricaprin, and medium chain triglyceride oils, alpha-terpineol, almond oi, castor oil, cetyl palmitate, cocoa butter, coconut oil, cyclomethicone, dimethicone, diisopropyl adipate, isopropyl myristate, isopropyl palmitate, isopropyl isostearate, isopropyl stearate, lanolin, mineral oil, d-limonene, olive oil, peanut oil, petroleum distillates, and shea butter.

Surfactants

Ibuprofen containing lipoleosomes, nanopouches and nanocapsules of the present invention are characterized by having at least two surfactants. The precursors to oil containing lipid bilayers in liposomes are oil containing lipid bilayers in microemulsions, and formation of lipid bilayers in microemulsions requires polydispersity in the HLB (hydrophilic/lipophilic balance) values of surfactants which is not possible with a single surfactant.

The physicochemical properties of microemulsion lipid bilayers are critical to the formation of small unilamellar liposomes. If microemulsion lipid bilayers are relatively more fluid or flexible, or if mobility of individual components is too high, hydration of the microemulsion results in destruction of the lipid bilayer into monolayers giving filled nanoparticles which include nanopouches and nanocapsules. If microemulsion lipid bilayers are too durable, hydration of the microemulsion win give large multilamellar liposomes.

It has been found that formation of lipid bilayers in microemulsions requires a minimum value of polydispersity in the surfactant HLB values and that the degree of lamellar character in precursor microemulsions can be systematically increased by increasing the HLB polydispersity. In the scientific literature, there are no conventions for expressing polydispersity in HLB values. As it relates to lamellar phase microemulsions, HLB polydispersity can be conveniently expressed as a dimensionless weight mean square deviation, $WMSD_{HLB}$, analogous to the sum of least squares differences used to express goodness of fit (for example, linear correlation coefficient). $WMSD_{HLB}$ is calculated as the sum of the product of the weight fraction of the i-th surfactant species times the square of the deviation of the HLB of the i-th surfactant species from the weight average HLB normalized by dividing by the weight average HLB according to equation (1) (where weight average $HLB=HLBw=\Sigma_i w_i HLB_i$)

$$WMSD_{HLB} = \frac{\sum_i W_i(HLB_i - HLB_w)^2}{HLB_w} \quad (1)$$

The conventional basis for surfactant HLB values is the Griffin's equation (Griffin W., Calculation of HLB Values of Non-Ionic Surfacants, *J. Soc. Cosm. Chem.* 5 (4): 249-56) which may be used to calculate HLB for simple ethoxylated surfactants. A more sophisticated method of calculating HLB values is Davies group contribution method for surfactants including groups with known group contribution factors (Davies, A quantitative kinetic theory of emulsion type, I. Physical chemistry of the emulsifying agent, Gas/Liquid and Liquid/Liquid Interface, *Proc. Int. Congress of Surface Activity*, 426-38). The usefulness of Davies' method can be extended by additional group contribution factors, as for example, are provided in Akzo Nobel Surface Chemistry LLC Technical Information bulletin "HLB & Emulsification-Description of Hydrophile, Lipophile Balance and use of HLB in Producing Emulsions," Publication SC-11-02, ©2011 Akzo Nobel Surface Chemistry LLC.

Because Neither Griffin's or Davies' methods for calculating HLB values are useful for al surfactant types and it is typical to use Griffin's equation for some types and Davies' for others, a more comprehensive method for calculating HLB is of note. Preferably, HLB values for surfactants are calculated using molecular modeling software, for example, Molecular Modeling Pro software, version 5.22, commercialized by Norgwyn Montgomery Software Inc, ©2003. In some cases, it is necessary to use surfactant manufacturer provided HLB values, for example, in the case of mixtures of surfactants, for example, as lecithins. In some cases, the hydrophilic group is too small for molecular modeling to recognize the molecule as a surfactant, in which case Davies' group contribution method is preferred. Ibuprofen influences properties of lamellae in microemulsions therefore the HLB value for ibuprofen (HLB=3.0) should be included in calculations of HLB polydispersity.

In preferred embodiments of the present invention, $WMSD_{HLB}$ is greater than about 2, greater than about 3, and greater than about 5.

In preferred embodiments of the present invention, surfactants are selected from those listed in the United States Food and Drug Administration list of Inactive Ingredients.

In preferred embodiments of the present invention, saccharide residues which retard egress of ibuprofen from nanoparticles including nanopouches, nanocapsules and lipoleosomes are present in surfactant molecules.

Low HLB Surfactants

Particularly preferred low HLB surfactants which include saccharide residues include mono-, di-and polyesters of sorbitan with $C_8$ to $C_{22}$ linear or branched, saturated or unsaturated fatty acids, for example, sorbitan monolaurate, sorbitan monopalmitate, sorbitan stearate, sorbitan oleate, sorbitan sesquioleate, sorbitan trioleate, sorbitan isostearate, sorbitan tristearate, and mixtures of these surfactants. Particularly preferred saccharide residue containing low HLB surfactants are sorbitan stearate and sorbitan oleate. Other low HLB surfactants which include saccharide residues include saturated or unsaturated linear or branched aliphatic $C_8$ to $C_{22}$ carboxylate esters of glucose such as stearoyl glucose, oleyl glucose, myristoylglucose, and lauroylglucose and saturated or unsaturated linear or branched aliphatic $C_8$ to $C_{22}$ carboxylate esters of raffinose such as stearoyl raffinose, oleyl raffinose, myristoylraffinose, and lauroylraffinose. Other low HLB surfactants useful in the present invention include:

(1) mono-and di-esters of glycerin with $C_8$ to $C_{22}$ linear or branched, saturated or unsaturated fatty acids, for example, glycerol monooleate, glyceryl monostearate, glycerol dioleate, glycerol distearate, and mixtures of these surfactants;

(2) mono-and di-esters of ethylene glycol with $C_8$ to $C_{22}$ linear or branched, saturated or unsaturated fatty acids, for example, ethylene glycol monooleate, ethylene glycol monostearate, ethylene glycol dioleate, ethylene glycol distearate, and mixtures of these surfactants.

(3) alcohol ethoxylates, alcohol propoxylates, and alcohol ethoxylate propoxylates formed from the addition of ethylene oxide and/or propylene oxide to Ce to C linear or branched, saturated or unsaturated alcohols, for example, oleth-2, ceteareth-2, and lauryl alcohol 3 mole ethoxylate/6 mole propoxylate (ALKOMOL L 306, product of Oxiteno), and mixtures of these surfactants;

(4) trialkyl phosphates, or a mixture of trialkyl phosphates;

(5) phospholipid compounds, for example, phosphatidyl choline, phosphatidylethanolamine, and phosphatidylinositol and compositions, which include mixtures of these, for example, lecithins. Particularly preferred composition of phospholipid compounds includes phosphatidyl choline, for example Phosphoipon 90G, product of Lipoid LLC, Newark N.J., liquid, non-deoiled lecithins, for example, Alcolec XTRA-A, product of American Lecithin Company in Oxford, Conn., and soybean phospholipids, for, example Alcolec PC 75, product of American Lecithin.

(6) phosphate ester compounds formed from esterification of phosphoric acid with short chain polyethoxylates of $C_8$ to $C_{22}$ linear or branched, saturated or unsaturated fatty alcohols, for example, Rhodafac RP-710, Rhodafac PA32, and Lubrhophos LB400, available from Rhodia, Cranbury N.J.), and mixtures of these surfactants;

(7) Aryl alkyl carboxylic acids, for example, nonyl oxy benzoic acid, 2-(p-isobutylphenyl) propionic acid (ibuprofen), 2-(6-methoxynaphthalen-2-yl) propanoic acid (naproxen), and mixtures of these compounds.

(8) Aryl alkyl alcohols, for example, nonylphenol, octylphenol, 2,2-dimethyl-3-phenylpropanol (muguet alcohol), phenyl allyl alcohol (cinnamyl alcohol), and 8-methyl-N-vanillyl-trans-6-nonenamide (capsaicin), and mixtures of these compounds.

(9) Saturated or unsaturated, linear or branched aliphatic $C_8$ to $C_{22}$ carboxylic acid functional compounds including fatty acids derived from the saponification of vegetable and animal fats and oils, for example, octanoic acid, coconut fatty acid, oleic acid, ricinoleic acid, stearic acid, and carboxylic acid terminated short chain (e.g., n=4) polymers of ricinoleic acid and mixtures of such surfactants.

(10) Saturated or unsaturated linear or branched aliphatic $C_8$ to $C_{22}$ alcohols and diols, for example, octanol, 1,2 octane diol, dodecanol, myristyl alcohol, ceteryl alcohol, stearyl alcohol, isotridecyl alcohol, 3,7-dimethyl-2,6-octadien-1-ol (nerol), and so called Guerbet alcohols, for example, 2-ethyl-1-hexanol, 2-butyl-1-octanol, and 2-octyl-1-dodecanol.

(11) Saturated or unsaturated linear or branched aliphatic $C_8$ to $C_{22}$ primary and secondary amines and diamines, for example, oleyl amine, oleyl diamino propane, and cocoalkyl dimethyl amine.

Medium HLB Surfactants

Medium HLB surfactants useful in the present invention are those which include saccharide residues including sorbitan esters with linear or branched long chain (greater than about 8 carbon atoms) fatty acids onto which ethylene oxide groups have been grafted where the mole ratio of ethylene oxide groups to sorbitan is between 1 and 6. For example, polyoxyethylene (4) sorbitan monolaurate (polysorbate 21) and polyoxyethylene (4) sorbitan monooleate (polysorbate 81).

Polyethoxylated High HLB Surfactants

Stable nanoparticle dispersions are required for commercialization of drug products. For drug products sold within the USA, the Food and Drug Administration allows stability to be determined at 40° C. to accelerate the aging process, i.e., the rate of chemical degradation and/or physical change, where 6 months of accelerated aging at 40° C. is typically conducted to support a 2-year expiry date for launch. Accordingly, preferred nanoparticle dispersions of the current invention are stable including stability with respect to separation for at least 6 months at 40° C.

It is known that nanoparticle dispersions made by phase inversion processes are less stable to phase separation near the phase inversion point. In the case of nanoparticles made by phase inversion resulting from change in temperature, nanoparticle dispersions are increasingly unstable as storage temperatures approach the system phase inversion temperature. Increasing the length of the polyethoxylated chain in compositions comprising polyethoxylated surfactants is well known to increase the phase inversion temperature, and increasing the length of the polyethoxylate chain in such surfactants would be expected to increase storage stability at room temperature and in accelerated aging tests.

Use of relatively longer chain poly(ethylene oxide) surfactants in a process of phase inversion resulting from a change in temperature is described in U.S. Pat. No. 6,221,370. According to this patent, emulsions comprising poly (ethylene oxide) surfactants with chain length equal to 30 were prepared by the phase inversion temperature (PIT) emulsification method, stored for 4 weeks at 40° C., and visually examined for stability. The phase inversion temperature of the compositions was 85° C., allowing for the possibility of good stability when stored at 40° C. It was shown that polyethoxylated high HLB ester surfactants (referred to in U.S. Pat. No. 6,221,370 as fatty acid ethoxylates, exemplified as palmitic/stearic acid+30 EO) gave stable emulsions but if the polyethoxylated high HLB ester surfactants were replaced by polyethoxylated high HLB ether surfactants (referred to as fatty alcohol ethoxylates, exemplified a cetearyl alcohol+30 EO also known as ceteareth-30), the PIT emulsions obtained are not stable. If some of the oil in the polyethoxylated high HLB ester surfactants plus glyceryl stearate plus mineral oil plus caprylic/capric triglyceride plus water system of is replaced with ibuprofen, phase inversion occurs without formation of a microemulsion in the phase inversion zone. Surprisingly, in the case that the system includes ibuprofen, a microemulsion will form in the phase inversion zone if the polyethoxylated high HLB ester surfactant is replaced by a polyethoxylated high HLB ether surfactants (ceteareth-30). Surprisingly, it has been discovered that for compositions including ibuprofen, that microemulsions form in the phase inversion zone and stable nanoparticle dispersions are obtained by phase inversion if the composition contains a polyethoxylated high HLB ether surfactant but unstable nanoparticle dispersions are obtained by phase inversion if the polyethoxylated high HLB surfactant includes only polyethoxylated high HLB ester surfactants.

It has been shown that permeation of ibuprofen and other drugs can be promoted by poly(ethylene oxide) surfactants, however the relative rate of permeation is highest for relatively shorter chain poly(ethylene oxide) lengths. According to a review of the effects of surfactants on penetration across the skin described by Waiters et al (Walters K, Bialik W, Brain K., The effects of surfactants on penetration across the skin. *Int J Cosmet Sci.* 1993 December; 15(6):260-71), oleth-2 was the most effective enhancer for permeation of ibuprofen across human skin whereas surfactants with ethylene oxide chain lengths of 10 (oleth-10) and 20 (oleth-20) were less effective. Similar, the permeation of methyl nicotinate across hairless mouse skin was 4 to 5 times greater for ceteth-8 and ceteth-10 than for ceteth-20 or ceteth-30. In a related study of the cutaneous permeation of piroxicam through guinea pigs in vivo measured as the 8 hour area under the curve (AUC) for lauryl, cetyl, oleyl, and stearyl ethers (Park E, Chang S, Hahn M, Chi S., Enhancing effect of polyoxyethylene alkyl ethers on the skin permeation of ibuprofen. *Int J Pharm.* 2000 Nov. 19; 209(1-2):109-19), it was found that permeation was a maximum for ethylene oxide chain lengths of between about 10 and 15 units, dropping to essentially zero at chain lengths greater than 20. Surprisingly, it has been found that long chain polyoxyethylene alkyl ether surfactants (polyethoxylated high HLB ether surfactants) can provide excellent permeation of ibuprofen when they are a component of a lipid nanoparticle dispersion. In preferred embodiments, polyethoxylated high HLB surfactants include a single component or may contain mixtures of two or more components. In preferred embodiments, the average chain length of the polyethoxylate chain is sufficient to provide phase inversion above about 75° C. as nanoparticle dispersions made by phase inversion are increasingly unstable as the difference between the phase inversion temperature of the microemulsion precursor and product nanoparticle dispersion storage temperature decreases. In preferred embodiments, nanoparticle dispersions include a single component polyethylated high HLB surfactant that has a chain length equal or greater than about 30 units. In preferred embodiments, nanoparticle dispersions include multiple polyethylated high HLB surfactants wherein the number average polyethoxylate chain length is equal or greater than about 30 units. The number average polyethoxylate chain length of a blend of polyethylated high HLB surfactants may be calculated as the sum of the mole fraction of the i-th component times the polyethoxylate chain length of the i-th component.

Particularly preferred polyethoxylated high HLB surfactants are those derived from ethoxylation of linear saturated or unsaturated fatty alcohols such as lauryl alcohol, cetyl alcohol, oleyl alcohol, and stearyl alcohol. Polyethoxylated high HLB surfactants derived from ethoxylation of alcohols may be referred to as polyethoxylated high HLB ether surfactants. Polyethoxylated high HLB surfactants useful in the present invention include blends of polyethoxylated high HLB ether surfactants with other polyethoxylated high HLB surfactants such as polyethoxylated high HLB surfactants derived from ethoxylation of fatty acids which may be referred to as polyethoxylated high HLB ester surfactants. In the case that the polyethoxylated high HLB surfactants includes blends of polyethoxylated high HLB ether surfactants with other polyethoxylated high HLB surfactants, it is preferred that the weight ratio of polyethoxylated high HLB ether surfactants to other polyethoxylated high HLB surfactants is greater than about 1 to 1. Other polyethoxylated high HLB surfactants useful in the present invention include:

(1) polyethoxylate or polyethoxylate/polypropoxylate ethers with saturated or unsaturated, linear or branched aliphatic $C_8$ to $C_{22}$ alcohols, for example, poly(ethylene oxide) octyl ether, poly(ethylene oxide) dodecyl ether, poly(ethylene oxide) myristyl ether, poly(ethylene oxide) ceteryl ether, poly(ethylene oxide) stearyl ether, poly(ethylene oxide) isotridecyl ether, poly(ethylene oxide) 2-ethyl-1-hexanyl ether, poly(ethylene oxide) 2-butyl-1-octyl ether, and poly(ethylene oxide) 2-octyl-1-dodecyl ether, or a mixture of these surfactants.

(2) polyethoxylate or polyethoxylate/polypropoxylate esters with saturated or unsaturated, linear or branched aliphatic $C_8$ to $C_{22}$ carboxylic acids, for example, poly(ethylene oxide) stearate ester, poly(ethylene oxide) laurate ester, and poly(ethylene oxide) oleate ester or a mixture of these surfactants;

(3) polyethoxylated mono-and di-esters of glycerin with linear or branched long chain (greater than about 8 carbon atoms) fatty acids, for example, poly(oxyethylene) glyceryl monolaurate and poly(oxyethylene) glyceryl monostearate or a mixture of these surfactants:

(4) polyethoxylated compounds formed from the addition of ethylene oxide to linear and branched alkylphenol compounds, for example, poly(ethylene oxide) ether with nonyl phenol or octyl phenol or a mixture of these surfactants;

(5) polyethoxylated castor oils, for example, PEG-25 castor oil and PEG-40 castor oil or a mixture of these surfactants;

(6) polyethoxylated compounds formed from the addition of ethylene oxide to amide compounds formed from linear or branched long chain (greater than about 8 carbon atoms) fatty acids, for example, poly(ethylene oxide) ether with coconut acid ethanol amide or a mixture of these surfactants;

(7) polyethoxylated compounds formed from the addition of ethylene oxide to alcohol functional polysiloxanes, for example, poly(ethylene oxide) ether with methyl bis(trimethylsilyloxy)silyl propanol, or a mixture of these surfactants;

(8) EO-PO block copolymers, for example, poly(ethylene oxide)-poly(propylene oxide)-poly(ethylene oxide) block copolymers and poly(propylene oxide)-poly(ethylene oxide)-poly(propylene oxide) block copolymers, or a mixture of these surfactants; Particularly preferred single component polyethoxylated high HLB ether surfactants include ceteareth-30 and steareth-40. Particularly preferred mixtures of polyethoxylated high HLB ether surfactants with polyethoxylated high HLB ester surfactants include steareth-20 plus PEG100 stearate, laureth-23 plus PEG100 stearate, oleth-20 plus PEG100 stearate, ceteth-23 plus PEG100 stearate, ceteth-20 plus PEG100 stearate, and steareth-21 plus PEG100 stearate.

High HLB Non-Ethoxylated Surfactants

In addition to low HLB surfactants and polyethoxylated high HLB surfactants, compositions of the present invention can optionally include high HLB surfactants that do not contain ethylene glycol residues.

Suitable high HLB non-ethoxylated surfactants include:

(1) polyglyceryl monoesters with linear or branched long chain (greater than about 8 carbon atoms) fatty acids, for example, triglycerol monooleate, or a mixture of these surfactants;

(2) alkylated mono-, di-and oligoglycosides containing 8 to about 22 carbon atoms in the alkyl group and ethoxylated alkylated mono-, di-and oligoglycosides containing about 8 to about 22 carbon atoms in the alkyl group, for example, poly(D-glucopyranose) ether with ($C_8$-$C_{22}$) linear primary alcohols (3) mono-and di-esters of glycerin with linear or branched long chain (greater than about 8 carbon atoms) fatty acids further esterified with short chain monocarboxylic acids, for example, glycerol monostearate lactate.

(4) amide compounds formed from linear or branched long chain (greater than about 8 carbon atoms) fatty acids, for example, acid diethanolamide and oleic acid diethanolamide (e.g., Ninol 40-CO and Ninol 201, available from Stepan Corporation, Northfield, Ill. and Hostacor DT, available from Clariant Corporation, Mount Holly, N.C.), or a mixture of these surfactants;

(5) Saturated or unsaturated, linear or branched aliphatic Ca to Cn alkyl sulfonate and sulfate compounds, for example, octanesulfonic acid, sulfuric acid ester with lauryl alcohol, sulfuric acid ester with lauryl alcohol and salts thereof, or a mixture of these surfactants;

(6) sulfonated succinic acid esters with saturated or unsaturated, linear or branched aliphatic $C_8$ to $C_{22}$ alcohols, for example, the bis(2-ethylhexyl) ester of sulfosuccinic acid and the lauryl poly(ethylene oxide) ester of sulfosuccinic acid, or a mixture of these surfactants;

(7) sulfuric acid esters of linear or branched long chain (greater than about 8 carbon atoms) alcohol ethoxylates, alcohol propoxylates, alcohol ethoxylate propoxylates and ethoxylated linear and branched alkylphenol compounds and salts thereof, for example, sodium dodecylpoly(oxyethylene) sulfonate and sodium poly(oxyethylene) octyl phenyl ether sulfonate, or a mixture of these surfactants;

(8) sulfonates of benzene, cumene, toluene and alkyl substituted aromatic compounds and salts thereof, for example, dodecyl benzene sulfonic acid, or a mixture of these surfactants;

(9) carboxylates of alcohol ethoxylates, alcohol propoxylates, alcohol ethoxylate propoxylates and ethoxylated linear and branched alkylphenol compounds and salts thereof, for example, poly(ethylene oxide) tridecyl alcohol ether carboxylic acid and sodium poly(ethylene oxide) lauryl ether carboxylate, or a mixture of these surfactants;

(10) long chain (greater than about 8 carbon atoms) acyl amino acids, for example, acyl glutamates, acyl peptides, acyl sarcosinates, acyl taurates, salts thereof, and mixtures of these surfactants;

(11) Saturated or unsaturated, linear or branched aliphatic $C_8$ to $C_{22}$ alkyl amido propyl (dimethyl ammonio) acetate compounds, for example, lauramidopropyl betaine and stearamidopropyl betaine, and mixtures of these surfactants.

(12) Sophorolipids, which consist of a hydrophobic fatty acid tail of a hydroxylated 16 or 18 carbon atom fatty acid, which is β-glycosidically linked to a hydrophilic sophorose head, including free acid (open) and internally esterified (lactonic) forms and acetylated forms (acetylated on the 6'-and/or 6"-positions). Sophorolipids useful in the practice of this invention include product mixtures produced by yeasts, for example, *Candida bombicola, Candida apicola, Starmerella bombicola*, and *Candida* sp. NRRL Y-2720 (as identified by Price et al., Carbohydrate Research 348 (2012) 33-41) and chemically modified product mixtures.

(13) Rhamnolipids including mono-rhamnolipids, which consist of one or two 3-(hydroxyalkanoyloxy) alkanoic acid tails and a single rhamnose head and di-rhamnolipids, which consist of one or two 3-(hydroxyalkanoyloxy) alkanoic acid tags and two rhamnose heads, including mixtures of compounds produced by *Pseudomonas* and *Burkholderia* bacterial species, for example, *Pseudomonas aeruginosa* and *Burkholderia plantarii*.

Hydrophilic Non-Amphipathic Polysaccharide Compounds

Ibuprofen nanoparticle compositions of the present invention optionally include hydrophillic non-amphipathic polysaccharide compounds. Suitable hydrophilic non-amphipathic polysaccharide compounds include (1) dextrins such as maltodextrin and cyclodextrin,
(2) gums such as xanthan gum and guar gum,
(3) water soluble cellulose derivatives such as methyl cellulose and hydroxypropyl methyl cellulose, and
(4) water dispersible or water-soluble starches.

Cationic Surfactants

Compositions of the present invention optionally include cationic surfactants. Suitable cationic surfactants include:

(1) fatty alkyl primary and secondary amine and heterocyclic ring functional compounds, for example, oleyl amine, oleyl diaminopropane, alkenyl and aryl alkyl substituted azlactone ring compounds, and alkenyl substituted imidazole ring compounds, for example, oleyl hydroxyethyl imidazoline;

(2) fatty alkyl tertiary amine compounds, for example, lauryl dimethyl amine and cocoalkyl dimethyl amine:

(3) quaternary ammonium salts, for example, didecyl dimethyl ammonium chloride and benzalkonium chloride; and mixtures of these surfactants Water Miscible Co-Solvents Water miscible liquids may optionally be employed as co-solvents in the compositions, including mono-, di- and poly functional alcohol compounds such as hexylene glycol, sec-butanol, ethanol, isopropanol, diacetone alcohol, cyclohexanol, propylene glycol, ethylene glycol, 2-ethyl hexanol, 2-methyl butanol, n-pentanol, ethylene glycol propyl ether, and glycerin, and polyalkylene glycol compounds such as triethylene glycol, dipropylene glycol, ethylene glycol monoethyl ether, diethylene glycol, propylene glycol methyl ether, diethylene glycol methyl ether, diethylene glycol ethyl ether, and dipropylene glycol methyl ether.

Oil/Surfactant Ratio

The physicochemical properties of microemulsion lipid bilayers are critical to the formation of small unilamellar liposomes depends upon the properties of the oil and the amount of oil present.

The phase behavior of mixtures of oil, water and surfactants is conveniently described using phase diagrams. A relevant phase diagram for compositions that give lamellar phase microemulsions is the pseudo binary phase diagram with a surfactant endpoint and water plus oil endpoint on the horizontal axis and temperature on the vertical axis. In such binary phase diagrams for mixtures containing oi, water, and ethoxylated surfactants, phase boundaries frequently take a fish shaped appearance with the head oriented in the direction of the oil plus water endpoint and the tall oriented towards the surfactant endpoint. The body of the fish and the area surrounding the fish represent three and two-phase regions, respectively, and the tall represents a single phase microemulsion region, the width of which expands in the temperature dimension as the amount of surfactant in the system increases. Preferable precursors for oil swollen unilamellar liposomes are single phase lamellar microemulsions which occur in the tail section of pseudo binary oil-water-surfactant diagrams. Although the tail in oil-water-surfactant pseudo binary phase diagrams may be divided into an inner lamellar liquid crystal region which exhibits depressed electrical conductivity and decreased transparency plus a surrounding isotropic region (F. Schambil et al., "Interfacial and colloidal properties of cosmetic emulsions containing fatty alcohol and fatty alcohol polyglycol ethers," *Progr Colloid & Polymer Sol*, 73:37-47 (1987); P. Izquierdo et al., "Phase Behavior and Nano-emulsion Formation by the Phase Inversion Temperature Method," *Langmuir*, 2004, 20, 6594-4598), the presence of lamellae critical for formation of small unilamellar liposomes can be discerned throughout the entire single-phase tail region by including macroscopic observation through crossed polarizing films along with the conventional microscopic observation. The effect of the ratio of oil to surfactants on the extent of lamellar character in a composition of oil, water, and surfactant can then be gauged in terms of the degree to which conductivity is depressed in the inner lamellar liquid crystal region of the tail, the temperature range in which conductivity is depressed, and the temperature range that the composition exhibits either macroscopic or microscopic birefringence.

The extent of lamellar character in microemulsions increases and then decreases as the ratio of oil to surfactants increases. A mixture of surfactants and water with no oil shows a monotonic increase in conductivity as it cools, with no intermediate transparent single-phase region and a minimum amount of oil is required for lamellae and microemulsion formation. The presence of lamellae can be discerned as a reduction in conductivity in the form of a very broad negative peak and temperature regions in which the composition is transparent and shows birefringence. Further addition of oil causes an increase in the temperature range within which the composition is a single phase microemulsion and the development of an intermediate inner lamellar liquid crystal region (inner less transparent tail region of a pseudo ternary phase diagram). Beyond an optimal amount of oil, lamellar character of the composition decreases until once again no microemulsion is observed and conductivity increases monotonically when the composition cools. For the system of isopropyl myristate, polysorbate-80 and lecithin, evidence for lamellar character was observed at oil to surfactant ratios ranging between 0.12:1 and 4.5:1, with maximum formation at ratios of oil to surfactant between about 0.24:1 and about 2.5:1. Microemulsions were observed at oil to surfactant ratios ranging between 0.12:1 and 3.5:1. In preferred compositions for the preparation of nanoparticles from lamellar phase microemulsions, the ratio of water immiscible oil to surfactant with ibuprofen included as a component of the water immiscible oil is less than 4:1, less than 3:1 and less than 2.5 to 1. In preferred compositions for the preparation of liposomes nanoparticles from lamellar phase microemulsions, the ratio of water immiscible oil to surfactant is greater than 1:1, greater than 1.5:1, and greater than 2:1.

Additional Components

The ibuprofen containing nanoparticle dispersion compositions can contain additional components if desired. For example, the compositions can contain adjuvants, for example, antimicrobial agents, colorants, UV absorbers, aroma oils, viscosity modifiers, or antioxidants. The amounts and types of such additional components will be apparent to those skilled in the art.

Methods

In general, ibuprofen containing nanopouch, nanocapsule and lipoleosome compositions are prepared by a first step of combining ibuprofen, a water immiscible oil, a low HLB surfactant, a polyethoxylated high HLB surfactant, water, and additional components if desired, mixing with low to moderate shear, and heating the mixture to a temperature where a microemulsion phase exists. In a second step, the microemulsion is rapidly cooled or rapidly cooled and diluted by water or an aqueous composition. In preferred embodiments, the water used for dilution includes additional components, particularly additional components that are unstable at elevated temperatures.

Preferably, the microemulsion is cooled or diluted and cooled to a temperature less than about 40° C. The rate of cooling of the high temperature microemulsion phase is preferably greater than about 1° C. per minute, greater than about 5° C. per minute, greater than about 20° C. per minute, and greater than about 40° C. per minute.

In preferred embodiments, a precursor microemulsion is prepared in a separate vessel and pumped to a second vessel containing water or an aqueous composition.

In preferred embodiments, a precursor coarse emulsion is pumped through a heat exchanger to raise the temperature to a temperature at which a microemulsion exists and then to a second vessel containing water or an aqueous composition.

In preferred embodiments, a precursor microemulsion is prepared in a vessel and pumped through a cooling heat exchanger to provide a nanoparticle product composition that is undiluted from the microemulsion. Optionally, a second fluid stream may be joined with the flow of microemulsion just before or after the heat exchanger to provide additional components to the formulation.

In preferred embodiments, a precursor coarse emulsion is pumped through a heat exchanger to raise the temperature to a temperature at which a microemulsion exists and then through a second cooling heat exchanger to provide a nanoparticle product composition that is undiluted from the precursor coarse emulsion. Optionally, a second fluid stream may be joined with the flow of microemulsion just before or after the cooling heat exchanger to provide additional components to the formulation.

In preferred embodiments, a precursor coarse emulsion is pumped through a microwave heating zone to raise the temperature to a temperature at which a microemulsion exists and then through a cooling heat exchanger to provide a nanoparticle product composition that is undiluted from the precursor coarse emulsion. Optionally, a second fluid stream may be joined with the flow of microemulsion just before or after the heat exchanger to provide additional components to the formulation.

The composition for the topical prevention and treatment of a disorder in humans may be applied in a single administration or in multiple administrations. The compositions are topically applied for at least one day, at least two days, at least three days, at least four days, at least 5 days, once a week, at least twice a week, at least once a day, at least twice a day, multiple times daily, multiple times weekly, biweekly, at least once a month, or any combination thereof.

The composition for the topical prevention and treatment of disorder in humans may be topically applied for a period of time of about one month, about two months, about three months, about four months, about five months, about six months, about seven months, about eight months, about nine months, about ten months, about eleven months, about one year, about 1.5 years, about 2 years, about 2.5 years, about 3 years, about 3.5 years, about 4 years, about 4.5 years, and about 5 years.

Preferably, the composition is applied topically to the involved area until it has healed. The composition is preferably administered six to eight times a day for from one day to a week or more until healing occurs.

EXAMPLES

Unless otherwise indicated, all numbers expressing quantities of ingredients, properties, for example, molecular weight, reaction conditions, and so forth used in the specification and claims are to be understood as being modified in al instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

In the Examples, the following analytical methods were used. Electrical Conductivity was measured using a Thermo Scientific Orion 3-star Conductivity Meter Model 1114000 with a 013005MD 4-cell conductivity cell electrode. Particle size was determined by dynamic laser light scattering using a Microtrac NanoFlex DLS Particle Analyzer.

Example 1

Figure 5:
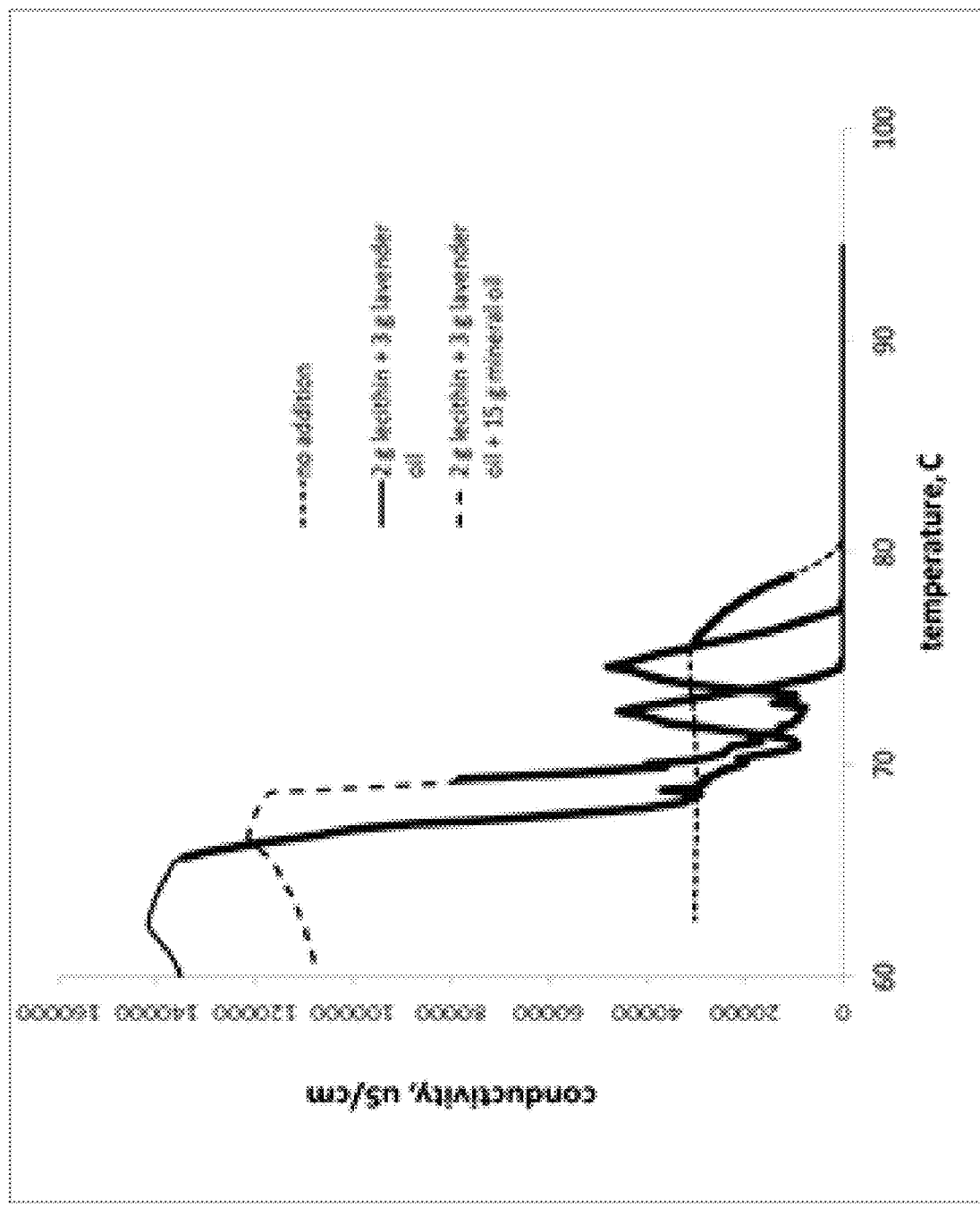
FIG. 5 is a graph of conductivity (uS/cm) vs. Temperature (° C.) for Example 1.

Preparation of a Topical Lotion Composition Including Niosomes of Ibuprofen Isopropyl Myristate, Laureth-23, Sorbitan Stearate, Lecithin and Mineral Oil Isopropyl myristate (50 grams, Lotioncrafter), laureth-23 (12 grams, Lotioncrafter), sorbitan stearate (6 grams, Lotioncrafter), ibuprofen (10 grams, purified from Walgreen's brand of 200 mg generic tablets by extracting with 91% isopropanol/water and recrystallized from isopropanol/water, available from the Walgreen Company, Deerfield, Ill.,)) and distilled water (60 grams) were weighed into a 250-mL beaker. The contents were heated to about 93° C. and allowed to cool to about 63° C. while stirring with a magnetic stir bar and logging the temperature and conductivity. After cooling and replacing water, about 2 grams of Alcolec XTRA-A lecithin and 3 grams of Crafter's Choice Lavender Fields Fragrance Oil (available from Wholesale Supplies, Broadview Heights, Ohio) was added giving a composition with 6.3 weight percent (%) ibuprofen. And the temperature scan repeated from about 95° C. to about 57° C. The composition was transparent between about 65° C. and about 75° C., with some wispy silky swirls growing in as the temperature dropped below about 73° C., becoming isotropic again at about 71° C. After cooling to about 45° C., 15 grams of Crafter's Choice mineral oil (Wholesale Supplies Plus, Inc.) was added and the conductivity monitored between about 60° C. and about 94° C. In this case the composition was very transparent between about 69° C. and about 78° C., with silky swirling anisotropic haze between about 73° C. and about 74° C. Plots of conductivity versus temperature for compositions with isopropyl myristate, laureth-23, sorbitan stearate, lecithin, mineral oil and ibuprofen are shown in FIG. 5. The regions where each composition was transparent or hazy transparent are indicated by wide lines in the plots. After recording the conductivity and temperature, water was replaced and the composition was reheated and quenched from about 75.5° C. into a frozen jacketed plastic beer mug and stirred with a freeze pop to give a translucent beige amber yield stress fluid (that is, a Bingham plastic) which liquefies upon rubbing. The product yield stress fluid was stored at room temperature and after 2 years, showed no signs of separation or deposition of solids. After two years of storage at room temperature, a sample of the composition was stored at 2 to 4° C. for 4 weeks and a portion placed between a coverslip and microscope slide examined for crystals unmagnified and at 200×. No crystals were observed. What this example shows is that nanoparticles including sorbitan stearate, a hydrophobic saccharide compound, effectively encapsulate ibuprofen, preventing formation of ibuprofen crystals.

Example 2

Preparation of a Topical Lotion Composition Including Niosomes of Ibuprofen, Isopropyl Myristate, Laureth-23, Sorbitan Oleate, Lecithin and Mineral Oil The preparation of the final microemulsion of Example 1 was repeated except that sorbitan stearate was replaced with sorbitan oleate. The mole ratio of sorbitan residue to ibuprofen is 0.29 to 1. The dispersed particles particle size was measured by dynamic light scattering found to have volume average particle size of the nanoparticle dispersion=247 nm, number average particle size=94 nm and polydispersity index=1.84. In this case the lotion (Bingham plastic) product made by quenching the microemulsion showed no signs of crystals after storing for 15 days at 2 to 4° C. What this example shows is that nanoparticles including sorbitan oleate, a hydrophobic saccharide compound, effectively encapsulate ibuprofen, preventing formation of ibuprofen crystals.

Example 3

Figure 6:
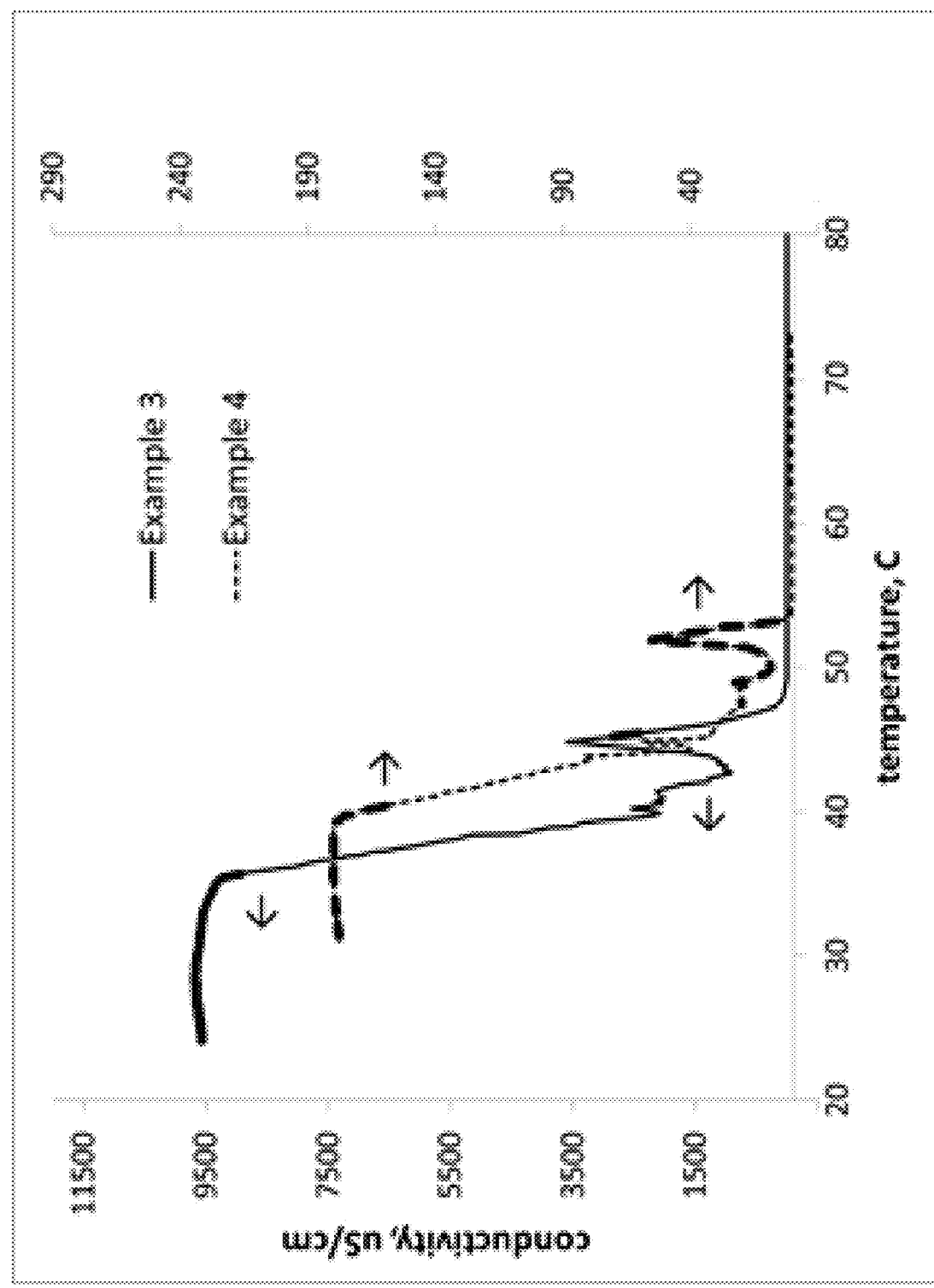
FIG. 6 is a graph of conductivity (uS/cm) vs. Temperature (° C.) for Example 2.

Preparation of Ibuprofen Lipid Nanocapsules Containing Polyethylene Glycol-660 Hydroxystearate, Soybean Phospholipids, Medium Chain Triglyceride Oil, Sodium Chloride and Ibuprofen Nanocapsules containing ibuprofen were prepared as described by Lamprecht et al. [Lamprecht A, Saumet J, Roux J, Benoit J., Lipid nanocarriers as drug delivery system for ibuprofen in pain treatment. *Int J Pharm*. 2004 Jul. 8; 278(2): 407-14]. In a first experiment, the composition with the greatest amount of ibuprofen described in Section 2.2 (Nanocapsule preparation) of Lamprecht et al. was prepared at a 13× greater scale. Briefly, 2.5 grams of ibuprofen, 11.0 grams of Kolliphor HS-15 (polyethylene glycol-660 hydroxystearate, product of Sigma-Aldrich, Milwaukee Wis.), 0.56 grams of Alcolec PC 75 (soybean phospholipids with 70% phosphatidyl choline, product of American Lecithin, Oxford Conn.), 11.3 grams caprylic/capric triglyceride oil (fractionated coconut oil, Lotioncrafter FCO, available from Lotioncrafter, Eastsound Wash.), 0.55 grams sodium chloride, and 38.4 grams of water were heated to 85° C. and allowed to cool until phase inversion occurred (as evidenced by increase in DC conductivity). At 85° C., the sample composition was opaque and moderately viscous with conductivity below 3 microsiemens/cm, indicating that oil is the continuous phase. As the sample cooled to below 50° C., the conductivity began to increase, reaching a local maximum of 3320 microsiemens/cm at 45° C. and eventually plateauing above 9000 microsiemens/cm at about 35° C., indicating a phase inversion temperature range of 35° C. to 50° C. This inversion range is below that reported by Lamprecht et al., who described just one phase inversion range occurring above 55° C. for three different compositions with varying amounts of ibuprofen. The reason for the discrepancy is that ibuprofen decreases the phase inversion of the system, and the three compositions described by Lamprecht et al. do not have the same phase inversion temperature. A plot of conductivity vs. temperature is shown in FIG. 6 (series labeled "Example 3." Temperatures at which the composition has the appearance of a microemulsion are indicated by wide lines in the plots (below 36° C. and between 45° C. and 46° C.). The composition was cycled a total of three times through the inversion range by cooling each time to a temperature below which inversion was complete (<35° C.), rather than cooling to only 55° C. as published. After the final cycle, 62.5 grams of cold (4° C.) water was added quickly with stirring to give a dispersion of ibuprofen containing nanocapsules in which the overall concentration of ibuprofen is 2.0 weight percent (%). After storing the nanocapsule dispersion at 2 to 4° C. for 2 days, a small amount of crystals appeared in clusters at the bottom of the container. When stored at 2 to 4° C. for an additional three days, a moderate amount of crystals was observed on the walls and bottom of the container. What this example shows is that ibuprofen lipid nanocapsules made according to Lamprecht et al. do not encapsulate ibuprofen sufficiently so as to prevent crystallization for 2 days at 2 to 4° C.

Example 4

Preparation of an Ibuprofen Nanocapsule Composition with Polyethylene Glycol-660 Hydroxystearate, Soybean Phospholipids, Medium Chain Triglyceride Oi, and Ibuprofen Temperature cycling of the composition described in Example 3 was repeated except that NaCl was omitted. Accordingly, 5.0 grams of ibuprofen, 21.9 grams of Kolliphor HS-15, 1.12 grams of Alcolec PC 75 soybean phospholipids, 21.2 grams medium chain triglyceride oil and 76.4 grams of water were heated to 85° C. and allowed to cool until phase inversion occurred (as evidenced by increase in DC conductivity). Compared to Example 3, phase inversion occurs at a slightly higher temperature (39° C. to 53° C.) and the conductivity below the inversion point is much lower (plateauing at 180 microsiemens/cm) owing to the absence of NaCl as shown in FIG. 6 (series labeled "Example 4." The composition was cycled a total of three times through the inversion range by cooling each time to a temperature below which inversion was complete (<39° C.), rather than cooling to only 55° C. as published. After cycling, the composition has the appearance of a hazy transparent light-yellow liquid, indicating a water continuous dispersion with small particle size. The cooled sample containing 4.0 weight percent (%) ibuprofen was collected without further dilution and stored at 2 to 4° C. After storing for 5 days, the composition remained transparent and clusters of needle shaped crystals of ibuprofen were observed on the bottom of the sample container. After 7 days, a copious amount of crystals was observed throughout the lower half of the sample. What this example shows is that an ibuprofen lipid nanocapsule composition made according to Lamprecht et al. omitting sodium chloride and the step of diluting with water that contains 4 weight percent (%) ibuprofen does not encapsulate ibuprofen sufficiently so as to prevent crystallization for 5 days at 2 to 4° C.

Example 5

Figure 7:
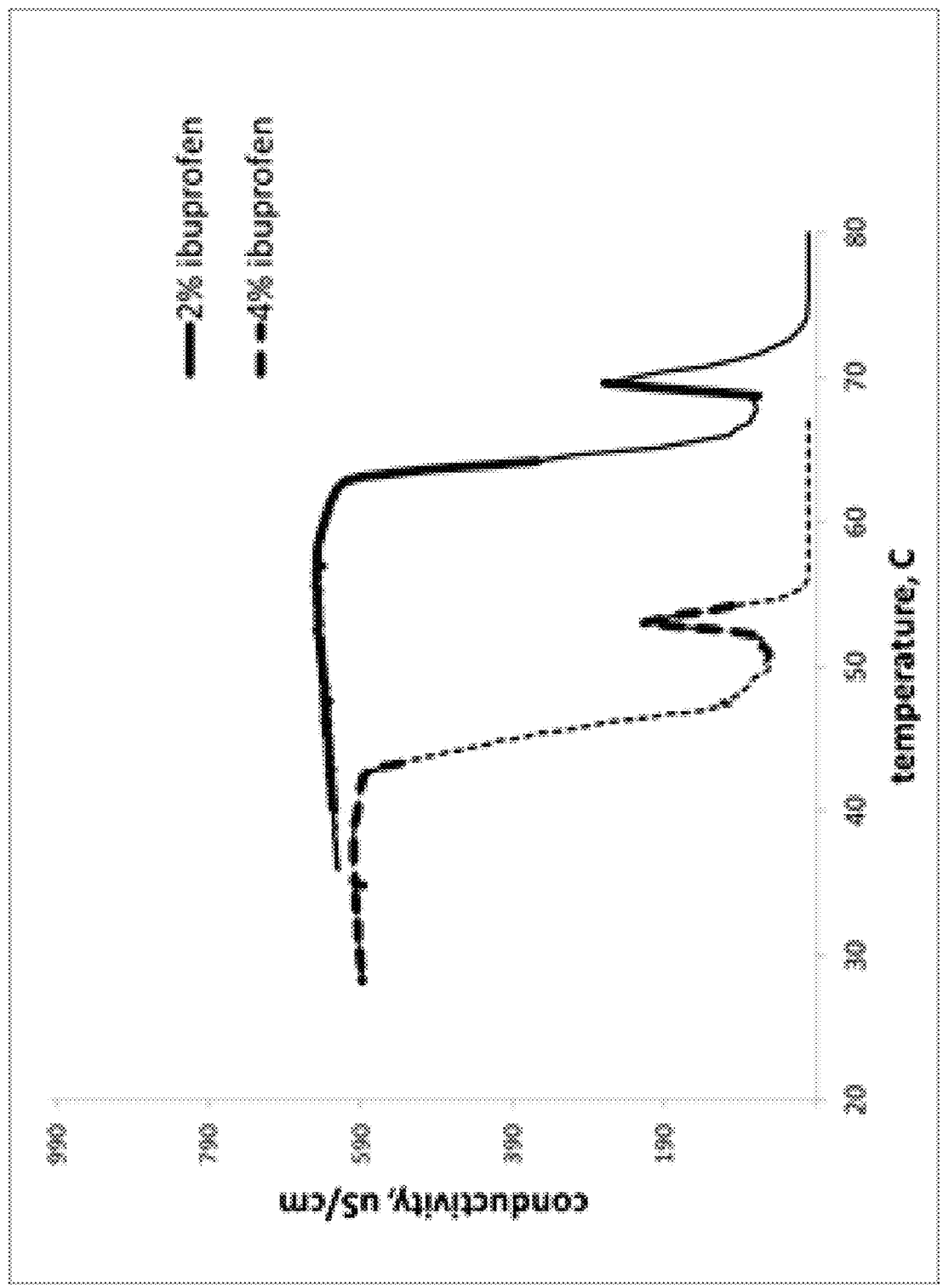
FIG. 7 is a graph of conductivity (uS/cm) vs. Temperature (° C.) for Examples 3 and 4.

Preparation of an Ibuprofen Nanocapsule Composition with Polyethylene Glycol-680 Hydroxystearate, Soybean Lecithin, Medium Chain Triglyceride Oil, and Ibuprofen Nanocapsules were prepared as described by Abdel-Mottaleb et al. [Abdel-Mottaleb M, Neumann D, Lamprecht A., Lipid nanocapsules for dermal application: a comparative study of lipid-based versus polymer-based nanocarriers. *Eur J Pharm Biopharm.* 2011 September; 79(1):36-42.] except that dye and sodium chloride were omitted. A composition containing 2.5 grams of ibuprofen, 22.5 grams of Kolliphor HS-15, 2.50 grams of Alcolec XTRA-A (soybean lecithin, product of American Lecithin, Oxford Conn.), 25.1 grams caprylic/capric triglyceride oi (Lotioncrafter FCO), and 75.3 grams of water (2.0 weight percent (%) ibuprofen) was heated to 85° C. and allowed to cool until phase inversion occurred (as evidenced by increase in DC conductivity). At 80° C., the sample composition was opaque and moderately viscous with conductivity below 1 microsiemens/cm, indicating that oil is the continuous phase. As the sample cooled to below 74° C., the conductivity began to increase, reaching a local maximum of 270 microsiemens/cm at 70° C. and eventually plateauing at about 650 microsiemens/cm at below 60° C., indicating a phase inversion temperature range of 60° C. to 75° C. A plot of conductivity vs. temperature is shown in FIG. 7 (labelled 2 weight percent (%) ibuprofen). The regions where each composition was transparent or hazy transparent are indicated by wide lines in the plots. After cooling, 2.7 grams of additional ibuprofen was added to give a composition with 4.0 weight percent (%) ibuprofen. The composition was heated to 85° C. and again allowed to cool until phase inversion occurred (as evidenced by increase in DC conductivity). At 80° C., the sample composition was opaque and moderately viscous with conductivity below 1 microsiemens/cm, indicating that oil is the continuous phase. As the sample cooled to below 56° C., the conductivity began to increase, reaching a local maximum of 216 microsiemens/cm at 53° C. and eventually plateauing at about 590 microsiemens/cm at below 42° C., indicating a phase inversion temperature range of 42° C. to 56° C. A plot of conductivity vs. temperature is shown in FIG. 7 (labelled 4 weight percent (%) ibuprofen). As a result of the increased concentration of ibuprofen, the phase inversion range has shifted by approximately minus 18° C. At room temperature, the composition is a transparent slightly hazy yellow liquid, indicating a water continuous, fine particle size dispersion. After cycling the temperature between 55° C. and 80° C. three times, the sample was transferred to a sample container and stored at 2 to 4° C. A small amount of crystals was observed after storing for 7 days, and there was a moderate amount of crystals after 3 weeks. What this example shows is that an ibuprofen lipid nanocapsule composition made according to Abdel-Mottalb et al. omitting sodium chloride and the step of diluting with water that contains 4 weight percent (%) ibuprofen does not encapsulate ibuprofen sufficiently so as to prevent crystallization for more than 5 days at 2 to 4° C.

Example 6

Preparation of Ibuprofen Lipoleosomes Including Sorbitan Stearate and Ethoxylated Sorbitan Oleate (Polysorbate 80)

Figure 8:
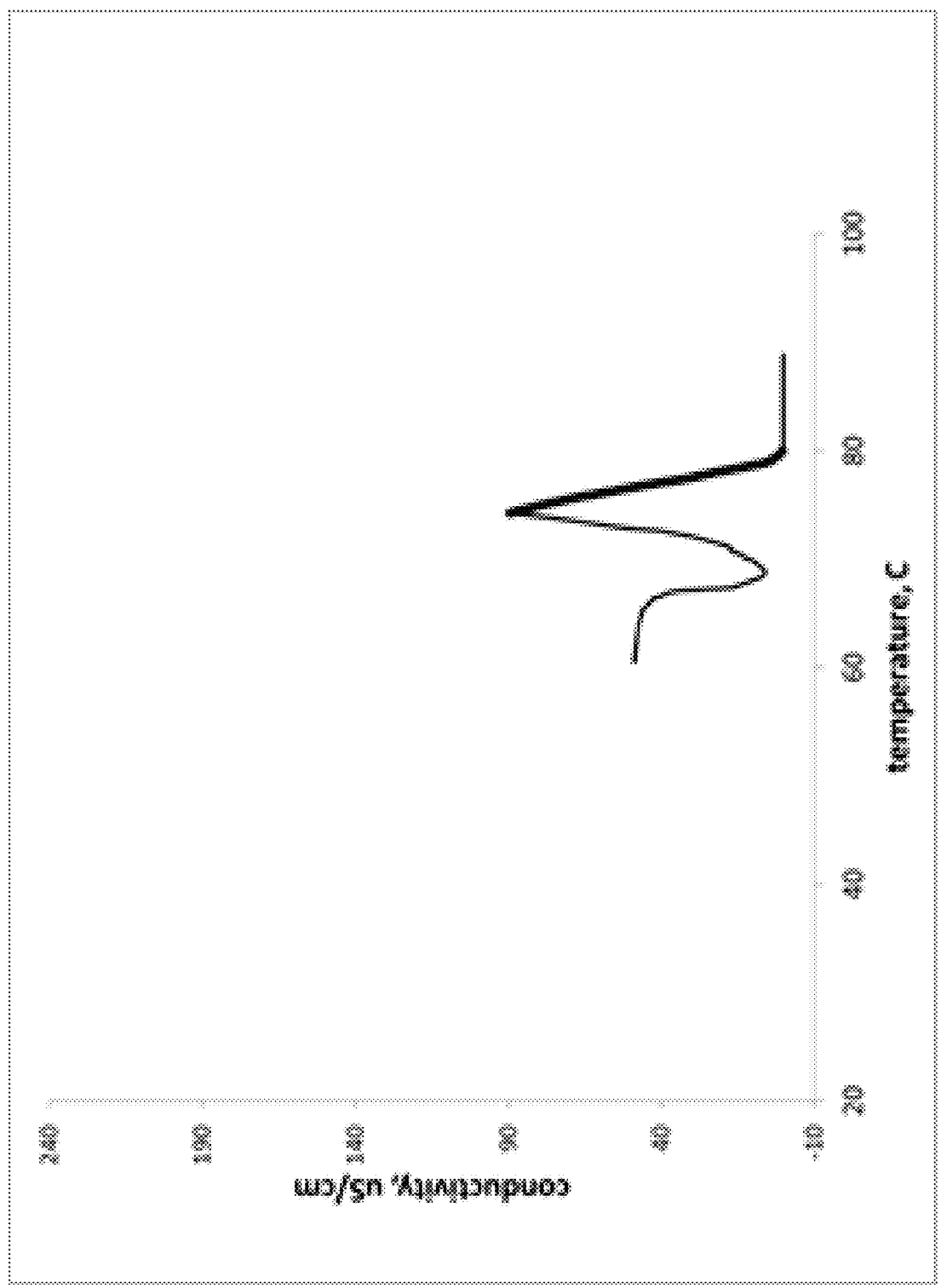
FIG. 8 is a graph of conductivity (uS/cm) vs. Temperature (° C.) for Example 5.

A microemulsion composition was prepared from 12.0 grams polysorbate-80 (product of Lotioncrafter), 3.0 grams of ceteareth-30 (source: Making Cosmetics, Snoqualmie, Wash.), 50.0 grams medium chain triglyceride oil, 9.1 grams of a 33-weight percent (%) solution of Alcolec PC 75 soybean phospholipids in medium chain triglyceride oil, 12.0 grams of sorbitan stearate (product of Lotioncrafter), 6.2 grams ibuprofen, and 60.3 grams of water. This composition contains 4.1 weight percent (%) ibuprofen and the mole ratio of sorbitan residue to ibuprofen is 1.23 to 1. When cooled from 85° C., the composition showed phase inversion between 66° C. and 80° C. and had the appearance of a transparent microemulsion between 74° C. and 80° C. A plot of conductivity vs. temperature is shown in FIG. 8. The microemulsion was cooled rapidly from 79° C. by pouring approximately 100 grams into a stainless-steel pan that had been cooled to about −5° C. giving a glossy, opaque ivory colored yield stress fluid. After storing the sample at 2 to 4° C. for 4 weeks, no crystals were seen in the sample container. When sample was placed between a coverslip and microscope slide and observed at 200×, no crystals were observed. What this example shows is that an ibuprofen nanoparticle composition including a hydrophilic saccharide derivative (polysorbate 80) and a hydrophobic saccharide derivative (sorbitan stearate) effectively encapsulates ibuprofen, preventing formation of ibuprofen crystals.

Example 7

Figure 9:
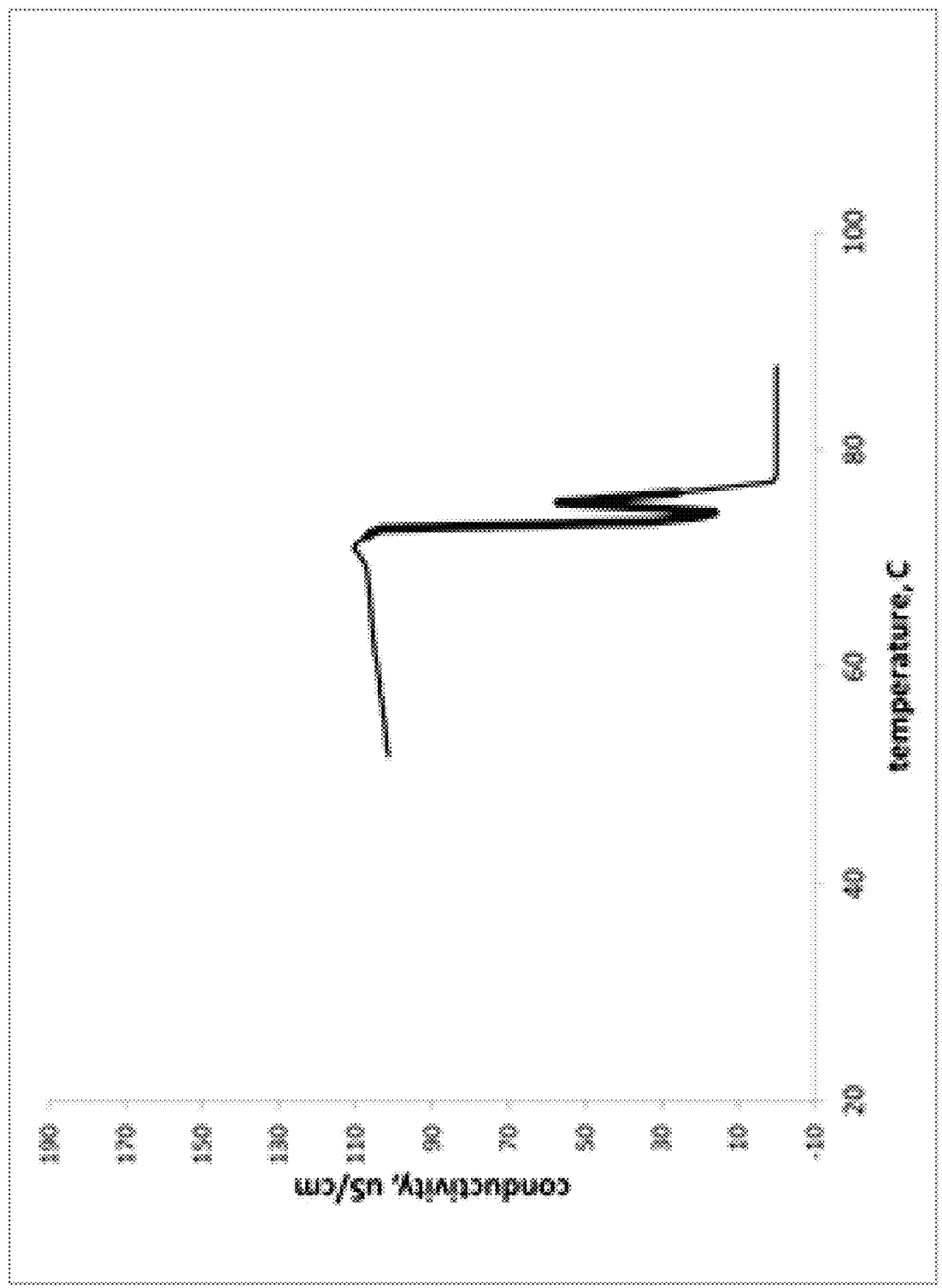
FIG. 9 is a graph of conductivity (uS/cm) vs. Temperature (° C.) for Example 6.

Preparation of Ibuprofen Nanocapsules with Isopropyl Myristate, Ceteareth-20, and Glyceryl Stearate A microemulsion composition was prepared from 6.0 grams ceteareth-20 (product of Lotioncrafter), 3.0 grams of glyceryl stearate (product of Lotioncrafter), 25.0 grams isopropyl myristate, 3.75 grams ibuprofen, and 30 grams of water. This composition contains 5.5 weight percent (%) ibuprofen. When heated to 85° C. and allowed to cool, the composition was a transparent microemulsion between 72° C. and 76° C. A plot of conductivity vs. temperature is shown in FIG. 9. The regions where the composition has the appearance of a microemulsion (transparent or hazy transparent) are indicated by wide lines in the plots. The microemulsion composition was heated to about 85° C. and allowed to cool with stirring to 79° C. and quenched into a stainless-steel pan cooled to −5'C to give a translucent viscous lotion. When stored at 2 to 4° C. overnight, crystals were observed.

Example 8

Preparation of Ibuprofen Nanocapsules with Isopropyl Myristate, Ceteareth-20, Glyceryl Stearate and Maltodextrin The preparation of the microemulsion of Example 7 was repeated except the composition contained 1.5 grams of maltodextrin (N-Zorbit M tapioca maltodextrin, available from Modernist Pantry, Portsmouth N.H.) and only 28.5 grams of water. The concentration of ibuprofen is 5.5 weight percent (%). The dispersed particles particle size was measured by dynamic light scattering found to have volume average particle size of the nanoparticle dispersion=59 nm, number average particle size=29 nm and polydispersity index=5.76. In this case, the quenched lotion produced crystals of ibuprofen in 3 days of storage at 2 to 4° C. This example shows that the formation of ibuprofen crystals is delayed 2 days by the presence of maltodextrin, a hydrophilic polysaccharide.

Example 9

Preparation of Ibuprofen Nanocapsules with Isopropyl Myristate, Ceteareth-20, Sorbitan Stearate and Maltodextrin The preparation of the microemulsion of Example 8 was repeated except that sorbitan stearate was substituted for glyceryl stearate. The mole ratio of sorbitan residue to ibuprofen is 0.38 to 1. The dispersion particle size was measured by dynamic light scattering found to have volume average particle size of the nanoparticle dispersion=55 nm, number average particle size=27 nm and polydispersity index=5.57. In this case, the quenched lotion produced ibuprofen crystals when stored at 2 to 4° C. after 20 days. What this example shows is that while maltodextrin as a hydrophilic saccharide derivative retards the onset of crystal formation for two days, a combination of maltodextrin plus a hydrophobic saccharide derivative (sorbitan stearate) retards crystallization for 18 days.

Example 10

Preparation of Ibuprofen Nanocapsules with Isopropyl Myristate, Ceteareth-20, Sorbitan Oleate and Maltodextrin The preparation of the microemulsion of Example 8 was repeated except that sorbitan oleate was substituted for glyceryl stearate. The dispersion particle size was measured by dynamic light scattering found to have volume average particle size of the nanoparticle dispersion=80 nm, number average particle size=30 nm and polydispersity index=3.16. In this case, the quenched lotion did not produce ibuprofen crystal after storage for 23 days when stored at 2 to 4° C. What this example shows is that a combination of maltodextrin plus a hydrophobic saccharide derivative (sorbitan oleate) retards crystallization for 21 days.

Example 11

Figure 10:
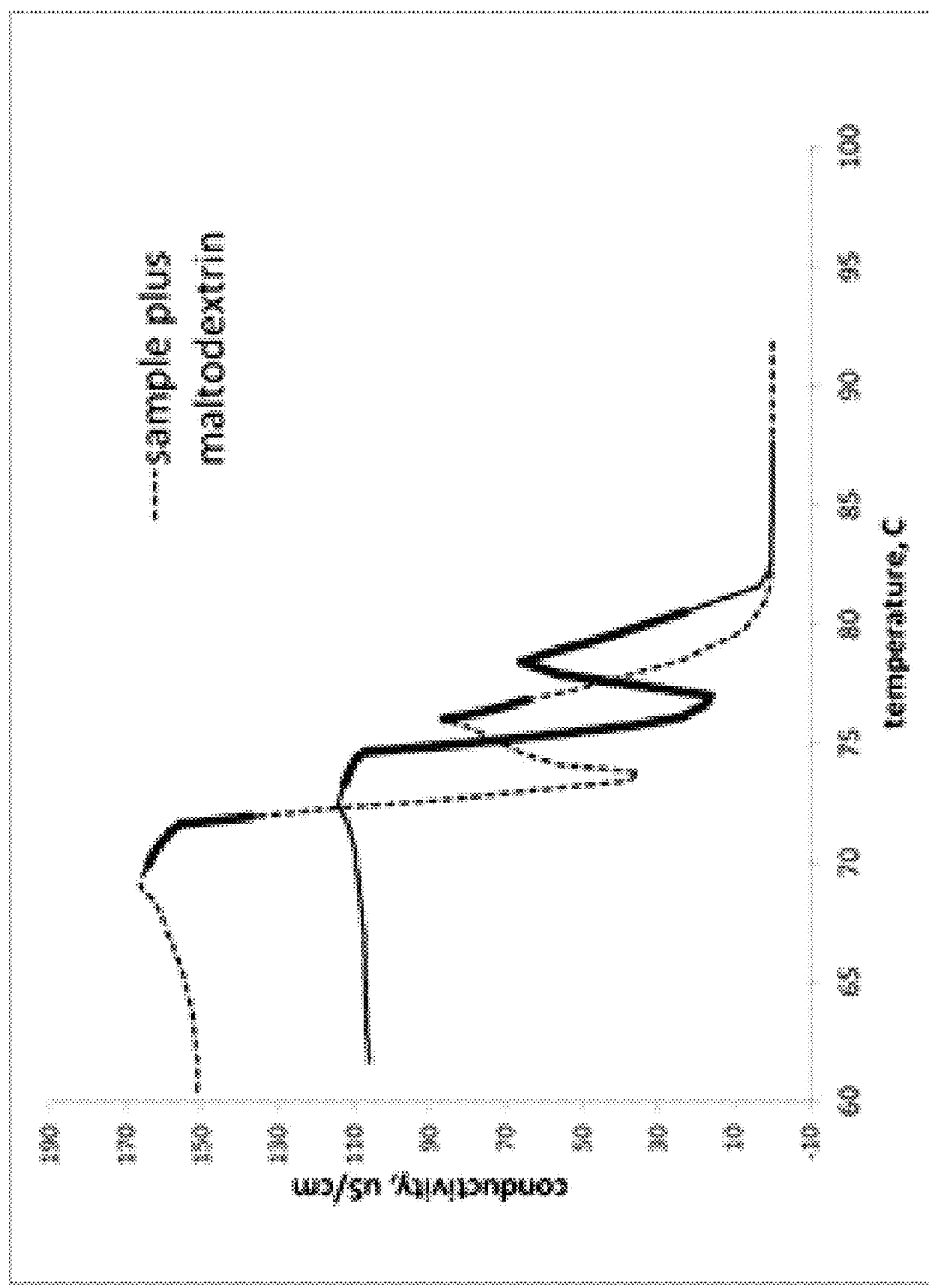
FIG. 10 is a graph of conductivity (uS/cm) vs. Temperature (° C.) for Example 7.

Preparation of Ibuprofen Nanocapsules with Laureth-30, Phosphatidyl Choline, Isopropyl Myristate, and Sorbitan Stearate A microemulsion composition was prepared from 10.4 grams laureth-30 (Jeecol LA-30, product of Jeen International Corporation, Fairfield N.J.), 5.2 grams of sorbitan stearate (product of Lotioncrafter), 43.3 grams isopropyl myristate, 5.3 grams of 33 weight percent (%) Phospholipon 90-G (90% phosphatidyl choline product of Lipoid, Newark N.J.) in medium chain triglyceride oi, 6.5 grams ibuprofen, and 52.1 grams of water. This composition contains 5.3 weight percent (%) ibuprofen. When heated to 90° C. and allowed to cool, the composition was a transparent microemulsion between 73° C. and 81° C. A plot of conductivity vs. temperature is shown in FIG. 10 (unbroken line). The regions where each composition was transparent or hazy transparent are indicated by wide lines in the plots. The microemulsion composition was heated to about 90° C. and allowed to cool with stirring to 82° C. and quenched into a stainless-steel pan cooled to −5° C. to give a translucent gel. When stored at 2 to 4° C., crystals were observed after 3 days.

Example 12

Preparation of Ibuprofen Nanocapsules with Laureth-30, Phosphatidyl Choline, Isopropyl Myristate, Sorbitan Stearate and Maltodextrin The preparation of the microemulsion and quenched nanoparticle product of Example 11 was repeated except the composition also contained 2.7 grams of N-Zorbit M tapioca maltodextrin and only 50.2 grams of water. The concentration of ibuprofen was 5.3 weight percent (%). When heated to 90° C. and allowed to cool, the composition was a transparent microemulsion between 70° C. and 72° C. and between 76° C. and 77° C. A plot of conductivity vs. temperature is shown in FIG. 10 (series labeled sample plus maltodextrin). In this case, the quenched lotion produced crystals of ibuprofen in 19 days of storage at 2 to 4° C. What this example shows is that the combination of a hydrophilic saccharide derivative (maltodextrin) and a hydrophobic saccharide derivative (sorbitan stearate) retards the onset of crystal formation for 16 days longer than a hydrophobic saccharide derivative only.

Example 13

Figure 11:
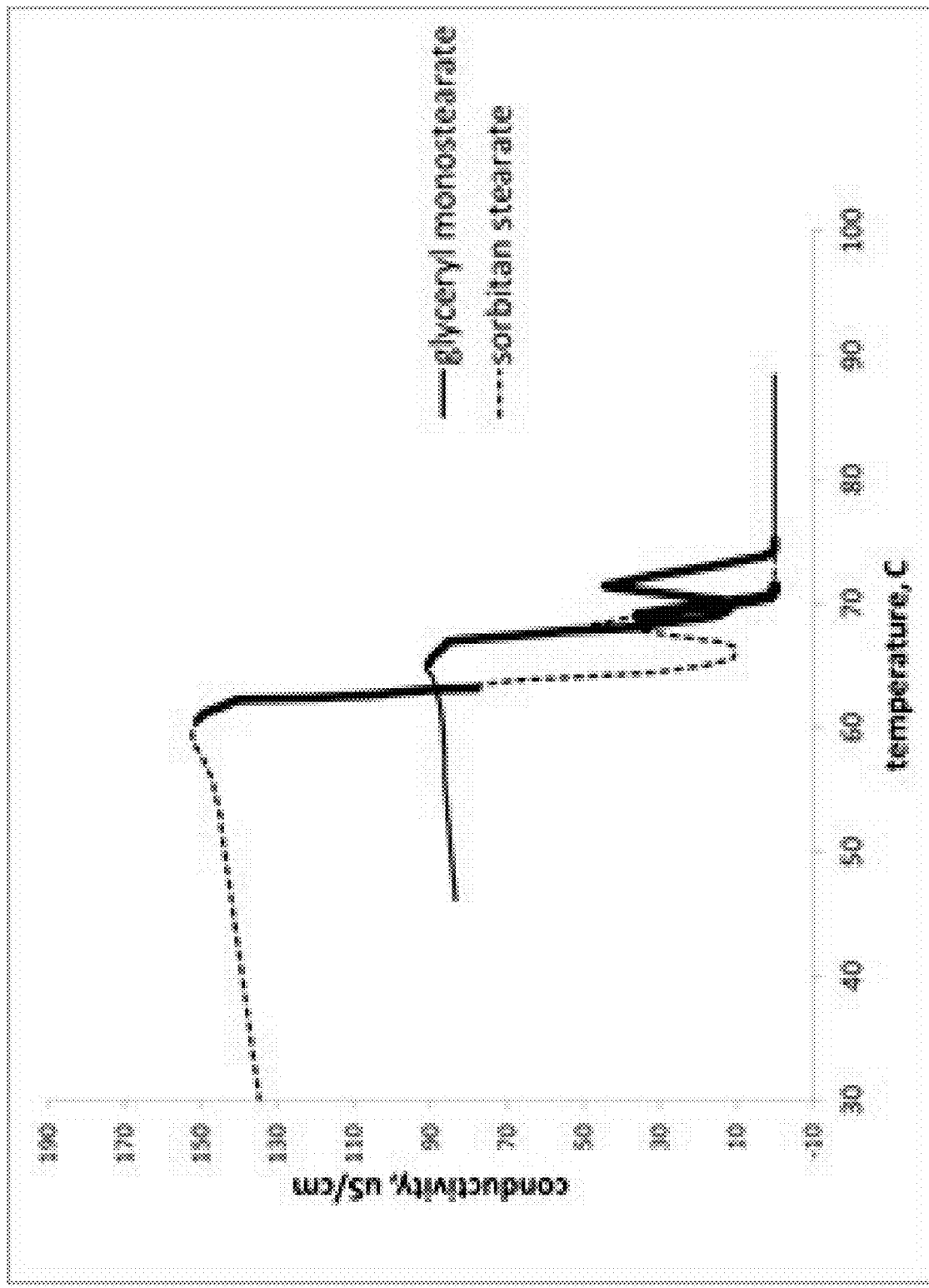
FIG. 11 is a graph of conductivity (uS/cm) vs. Temperature (° C.) for Examples 11 and 12.

Preparation of Ibuprofen Nanocapsules with Polysorbate 80, Glyceryl Monostearate, and Isopropyl Myristate A microemulsion composition was prepared from 6.0 grams polysorbate 80, 6.0 grams laureth-23, 9.0 grams of glyceryl monostearate (product of Lotioncrafter), 50.1 grams isopropyl myristate, 3.0 grams of 33 weight percent (%) Phospholipon 90-G in medium chain triglyceride oil, 7.2 grams ibuprofen, and 60.2 grams of water. This composition contains 5.1 weight percent (%) ibuprofen and the mole ratio of sorbitan residues to ibuprofen is 0.13 to 1. When heated to 90° C. and allowed to cool, the composition was a transparent microemulsion between 65 and 75° C. A plot of conductivity vs. temperature is shown in FIG. 11 (labeled "glyceryl monostearate"). The regions where the composition was transparent or hazy transparent are indicated by wide lines in the plots. The microemulsion composition was heated to about 90° C. and allowed to cool with stirring to 73° C. and quenched into a stainless-steel pan cooled to −5° C. to give a translucent gel. When stored at 2 to 4° C. overnight, crystals were observed after 4 days.

Example 14

Preparation of Ibuprofen Nanocapsules with Polysorbate 80, Sorbitan Stearate, and Isopropyl Myristate The preparation of the microemulsion of Example 13 was repeated except glyceryl monostearate was replaced with an equal weight amount of sorbitan stearate. A microemulsion composition was prepared that contained 6.0 grams polysorbate 80, 6.2 grams laureth-23, 9.0 grams of sorbitan stearate (product of Lotioncrafter), 50.1 grams isopropyl myristate, 3.1 grams of 33 weight percent (%) Phospholipon 90-G in medium chain triglyceride oil, 7.2 grams ibuprofen, and 60.2 grams of water. This composition contains 5.1 weight percent (%) ibuprofen and the mole ratio of sorbitan residues to ibuprofen is 0.73 to 1. When heated to 90° C. and allowed to cool, the composition was a transparent microemulsion between 61° C. and 63° C. and between 69° C. and 71° C. A plot of conductivity vs. temperature is shown in FIG. 11 (labeled "sorbitan stearate"). The microemulsion composition was heated to about 90° C. and allowed to cool with stirring to 73° C. and quenched into a stainless-steel pan to give a translucent gel. The dispersion particle size was measured by dynamic light scattering found to have volume average particle size of the nanoparticle dispersion=90 nm, number average particle size=63 nm and polydispersity index=0.74. When stored at 2 to 4° C. overnight, no crystals were observed after 21 days. After 24 days, a small amount of needle shaped crystals was seen. What this example shows is that the combination of a hydrophilic saccharide derivative (polysorbate 80) and a hydrophobic saccharide derivative (sorbitan stearate) retards the onset of crystal formation for at least 17 days longer than the hydrophilic saccharide derivative only.

Example 15

Preparation of Ibuprofen Nanocapsules with Polysorbate 80, Sorbitan Oleate, and Isopropyl Myristate The preparation of the microemulsion of Example 14 was repeated except glyceryl monostearate was replaced with an equal weight amount of sorbitan oleate. The dispersion particle size was measured by dynamic light scattering found to have volume average particle size of the nanoparticle dispersion=107 nm, number average particle size=51 nm and polydispersity index=1.75. In this case the lotion prepared by quenching the microemulsion showed no crystals after storing for 15 days at 2 to 4° C. and very few well-formed rod-shaped crystal (3 crystals about 100 microns by 2 to 5 mm in approximately 5 mL volume) after storing for 17 days at 2 to 4° C. What this example shows is that the combination of a hydrophilic saccharide derivative (polysorbate 80) and a hydrophobic saccharide derivative (sorbitan oleate) retards the onset of crystal formation for at least 11 days longer than the hydrophilic saccharide derivative only.

Example 16

Preparation of Ibuprofen Nanoparticles with Polysorbate 80, Caprylic/Capric Triglyceride Oil, Phosphatidyl Choline, Ceteareth-30 and Sorbitan Oleate A microemulsion composition was prepared from 12.0 grams polysorbate 80, 3.0 grams of Phospholipon 90G, 50.2 grams of caprylic/capric triglyceride oil (Lotioncrafter FCO), 11.2 grams of sorbitan oleate (product of Sigma Aldrich), 3.1 grams ceteareth-30, 7.5 grams ibuprofen, and 60.2 grams of water. This composition contains 5.1 weight percent (%) ibuprofen. When heated to 90° C. and allowed to cool, the composition had the appearance of a transparent microemulsion at 77° C. A sample of the microemulsion was quenched from 77° C. to give a nearly transparent light-yellow gel. The dispersion particle size was measured by dynamic light scattering found to have volume average particle size of the nanoparticle dispersion=76 nm, number average particle size=37 nm and polydispersity index=1.77. This sample showed no crystals after storing for 22 days at 2 to 4° C.

Example 17

Figure 12:
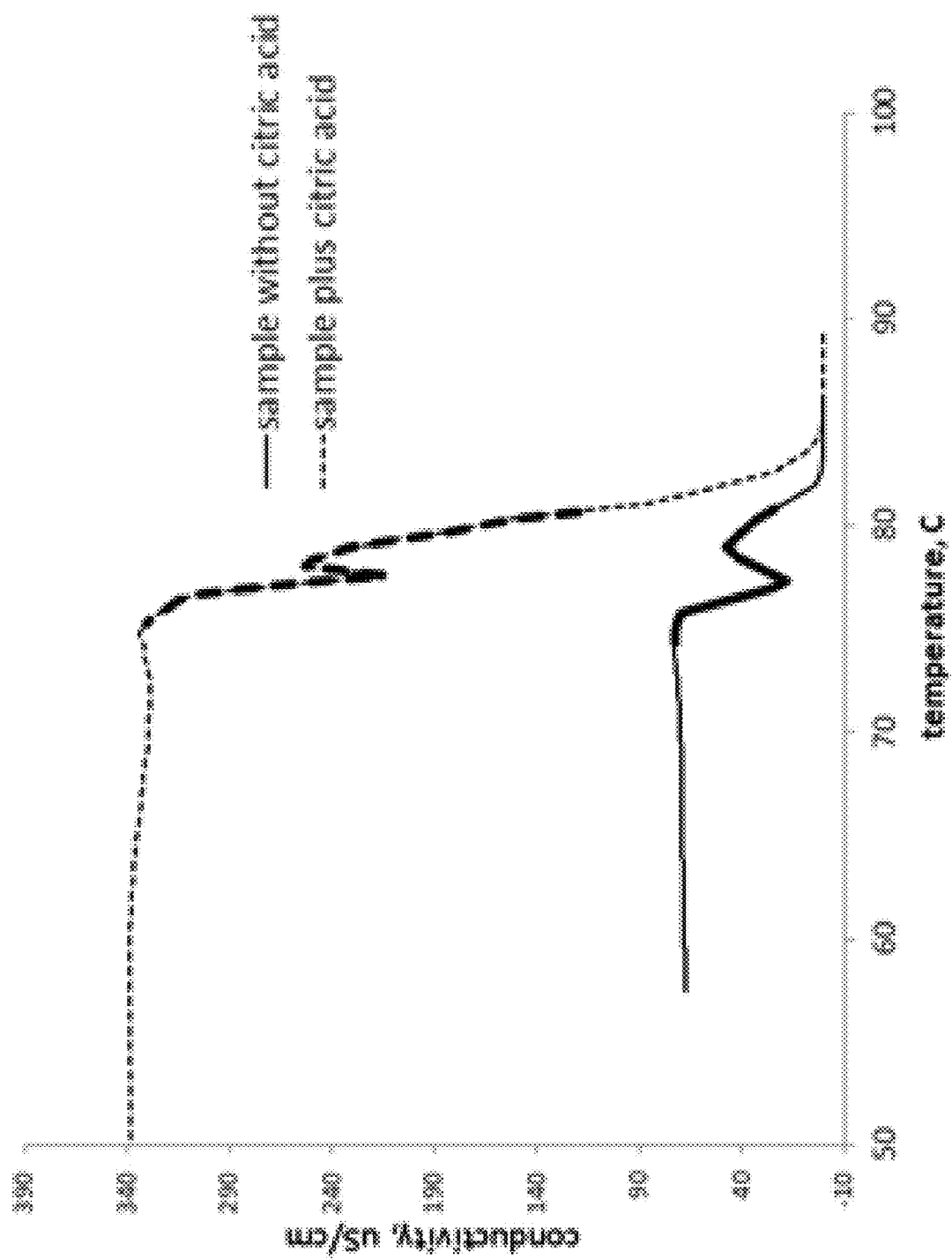
FIG. 12 is a graph of conductivity (uS/cm) vs. Temperature (° C.) for Examples 13 and 14.

Preparation of Ibuprofen Nanocapsules with Ibuprofen, Isopropyl Myristate, Laureth-30, Glyceryl Monostearate and Phosphatidyl Choline A microemulsion composition was prepared that contained 6.20 grams ibuprofen, 41.41 grams isopropyl myristate, 9.94 grams laureth-30, 5.02 grams glyceryl monostearate, 5.10 grams of 33% Phospholipon 90G in caprylic/capric triglyceride oil (Lotioncrafter FCO), and 50.74 grams of distilled water. The concentration of ibuprofen was 5.2 weight percent (%). The composition was heated to 86° C. and allowed to cool while measuring conductivity. A plot of conductivity vs. temperature is shown in FIG. 12 labeled "sample without citric acid." Regions where the composition had the appearance of a microemulsion are noted by thicker lines in the plot. A 75 grams sample of the microemulsion was quenched from 78° C. into a stainless-steel pan cooled to −5° C. to give a translucent gel. When stored at 2 to 4° C. for 6 days, crystals of ibuprofen were observed.

Example 18

Preparation of Ibuprofen Nanocapsules with Ibuprofen, Isopropyl Myristate, Laureth-30, Glyceryl Monostearate, Phosphatidyl Choline, and Citric Acid The procedure of Example 18 was repeated except the composition also contained 0.50 grams of citric acid. The concentration of ibuprofen was 5.3 weight percent (%). A plot of conductivity vs. temperature is shown in FIG. 12 labeled "sample plus citric acid." An 80 grams sample of the microemulsion was quenched from 79° C. into a stainless-steel pan cooled to −5° C. to give a translucent gel. When stored at 2 to 4° C. for 4 days, crystals of ibuprofen were observed. What this example shows is that lowering the pH of a dispersion of nanoparticles with ibuprofen, isopropyl myristate, laureth-30, glyceryl monostearate, and phosphatidyl choline does not slow crystallization of ibuprofen.

Example 19

Preparation of S-(+)-Ibuprofen Nanoparticles with Isopropyl Myristate, Ceteareth-20, Sorbitan Stearate, and Maltodextrin A microemulsion composition was prepared from 6.0 grams ceteareth-20 (product of Lotioncrafter), 3.0 grams of sorbitan stearate (product of Lotioncrafter), 25.0 grams isopropyl myristate, 3.76 grams S-(+)-ibuprofen, 28.8 grams of water and 1.51 grams N-Zorbit M tapioca maltodextrin. This composition contains 5.5 weight percent (%) ibuprofen. The microemulsion composition was heated to about 85° C. and allowed to cool with stirring to 79° C. and quenched into a stainless-steel pan cooled to −5° C. to give a translucent viscous lotion. When stored at 2 to 4° C., no crystals were observed after 18 days.

Example 20

Preparation of S-(+)-Ibuprofen Nanoparticles with Polysorbate 80, Phosphatidyl Choline, Caprylic/Capric Triglyceride Oil and Sorbitan Oleate A microemulsion composition was prepared from 6.0 grams polysorbate 80, 1.5 grams of Phospholipon 90G, 25.1 grams of caprylic/capric triglyceride oil (Lotioncrafter FCO), 5.5 grams of sorbitan oleate (product of Sigma Aldrich), 3.75 grams S-(+)-ibuprofen, 1.5 grams of ceteareth-30, and 30.2 grams of water. This composition contains 5.1 weight percent (%) S-(+)-ibuprofen. The mole ratio of sorbitan residue to ibuprofen is 0.96 to 1. When heated to 90° C. and allowed to cool, the composition had the appearance of a transparent microemulsion at 77° C. A sample of the microemulsion was quenched from 77° C. to give a nearly transparent light-yellow gel. The dispersion particle size was measured by dynamic light scattering found to have volume average particle size of the nanoparticle dispersion=49 nm, number average particle size=24 nm and polydisperisty index=4.29. This sample showed no crystals after storing for 20 days at 2 to 4° C.

Example 21

Figure 13:
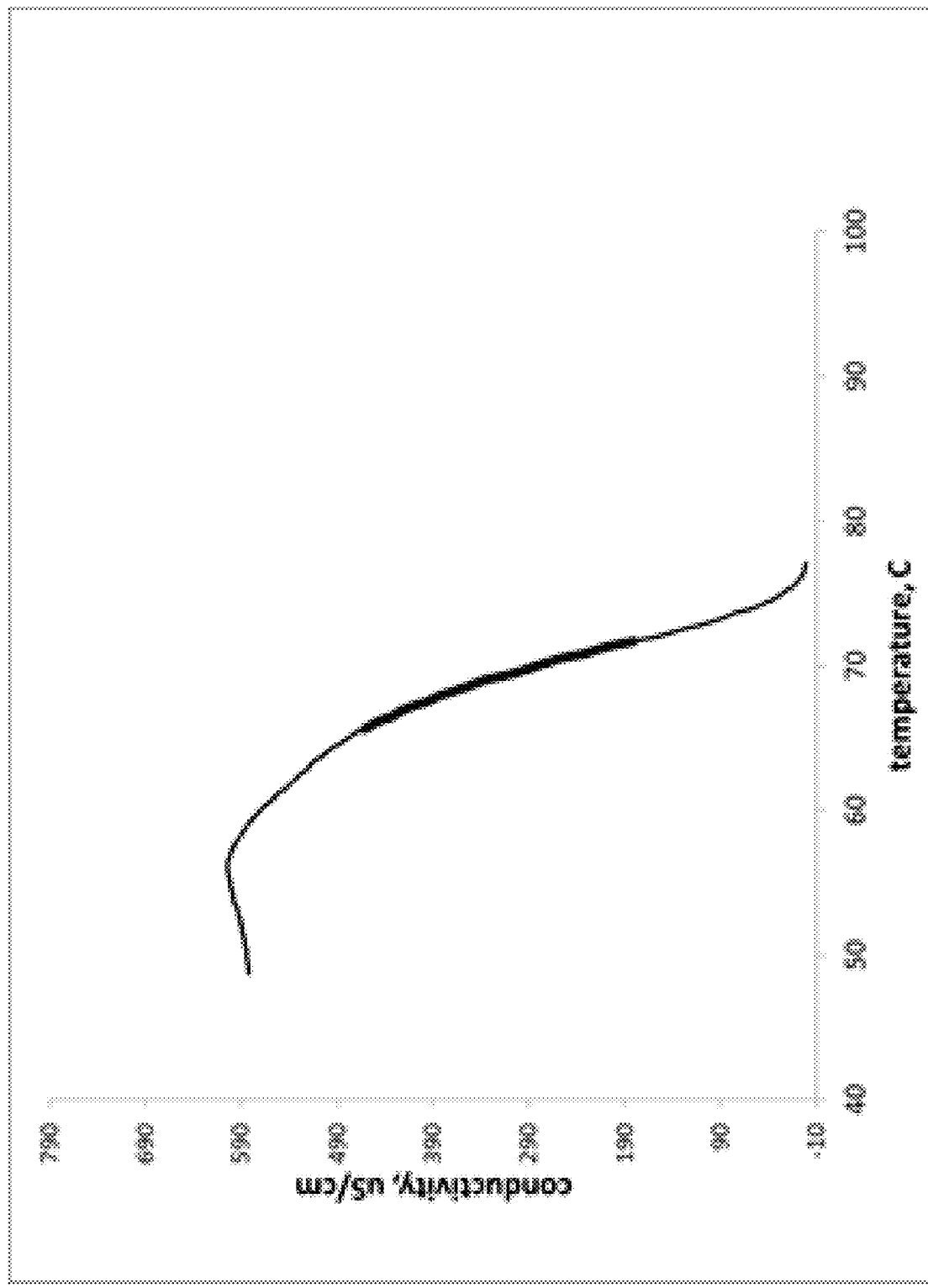
FIG. 13 is a graph of conductivity (uS/cm) vs. Temperature (° C.) for Examples 17 and 18.

Preparation of Ibuprofen Nanopouches with Polysorbate 80, Ethoxylated Castor Oil, Lecithin, Caprylic/Capric Triglyceride Oil, and Sorbitan Oleate A microemulsion composition was prepared from 12.0 grams polysorbate 80, 3.0 grams of Jeechem CA-40 PEG-40 castor oil, 3.0 grams of Alcolec XTRA-A lecithin, 50.1 grams of caprylic/capric triglyceride oil (Lotioncrafter FCO), 11.2 grams of sorbitan oleate, 7.5 grams ibuprofen, and 60.0 grams of water. This composition contains 5.2 weight percent (%) ibuprofen. All of the surfactants (polysorbate 80, Jeechem CA-40, and sorbitan oleate) are liquids at room temperature. When heated to 90° C. and allowed to cool, the composition had the appearance of a transparent microemulsion between 65° C. and 72° C. A plot of conductivity vs. temperature is shown in FIG. 13, where the appearance of a microemulsion is indicated by a thickened plot line. A 120-gram portion of the microemulsion was quenched from 74° C. into a cold pan to give a translucent viscous lotion. The dispersion particle size was measured by dynamic light scattering found to have volume average particle size of the nanoparticle dispersion=208 nm, number average particle size=61 nm and polydispersity index=2.13. This sample showed no crystals after storing for 14 days at 2 to 4° C. What this example shows is that an ibuprofen nanoparticle dispersion prepared using surfactants that include saccharide residues in which all surfactants are liquids at room temperature is stable with respect to crystallization of ibuprofen.

Example 22

Preparation of Ibuprofen Nanoparticles with Polysorbate 80, Polysorbate 21, Phosphatidyl Choline, and Caprylic/Capric Triglyceride Oil A microemulsion composition was prepared from 7.4 grams polysorbate 80, 7.6 grams polysorbate 21 (product of Spectrum Chemical Mfg. Corp., New Brunswick N.J.), 3.13 grams Phospholipon 90G, 43.4 grams of caprylic/capric triglyceride oil (Lotioncrafter FCO), 4.6 grams ibuprofen, and 38.8 grams of water. This composition contains 4.5 weight percent (%) ibuprofen. When heated to 90° C. and allowed to cool, the composition had the appearance of a transparent microemulsion between 53° C. and 69° C. A 91-gram portion of the microemulsion was quenched from 67° C. into a cold pan to give a translucent viscous lotion. The dispersion particle size was measured by dynamic light scattering found to have volume average particle size of the nanoparticle dispersion=141 nm, number average particle size=63 nm and polydispersity index=1.20. This sample showed no crystals after storing for 19 days at 2 to 4° C. What this example shows is that an ibuprofen nanoparticle dispersion which includes a high HLB surfactant with a saccharide residue and a medium HLB surfactant with a saccharide residue is stable with respect to crystallization of ibuprofen.

Examples 23-28

Figure 14:
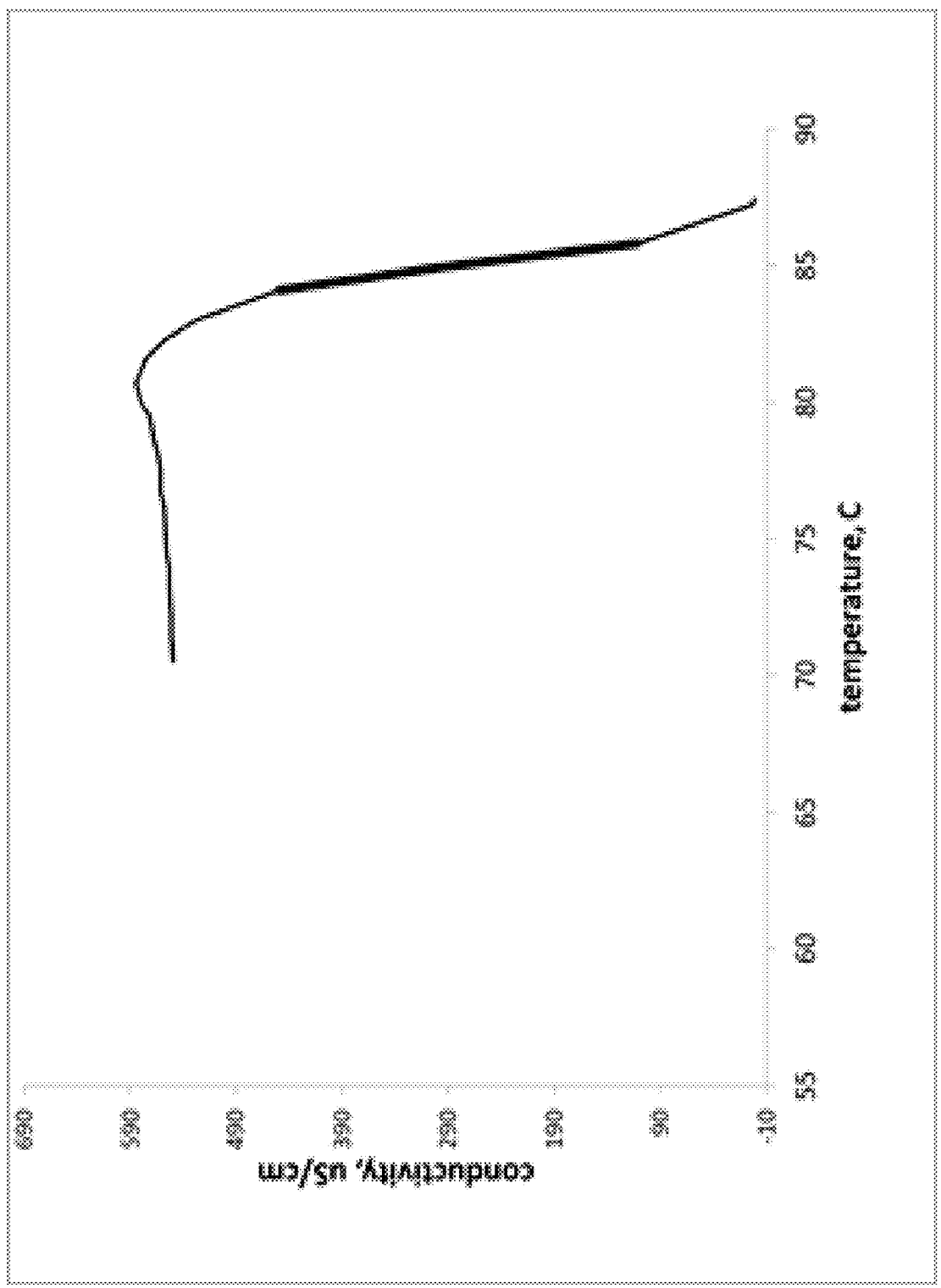
FIG. 14 is a graph of conductivity (uS/cm) vs. Temperature (° C.) for Example 23.

Preparation of Ibuprofen Nanocapsules with Sorbitan Oleate, a Polyethoxylated High HLB Surfactant, Isopropyl Myristate, Medium Chain Triglyceride, and d-Limonene A microemulsion composition was prepared from 6.0 grams of sorbitan oleate (product of Sigma Aldrich, Milwaukee, Wis.), 13.6 grams ceteareth-30 (source: Making Cosmetics, Snoqualmie, Wash.), 17.0 grams isopropyl myristate (product of Lotioncrafter, Eastsound Wash.), 17.1 grams of medium chain triglyceride oil (Kollisolv MCT 70, product of BASF), 7.0 grams ibuprofen (product of BASF), 5.1 grams of d-limonene (source: Nature's Oil, Streetsboro, Ohio) and 72.0 grams of dilute aqueous NaCl (conductivity=1000 uS/cm). This composition contains 5.1 weight percent (%) ibuprofen. When heated to 90° C. and allowed to cool, the composition was a transparent microemulsion between 84° C. and 86° C. A plot of conductivity vs. temperature is shown in FIG. 14. The regions where the composition was transparent or hazy transparent is indicated by a wide line in the plot. The microemulsion composition was heated to about 90° C. and allowed to cool with stirring to 86° C. and quenched into a stainless-steel pan cooled to −5° C. to give a translucent gel. The volume average and number average particle sizes measured by DLS were 50 nm and 29 nm, respectively. When stored at 2 to 4° C., crystals were not observed after 70 days and first observed after 80 days. When stored at 40° C., the sample was stable with respect to phase separation for 10 days and phase separation was first observed after 30 days (see Table 2).

TABLE 2

| Weight Percent | Ingredient | |
|---|---|---|
| 4.4 | sorbitan oleate | sorbitan ester surfactant |
| 9.9 | ceteareth-30 | ether poly(ethoxylate) surfactant |
| 12.3 | isopropyl myristate | isopropyl myristate |
| 12.4 | medium chain triglyceride oil | medium chain triglyceride oil |
| 3.7 | limonene | |
| 5.1 | ibuprofen | |
| 52.2 | water | |
| 100.0 | total | |

Skin permeability through human cadaver skin (source: National Disease Research Interchange, Philadelphia Pa.) was measured using 0.84 cm2 diameter Franz cells at 37° C. with 5 mL of pH7.4 phosphate buffered saline (product of Sigma Aldrich). After 6 hours of permeation, HPLC analysis of buffer solution in the receiver compartment showed that a total of 80 ug of ibuprofen had permeated the skin for an average flux of 13 ug/cm2/hr. A comparison permeation experiment was done with Proff Schmerz Créme topical ibuprofen cream (product of Dolorgeit GmbH &Co., Sankt Augustin, DE) under identical conditions using cadaver skin from the same donor. HPLC analysis of buffer solution in the receiver compartment with Proff Schmerz Créme showed that a total of 31 ug of ibuprofen had permeated the skin for an average flux of 5 ug/cm2/hr.

In Examples 24-28, ceteareth-30 was replaced with other polyethoxylated high HLB surfactants. Compositions of each of the Examples is presented in Table 3, along with the particle size of the resulting dispersion product and stability at 40° C. (i.e., days of 40° C. storage until phase separation is observed).

Examples 23-28 show that stable nanoparticle dispersions can be made with a composition comprising sorbitan oleate, a polyethoxylated high HLB ether surfactant, isopropyl myristate, medium chain triglyceride oil, d-limonene and ibuprofen but that unstable, large particle size dispersions are formed when the polyethoxylated high HLB surfactant includes an ester group.

TABLE 3

| | Example | | | | | |
|---|---|---|---|---|---|---|
| | 23 | 24 | 25 | 26 | 27 | 28 |
| ceteareth-30 | 13.5 | | | | | |
| steareth-40 | | 13.5 | | | | |
| PEG32 stearate | | | 13.5 | | | |
| PEG40 stearate | | | | 13.5 | | |
| Polysorbate 80 | | | | | 13.5 | |
| PEG30 glyceryl cocoate | | | | | | 13.5 |
| sorbitan oleate | 6.0 | 6.0 | 6.0 | 6.0 | 6.0 | 6.0 |
| isopropyl myristate | 17.0 | 17.0 | 17.0 | 17.0 | 17.0 | 17.0 |
| medium than triglyceride oil | 17.0 | 17.0 | 17.0 | 17.0 | 17.0 | 17.0 |
| d-limonene | 5.0 | 5.0 | 5.0 | 5.0 | 5.0 | 5.0 |
| aqueous 715 ppm NaCl | 72 | 72 | 72 | 72 | 72 | 72 |
| volume average particle size of the nanoparticle dispersion | 50 | 89 | 184 | 579 | 361 | 2962 |
| days stable at 40 C. | >269 | >12 | <1 | <1 | <1 | <1 |

Examples 29-32

Figure 15:
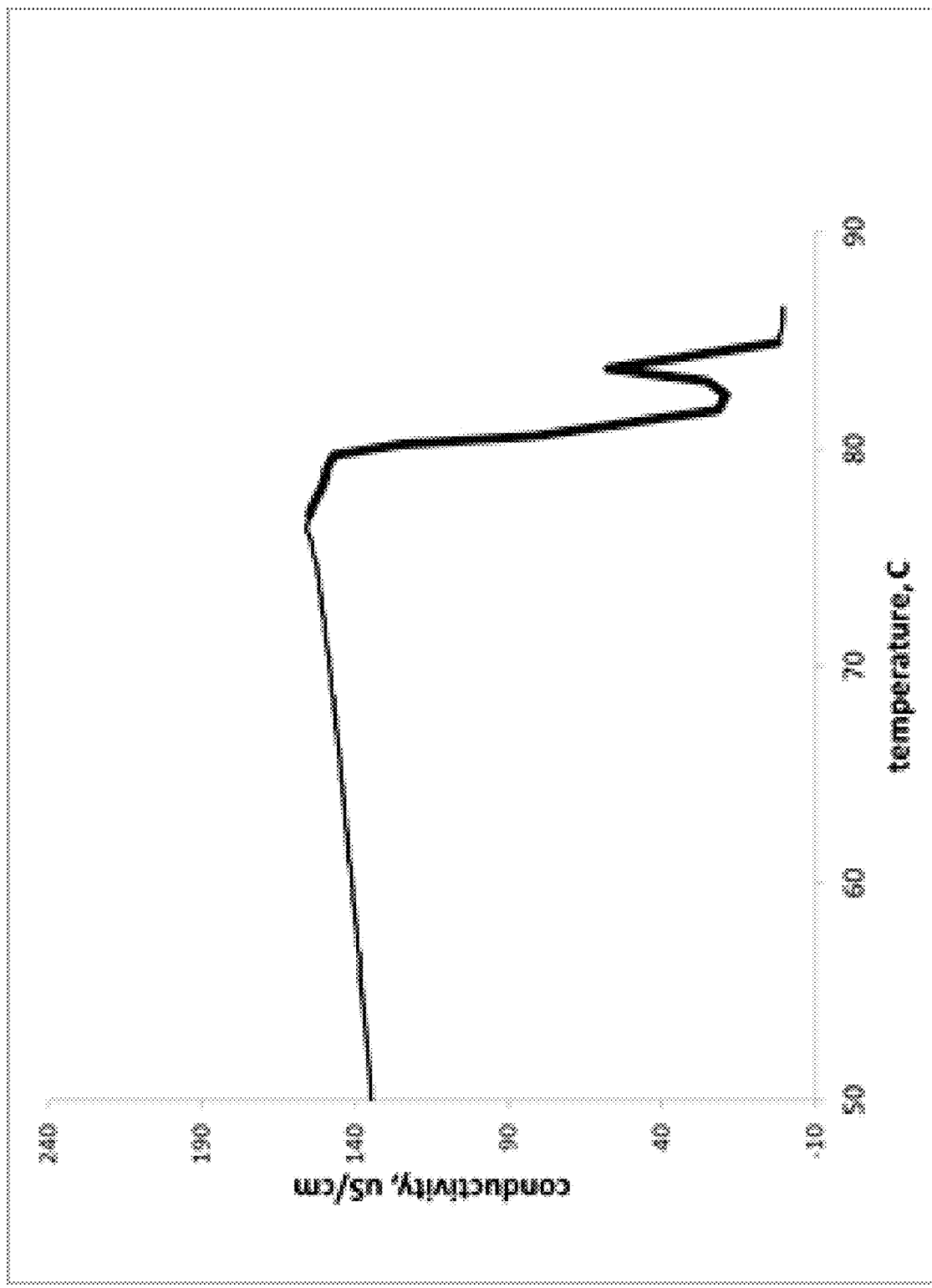
FIG. 15 is a graph of conductivity (uS/cm) vs. Temperature (° C.) for Example 24.
Figure 16:
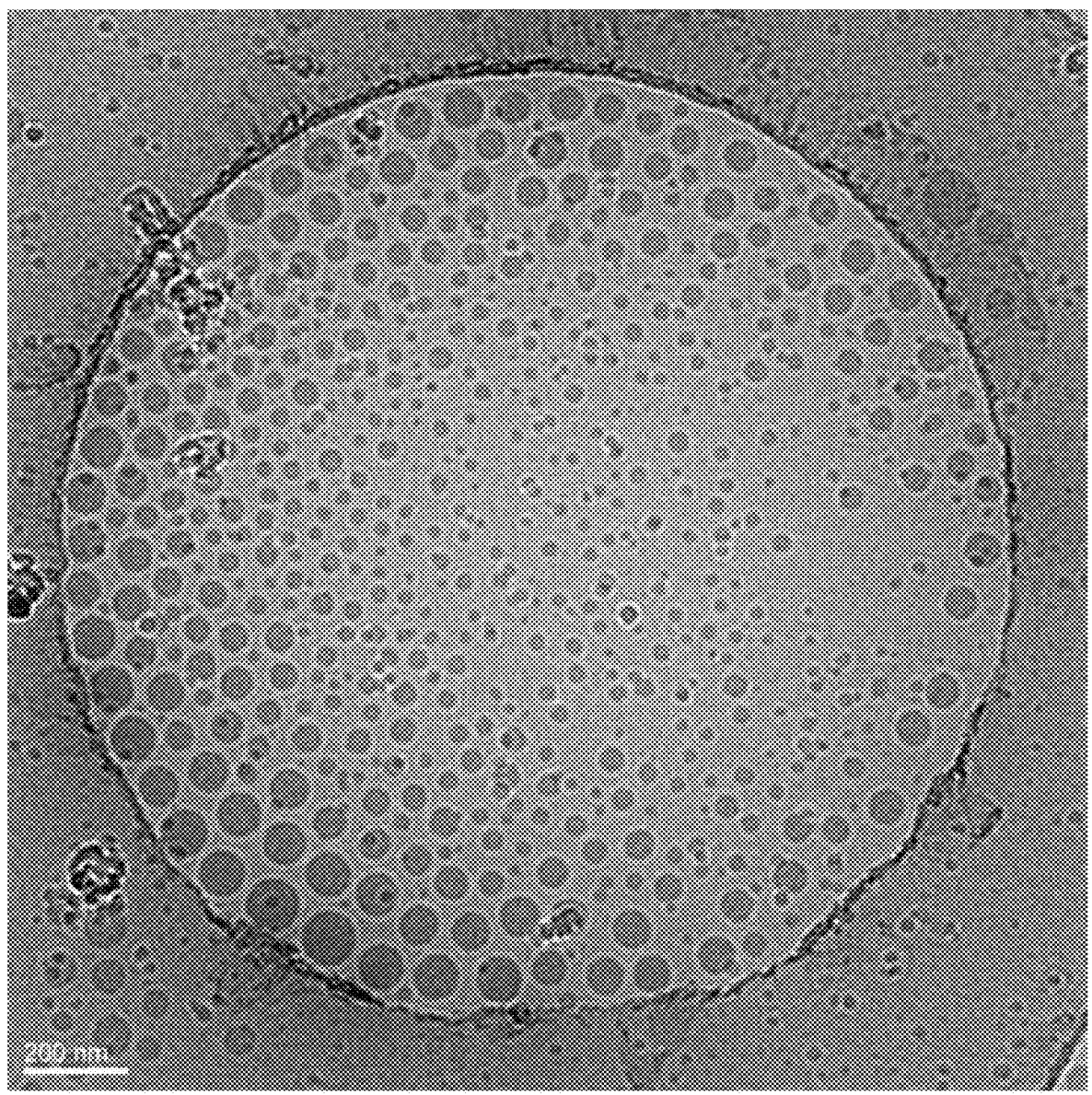
FIG. 16 is a Cryo-TEM micrograph of nanoparticles of Example 29.

Preparation of Ibuprofen Nanocapsules with Sorbitan Oleate, Laureth-23, PEG-100 Stearate, Dioleyl Phosphatidyl Choline, Isopropyl Myristate, d-Limonene, and Caprylic/Capric Triglyceride Oi A microemulsion composition was prepared from 4.0 grams of sorbitan oleate (product of Sigma Aldrich, Milwaukee, Wis.), 0.69 grams 90% dioleyl phosphatidyl choline (Phospholipon 90G, product of Lipoid USA, Newark N.J., dissolved in 1.4 gram of Caprylic/capric Triglyceride oil (CAS Number 65381-09-1, source: Lotioncrafter FCO), 8.0 grams laureth-23 (source: Lotioncrafter), 26.5 grams isopropyl myristate (product of Lotioncrafter), 6.7 grams S-ibuprofen (product of AK Scientific, Union City. Calif.), 6.7 grams of d-limonene (source: Nature's Oil) and 70.4 grams of water. This composition contains 5.1 weight percent (%) S-ibuprofen. When heated to 90° C. and allowed to cool, the composition was a transparent microemulsion between 77° C. and 85° C. A plot of conductivity vs. temperature is shown in FIG. 15. The regions where the composition was transparent or hazy transparent is indicated by a wide line in the plot. The microemulsion composition was heated to about 90° C. and allowed to cool with stirring to 78° C. and quenched into a stainless-steel pan cooled to −5° C. to give a translucent gel. The volume average and number average particle sizes measured by DLS were 59 nm and 31 nm, respectively. Cryo-TEM analysis of the nanoparticle dispersion showed that the nanoparticles were spherical, non-vesicular as shown in FIG. 16. When stored at 2 to 4° C., crystals were not observed after 240 days. When stored at 40° C., the sample was stable with respect to phase separation for at least 108 days and phase separation was not observed until after 219 days (See Table 4).

TABLE 4

| Weight Percent | Ingredient | |
|---|---|---|
| 3.07 | sorbitan oleate | sorbitan ester surfactant |
| 6.16 | laureth-23 | ether poly(ethoxylate) surfactant (5.21 mmol) |

TABLE 4-continued

| Weight Percent | Ingredient | |
|---|---|---|
| 4.59 | PEG100 stearate | ester(polyethoxylate surfactant with (0.98 mmol) |
| 20.34 | isopropyl myristate | isopropyl myristate |
| 0.53 | 33% Phospholipon 90G/FCO | phospholipid compound |
| 5.14 | AK Scientific s-ibuprofen | ibuprofen |
| 54.01 | Water | |
| 1.06 | Caprylic/capric Triglyceride | |
| 5.11 | Limonene | |
| 100.00 | Total | |

The mole ratio of ether poly(ethoxylate) surfactant to ester poly(ethoxylate) surfactant is 5.3 to 1 and the number average ethoxylate chain length is 35.2.

Skin permeability through human cadaver skin (source: National Disease Research Interchange, Philadelphia, Pa.) was measured using 0.64 cm² diameter Franz cells at 37° C. with 5 mL of pH 7.4 phosphate buffered saline (product of Sigma Aldrich). After 6 hours of permeation, HPLC analysis of buffer solution in the receiver compartment showed that a total of 83 ug of ibuprofen had permeated the skin for an average flux of 14 ug/cm2/hour (flux of S-ibuprofen=14 ug/cm2/hour). A comparison permeation experiment was done with Proff Schmerz Créme topical ibuprofen cream under identical conditions using cadaver skin from the same donor. HPLC analysis of buffer solution in the receiver compartment with Proff Schmerz Créme showed that a total of 39 ug of ibuprofen had permeated the skin for an average flux of 7 ug/cm2/hour (flux of S-ibuprofen=3.5 ug/cm2/hour).

In Examples 30-32, the mixture of laureth-23 and PEG100 stearate was replaced with other polyethoxylated high HLB surfactants and S-ibuprofen was replaced with racemic ibuprofen. Compositions of each of the Examples is presented in Table 5, along with the particle size of the resulting dispersion product and stability at 40° C. (i.e., days of 40° C. storage until phase separation is observed).

Examples 29-32 show that stable nanoparticle dispersions can be made with a composition comprising sorbitan oleate, a mixture of polyethoxylated high HLB ether and ester surfacants such that the fraction of ether surfactant is greater than 50 weight percent, isopropyl myristate, caprylic/capric triglyceride oil, d-limonene, Phospholipon 90G, and ibuprofen.

TABLE 5

| | Example | | | |
|---|---|---|---|---|
| | 29 | 30 | 31 | 32 |
| laureth-23 | 8.0 | | | |
| steareth-20 | | 8.1 | | |
| oleth-20 | | | 8.0 | |
| laureth-30 | | | | 14.0 |
| PEG100 stearate | 6.0 | 6.0 | 6.0 | |
| Phospholipon 90G | 0.7 | 0.7 | 0.7 | 0.7 |
| sorbitan oleate | 4.0 | 4.0 | 4.0 | 4.0 |
| isopropyl myristate | 17.0 | 17.0 | 17.0 | 17.0 |
| capric/caprylic triglyceride | 1.4 | 1.4 | 1.4 | 1.4 |
| d-limonene | 6.7 | 6.7 | 6.7 | 6.7 |
| water | 70.4 | 70.4 | 70.4 | 70.4 |
| volume average particle size of the nanoparticle dispersion | 59 | 61 | 63 | 48 |
| days stable at 40 C. | >269 | >12 | >6 | >6 |

Examples 33-40

Figure 17:
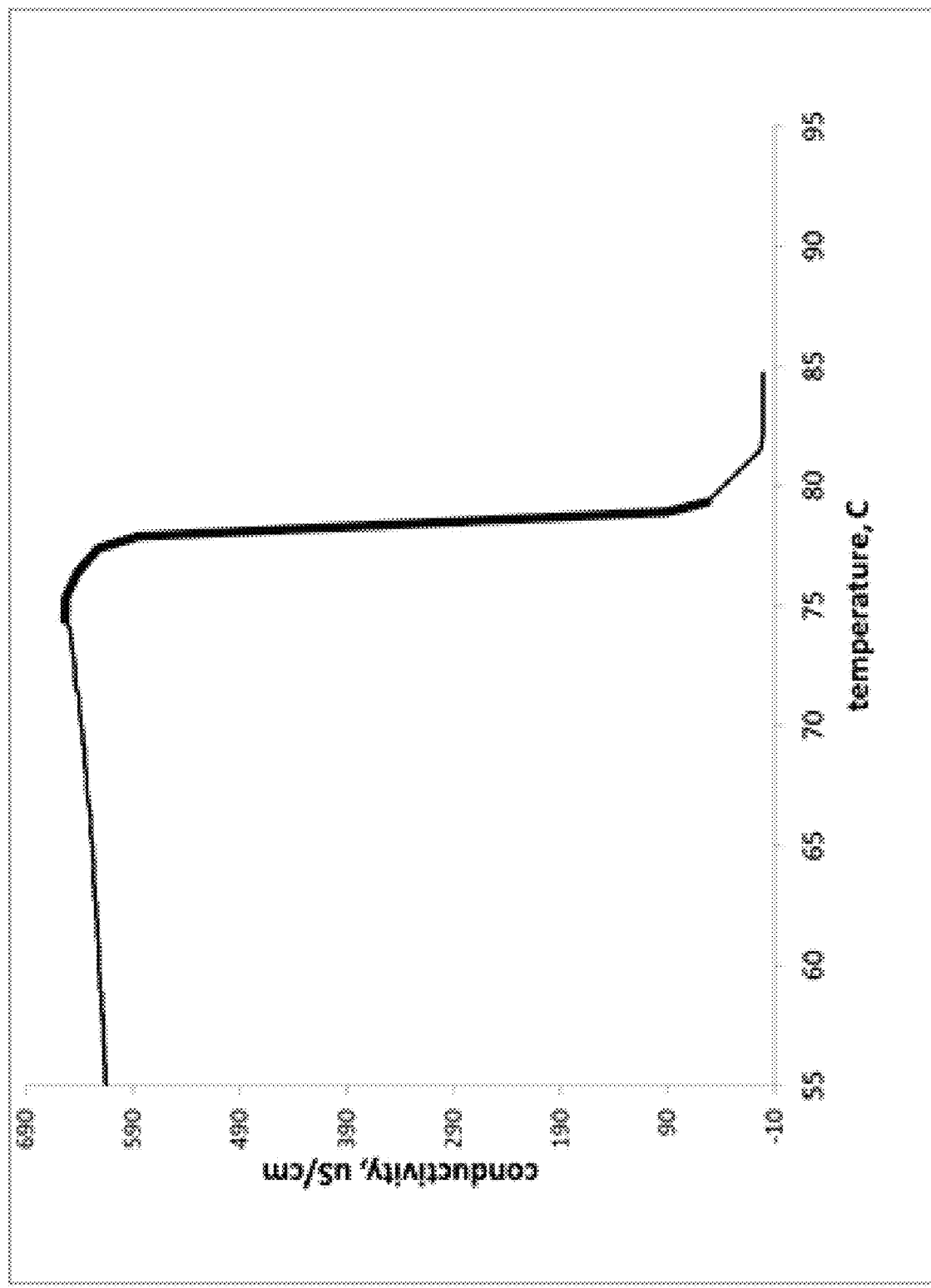
FIG. 17 is a graph of conductivity (uS/cm) vs. Temperature (° C.) for Example 33.

Preparation of Ibuprofen Nanocapsules with Sorbitan Oleate, Ceteareth-30, Ibuprofen, d-Limonene and Water Immiscible Oils A microemulsion composition was prepared from 6.0 grams of sorbitan oleate (product of Sigma Aldrich, Milwaukee Wis.), 13.6 grams ceteareth-30 (source: Making Cosmetics, Snoqualmie, Wash.), 34.0 grams isopropyl myristate (product of Lotioncrafter, Eastsound Wash.), 7.0 grams ibuprofen (product of BASF), 5.0 grams of d-limonene (source: Nature's Oil. Streetsboro Ohio) and 72.0 grams of dilute aqueous NaCl (conductivity=1000 uS/cm). This composition contains 5.1 weight percent (%) ibuprofen. When heated to 90° C. and allowed to cool, the composition was a transparent microemulsion between 74° C. and 79° C. A plot of conductivity vs. temperature is shown in FIG. 17. The regions where the composition was transparent or hazy transparent is indicated by a wide line in the plot. The microemulsion composition was heated to about 90° C. and allowed to cool with stirring to 79° C. and quenched into a stainless-steel pan cooled to −5'C to give a translucent gel. The volume average and number average particle sizes measured by DLS were 43 nm and 28 nm, respectively. When stored at 40° C., the sample was stable with respect to phase separation for at least 17 days. In Examples 34-39, isopropyl myristate was replaced with other oils. Compositions of each of the Examples is presented in Table 6, along with the particle size of the resulting dispersion product and stability at 40° C. (i.e., days of 40° C. storage until phase separation is observed).

What Examples 33-40 show is that stable nanoparticle dispersions can be made with a composition comprising ceteareth-30, sorbitan oleate, d-limonene, ibuprofen, and a variety of water immiscible oils.

TABLE 6

| | Example | | | | | | | |
|---|---|---|---|---|---|---|---|---|
| | 33 | 34 | 35 | 36 | 37 | 38 | 39 | 40 |
| ceteareth-30 | 13.5 | | | | | | | |
| sorbitan oleate | 6.0 | 6.0 | 6,0 | 6,0 | 6.0 | 6.0 | 6.0 | 6.0 |
| isopropyl myristate | 34.0 | 24.0 | 24.0 | 17.0 | 17.0 | | | |
| sesame seed oil | | 10.0 | | | | | | |
| cetyl palmitate | | | 10.0 | | | | | |
| light mineral oil | | | | 17.0 | | | | |
| diisopropyl adipate | | | | | 17.0 | | | |
| cocoyl caprylocaprate | | | | | | 34.0 | | |
| squalane | | | | | | | 34.0 | |
| propylene glycocl dicaprylate | | | | | | | | 34.0 |
| d-limonene | 5.0 | 5.0 | 5.0 | 5.0 | 5.0 | 5.0 | 5.0 | 5.0 |
| aqueous 715 ppm NaCl | 72 | 72 | 72 | 72 | 72 | 72 | 72 | 72 |
| volume average particle size of the nanoparticle dispersion | 43 | 59.7 | 53.5 | 27.6 | 91.2 | 52 | 40 | 104.2 |
| days stable at 40 C. | >17 | >4 | >3 | >4 | >2 | >17 | >11 | >11 |

Example 41

Example 33 was repeated except that PEG32 stearate replaced ceteareth-30. A composition was prepared from 6.0 grams of sorbitan oleate (product of Sigma Aldrich, Milwaukee Wis.), 13.6 grams PEG32 stearate (Jeemate 1540-DPS, source: Jeen International Corp., Fairfield, N.J.), 34.0 grams isopropyl myristate (product of Lotioncrafter, Eastsound Wash.), 7.0 grams ibuprofen (product of BASF), 5.0 grams of d-limonene (source: Nature's Oil, Streetsboro Ohio) and 72.0 grams of dilute aqueous NaCl (conductivity=1000 uS/cm). This composition contains 5.1 weight percent (%) ibuprofen. When heated to 90° C. and allowed to cool, the composition was not a transparent microemulsion between 50° C. and 90° C. and showed a phase inversion with a midpoint at 84° C. The microemulsion composition was heated to about 90° C. and allowed to cool with stirring to 84° C. and quenched into a stainless-steel pan cooled to −5° C. to give an opaque liquid. The volume average and number average particle sizes measured by DLS were 342 nm and 115 nm, respectively. When stored at 40 C., the sample phase separated in less than two days. What this example shows is that when PEG32 stearate, a polyethoxylated high HLB ester surfactant, is used to replace ceteareth-30, a polyethoxylated high HLB ether surfactant, the composition does not give a transparent microemulsion and converts on cooling to give a dispersion with large particle size which phase separates within 2 days at 40° C.

Example 42

Example F3 as described in Table 1 of U.S. Pat. No. 6,221,370 was repeated except that some of the capric/caprylic triglyceride plus paraffin oil mixture was replaced with ibuprofen and the concentration of lipids and surfactants increased. Accordingly, when 8.0 g of PEG32 stearate, 8.0 g of glyceryl monostearate, 15.9 g of light mineral oil (Drakeol 7, available from CQ Concepts, Ringwood Ill.), 15.9 g of fractionated coconut oil (Lotioncrafter), and 5.7 g of ibuprofen were heated to 90° C. and allowed to cool, the composition was not a transparent microemulsion between 50° C. and 90° C. and showed a phase inversion with a midpoint at 80° C. What this Example shows is that compositions for emulsification by the PIT method using emulsifier mixtures of U.S. Pat. No. 6,221,370 which include a polyethoxylated high HLB ester surfactant fail to give microemulsions in the case that the composition includes ibuprofen.

Example 43

Example 42 was repeated except that PEG32 stearate was replaced with an equal amount of ceteareth-30. Accordingly, when 8.0 g of ceteareth-30, 8.0 g of glyceryl monostearate, 15.9 g of light mineral oil, 15.9 g of fractionated coconut oil (Lotioncrafter), and 5.7 g of ibuprofen were heated to 90° C. and allowed to cool, the composition showed a phase inversion with a midpoint at 74° C. and had the form of a transparent microemulsion between 73° C. and 78° C. and. What this Example shows is that compositions for emulsification by the PIT method using emulsifier mixtures of U.S. Pat. No. 6,221,370 which fail to give microemulsions in the case that the composition includes ibuprofen and a polyethoxylated high HLB ester surfactant give microemulsions in the case that the polyethoxylated high HLB ester surfactant is replaced with a polyethoxylated high HLB ether surfactant.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance or component fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention.

Applicant reserves the right to physically incorporate into this specification any and all materials and information from any such patents, applications, publications, scientific articles, web sites, electronically available information, and other referenced materials or documents. Applicant reserves the right to physically incorporate into any part of this document, including any part of the written description, the claims referred to above including but not limited to any original claims.

What is claimed is:

1. A nanoparticle dispersion for topical delivery to skin of a mammal, the nanoparticle dispersion consisting of:
    sorbitan oleate;
    one or more poly(ethoxylate) surfactants selected from ceteareth-30 and the combination of laureth-23 and PEG100 stearate;
    one or more water immiscible oils each independently consisting of a medium chain triglyceride oil, caprylic/capric triglyceride, d-limonene, squalane, cetyl palmitate, coco-caprylate/caprate, isopropyl myristate, propylene glycol dicaprylate, mineral oil, coconut oil, sesame seed oil, fractionated coconut oil, diisopropyl adipate, or combinations thereof;
ibuprofen; and
water.

2. The nanoparticle dispersion for topical delivery to skin of a mammal of claim 1, wherein a volume average particle size of the nanoparticle dispersion is less than about 100 nm.

3. The nanoparticle dispersion for topical delivery to skin of a mammal of claim 1, wherein the ibuprofen has greater than about 95% enantiomeric excess of an S-(+)-optical isomer.

4. The nanoparticle dispersion for topical delivery to skin of a mammal of claim 1 consisting of:
sorbitan oleate;
ceteareth-30;
isopropyl myristate;
medium chain triglyceride oil;
d-limonene;
ibuprofen;
and water.

5. The nanoparticle dispersion for topical delivery to skin of a mammal of claim 1 consisting of:
sorbitan oleate;
ceteareth-30;
isopropyl myristate;
d-limonene;
ibuprofen;
and water.

6. A nanoparticle dispersion for topical delivery to skin of a mammal, the nanoparticle dispersion consisting of:
sorbitan oleate;
ceteareth-30;
isopropyl myristate;
a medium chain triglyceride oil;
ibuprofen;
water,
wherein the ibuprofen does not form crystals from the nanoparticle dispersion for greater than about 14 days at a temperature from about 2° C. to about 4° C., and
wherein a volume average particle size of the nanoparticle dispersion is less than about 100 nm.

7. The nanoparticle dispersion for topical delivery to skin of a mammal of claim 6, wherein the ibuprofen has greater than about 95% enantiomeric excess of an S-(+)-optical isomer.

8. A nanoparticle dispersion for topical delivery to skin of a mammal, the nanoparticle dispersion consisting of:
sorbitan oleate;
one or more poly(ethoxylate) surfactants selected from ceteareth-30 and the combination of laureth-23 and PEG100 stearate;
one or more water immiscible oils each independently consisting of a medium chain triglyceride oil, caprylic/capric triglyceride, d-limonene, squalane, cetyl palmitate, coco-caprylate/caprate, isopropyl myristate, propylene glycol dicaprylate, mineral oil, coconut oil, sesame seed oil, fractionated coconut oil, diisopropyl adipate, or combinations thereof;
ibuprofen;
water,
wherein the ibuprofen does not form crystals from the nanoparticle dispersion for greater than about 14 days at a temperature from about 2° C. to about 4° C., and
wherein a volume average particle size of the nanoparticle dispersion is less than about 100 nm.

* * * * *